(12) United States Patent
Coronella et al.

(10) Patent No.: US 11,242,403 B2
(45) Date of Patent: Feb. 8, 2022

(54) SYNDECAN-1 (CD138) BINDING AGENTS AND USES THEREOF

(71) Applicant: MITSUBISHI TANABE PHARMA CORPORATION, Osaka (JP)

(72) Inventors: Julia Coronella, Carlsbad, CA (US); Robyn Richardson, San Diego, CA (US); Anjuli Timmer, San Diego, CA (US); Roland Newman, San Diego, CA (US)

(73) Assignee: MITSUBISHI TANABE PHARMA CORPORATION, Osaka (JP)

( * ) Notice: Subject to any disclaimer, the term of this patent is extended or adjusted under 35 U.S.C. 154(b) by 100 days.

(21) Appl. No.: 16/607,492

(22) PCT Filed: Apr. 25, 2018

(86) PCT No.: PCT/JP2018/016847
§ 371 (c)(1),
(2) Date: Oct. 23, 2019

(87) PCT Pub. No.: WO2018/199176
PCT Pub. Date: Nov. 1, 2018

(65) Prior Publication Data
US 2020/0181278 A1 Jun. 11, 2020

Related U.S. Application Data

(60) Provisional application No. 62/490,463, filed on Apr. 26, 2017.

(51) Int. Cl.
C07K 16/28 (2006.01)

(52) U.S. Cl.
CPC ...... *C07K 16/2896* (2013.01); *C07K 2317/24* (2013.01); *C07K 2317/33* (2013.01); *C07K 2317/55* (2013.01); *C07K 2317/565* (2013.01); *C07K 2317/92* (2013.01)

(58) Field of Classification Search
None
See application file for complete search history.

(56) References Cited

U.S. PATENT DOCUMENTS

| 9,289,509 B2 | 3/2016 | Osterroth et al. | |
|---|---|---|---|
| 2015/0196663 A1* | 7/2015 | Shusta | A61K 9/0085 424/178.1 |
| 2015/0266947 A1* | 9/2015 | Sierks | G01N 33/6896 424/135.1 |

(Continued)

FOREIGN PATENT DOCUMENTS

| WO | WO2008068048 | * | 6/2008 |
|---|---|---|---|
| WO | 2009/080829 A1 | | 7/2009 |
| WO | 2018/199176 A1 | | 11/2018 |

OTHER PUBLICATIONS

Chen "Enhancement and destruction of antibody function by somatic mutation: unequal occurrence is controlled by V gene combinatorial associations" EMBO 14(12):2784-2794 (Year: 1995).*

(Continued)

*Primary Examiner* — Adam Weidner
(74) *Attorney, Agent, or Firm* — Pillsbury Winthrop Shaw Pittman, LLP

(57) ABSTRACT

Presented herein, in certain embodiments, are compositions comprising binding agents that specifically bind to syndecan-1 and uses thereof.

23 Claims, 9 Drawing Sheets

Specification includes a Sequence Listing.

(56) References Cited

U.S. PATENT DOCUMENTS

2017/0355756 A1* 12/2017 Julien .................. C12N 15/86
2019/0100588 A1   4/2019 Chaganty et al.

OTHER PUBLICATIONS

Kussie "A Single Engineered Amino Acid Substitution Changes Antibody Fine Specificity" J immunol 152(1):146-52 (Year: 1994).*

Patent Cooperation Treaty, International Search Report issued in PCT/JP2018/016847, dated Jul. 24, 2018, pp. 1-3.

Patent Cooperation Treaty, International Preliminary Report on Patentability issued in PCT/JP2018/016847, dated Nov. 7, 2019, pp. 1-8.

Tassone et al., Cytotoxic activity of the maytansinoid immunoconjugate B-B4-DMI against CD138+ multiple myeloma cells, Blood, 2004, pp. 3688-3696. vol. 104(12).

Wijdenes et al., A plasmocyte selective monoclonal antibody (B-B4) recognizes syndecan-1, Br. J. Haematol, 1996, pp. 318-323, vol. 94(2).

Dore et al., Identification and location on syndecan-1 core protein of the epitopes of B-B2 and B-B4 monoclonal antibodies, FEBS Lett., 1998, pp. 67-70, vol. 426(1).

European Patent Office, Extended European Search Report issued in EP Patent Application No. 18790752.2, dated Dec. 18, 2020, pp. 1-10.

Orecchia et al., "A novel human anti-syndecen-1 antibody inhibits vascular maturation and tumor growth in melanoma", European Journal of Cancer, 2013, pp. 2022-2033, vol. 49(8).

Gharbaran, "Advances in the molecular functions of syndecan-1 (SDC1/CD138) in the pathogenesis of malignancies", Critical Reviews in Oncology/Hematology, 2014, pp. 1-17, vol. 94(1).

Bae et al., "Novel epitope evoking CD138 antigen-specific cytotoxic T lymphocytes targeting multiple myeloma and other plasma cell disorders", British Journal of Haematology, Sep. 1, 2011, pp. 1-13.

* cited by examiner

[Fig. 1]

```
Human  (1)   MRRAALWLWLCALALSLQPALPQIVATNLPPEDQDGSGDSDNPSGSGAGALQDITLSQQTPSTWKDTQLLTAIP
Cyno   (1)   MRRAALWLWLCALALSLQPAMPQIVATNLPPEDQDGSGDSDNPSGSGAGALQDITLSQQTPSTWKDTWLVPATP
Mouse  (1)   MRRAALWLWLCALALRLQPALPQIVAVNVPPEDQDGSGDSDNPSGSGTGALPD-TLSRQTESTWKDVWLLTATP Human  (76)  TSFEPTGLEATASTETLHAGEGHVVLPEVEPLTARRQE--ATERPHETTQLPTTKQASTTHATTAQEP
Cyno   (76)  MSFEPTGLEATAASTSTLQAGEGHKEGEAVVLLEVEELLTARRQE--ATEQPTETRQLPTTRQAFTAHATTAQEP
Mouse  (76)  TAFEPTSSNTETAFTSVLHAGEFREEGEFVLHVEAEPCFTARIREKEVTHRPRETVQLPITQRJSTVRVTTAQAA Human (149)  ATSHPHRIMQPGHHETSTPAGPSQADLHTPHTEDGGPSATERAAEDGASSQLPAAEGSGHQDFTEFTSGENTAVV
Cyno  (149)  ATSHEHRIMQEGHHETSAPAGPSQADLHTPRTEDGGPSATERAAEDGASSQLPAAEGSGEQHFTEFTSGENTALV
Mouse (150)  VFSHPHGGMCPGLHETSAPTAPGSPPAEGHGTSVIKEVVEDGTAMQLPAGEGSGEQHFTEFTSGENTAVA Human (224)  AVEEDRKNQSPVDQGATGASQGLLDPKEVLGGVLASGGLVGLIEAVCLVGEMLYRMKKDEGSYSLEEPKQANGGSA
Cyno  (224)  AVEEDHRMQSPVDPGATGASQSLLDRKEVLGSIIAGGLVGLIEAVCLVGEMLYRMKFDEGSYSLEEPKQANGGA
Mouse (225)  AVEPGLPRMQPPVDEGATGASQGSLLDPKEVLGGLVGLIEAVCLVAEMLYRMKFDEGSYSLEEPKQANGGA Human (299)  YQKPTKQEEFYA      (SEQ ID NO:1)
Cyno  (299)  YQKPTKQEEFYA      (SEQ ID NO:103)
Mouse (300)  YQKPTKQEEFYA      (SEQ ID NO:98)
```

[Fig. 3]
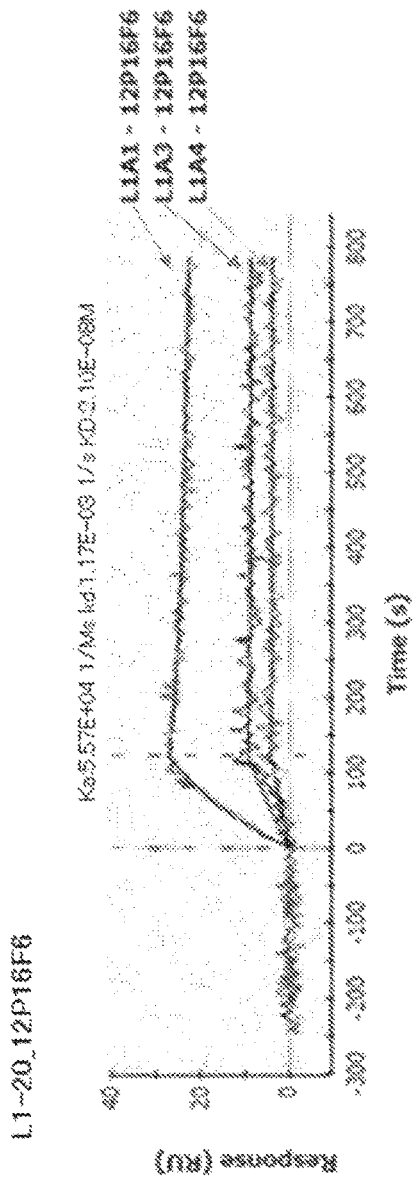

```
P1GF6 VH              (1)    QVQLQQSGAEVVKPGASVKLSCKASGYTFTSYYLYWVKQRPGQGLEWIGE
P1GF6 VH abb/sdr repair (1)  QVQLVQSGAEVVKPGASVKLSCKASGYTFTSYYLYWVKQRPGQGLEWIGE
P1GF6 VH cdr/ven repair (1)  QVQLVQSGAEVVKPGASVKLSCKASGYTFTSYYLYWVRKAPGQGLEWIGE
P1GF6 VH fra1 repair    (1)  QVQLVQSGAEVVKPGASVKLSCKASGYTFTSYYLYWVRKAPGQGLEWIGE
P1GF6 VH fra2 repair    (1)  QVQLQQSGAEVVKPGASVKLSCKASGYTFTSYYLYWVRKAPGQGLEWIGE P1GF6 VH              (51)   IYPRSGGTNINEKFLSKATLTADESSSTAYLQLSSLTSEDSAVYYCTRSL
P1GF6 VH abb/sdr repair (51) IYPRSGSTMYAEKFQGRVTLTADTSTSTAYLELSSLTSEDTAVYYCTRSL
P1GF6 VH cdr/ven repair (51) IYPLSGGTNINEKFLSRVTLTADTSTSTAYLELSSLTSEDTAVYYCTRSL
P1GF6 VH fra1 repair    (51) IYPRSGGTNINEKFLSRVTLTADTSTSTAYMLLSSLTSEDTAVYYCTRSL
P1GF6 VH fra2 repair    (51) IYPRSGGTNINEKFLSRYTITADESTSTVMQLSSLTSEDSAVYYCTRSL P1GF6 VH              (101)  LYWGQGTLITVSS  (SEQ ID NO: 77)
P1GF6 VH abb/sdr repair (101) LYWGQGTTLTVSS  (SEQ ID NO: 84)
P1GF6 VH cdr/ven repair (101) LYWGQGTLITVSS  (SEQ ID NO: 85)
P1GF6 VH fra1 repair    (101) LYWGQGTTLTVSS  (SEQ ID NO: 86)
P1GF6 VH fra2 repair    (101) LYWGQGTTLTVSS  (SEQ ID NO: 87)
```

[Fig. 5B]

```
p16F6 VL                    (1)    DVVMTQSPLSLPVTLGQPASISCKSSQSLLASDGKTYLNWLLQRPGQSPK
p16F6 VL fra repair         (1)    DVVMTQSPLSLSVTLGQPASISCKSSQSLLASDGKTYLNWLLQRPGQSPR
p16F6 VL abb repair         (1)    DVVMTQTPLSLPVGQPASISCKSSQSLLASDGKTYLNWLLQRPGQSPK
p16F6 VL sdr/cdr/ven repair (1)    DVVMTQSPLSLPVTPGQPASISCKSSQSLLASDGKTYLNWLLQRPGQSPK p16F6 VL                    (51)   RLIYLVSKLDSGVPDRFTGSASGTDFTLQISRVEAEDLGIYYCWQGAHFP
p16F6 VL fra repair         (51)   RLIYLVSKLDSGVPNRFSGSGSGTDFTLQISRVEAEDVGLYYCWQGAHFP
p16F6 VL abb repair         (51)   RLIYLVSKLDSGVPNRFSGSGSGTIETLQISRVEAEDVGLYYCMQGAHFP
p16F6 VL sdr/cdr/ven repair (51)   RLIYLVSKLDSGVPNRFSGSGSGTDFTLQISRVEAEDVGLYYCMQGAHFP p16F6 VL                    (101)  PTFGGGTKLEIKR   (SEQ ID NO: 35)
p16F6 VL fra repair         (101)  PTFGSGTKLEIKR   (SEQ ID NO: 44)
p16F6 VL abb repair         (101)  PTFGQGTKVEIKR   (SEQ ID NO: 43)
p16F6 VL sdr/cdr/ven repair (101)  PTFGQGTKLEIKR   (SEQ ID NO: 42)
```

[Fig. 6]
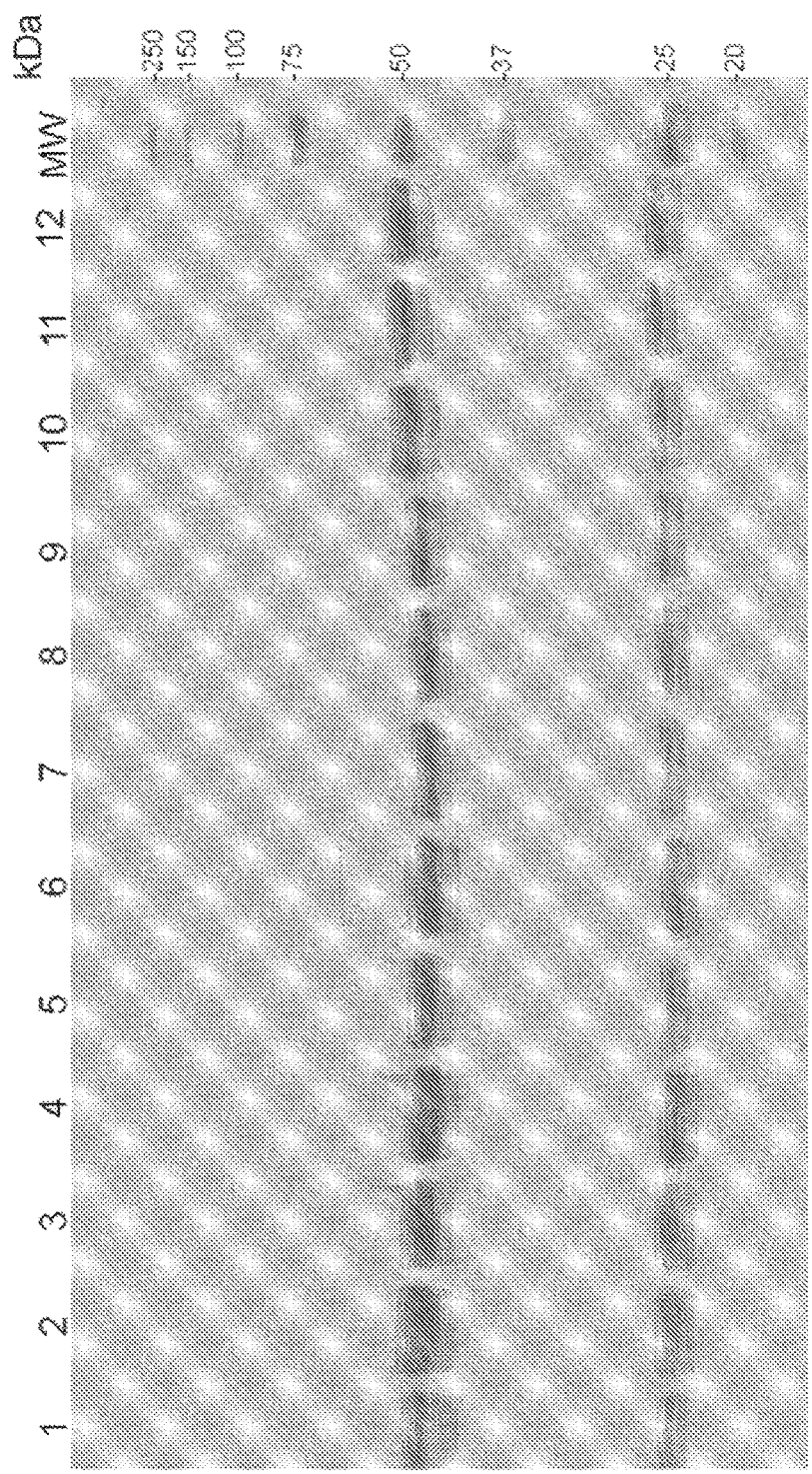

Fig. 8]
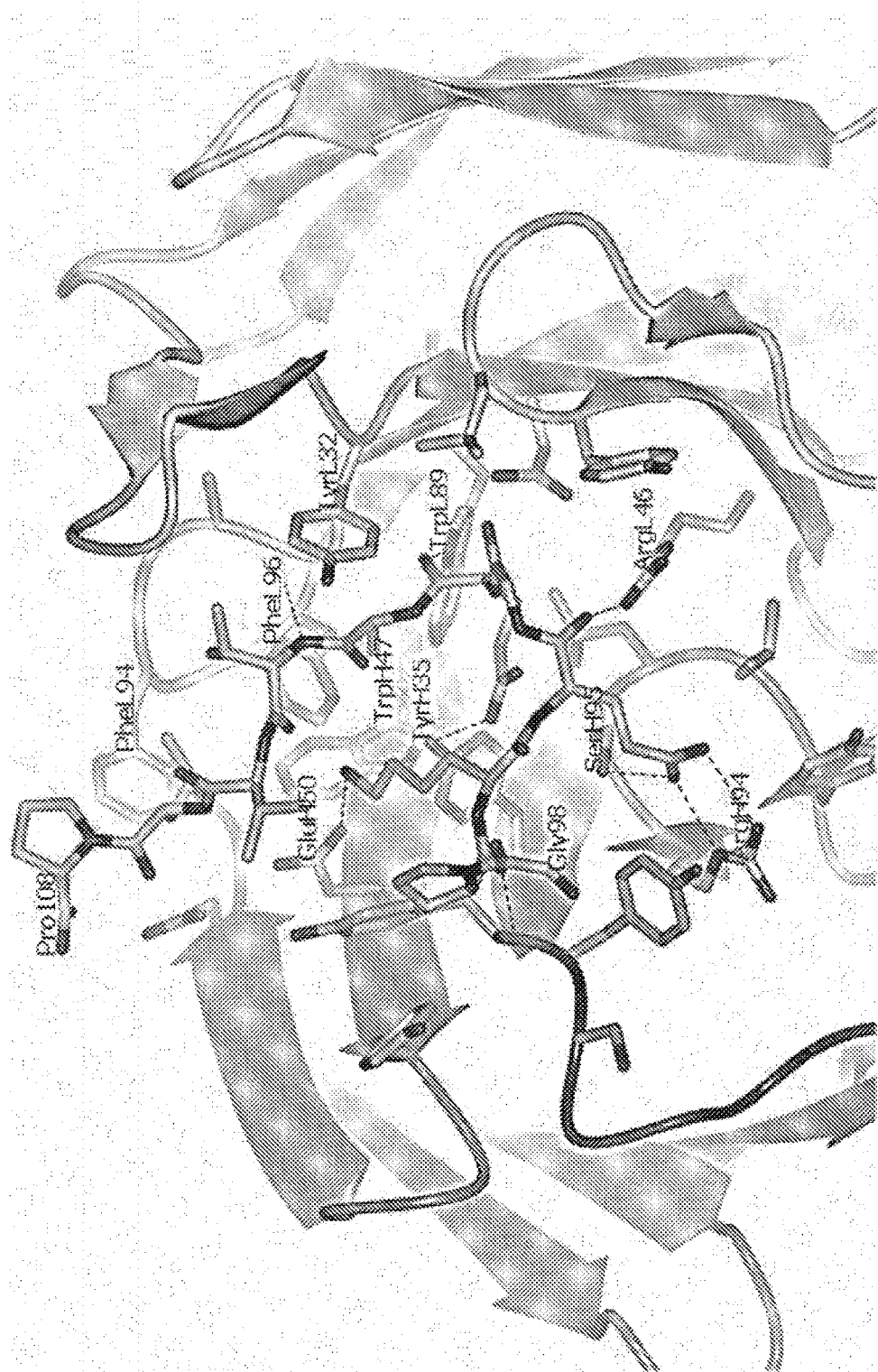

SYNDECAN-1 (CD138) BINDING AGENTS AND USES THEREOF

RELATED PATENT APPLICATIONS

This patent application is a national phase filing of, and claims the benefit of, International Patent Application No. PCT/JP2018/016847 filed on Apr. 25, 2018, entitled "SYNDECAN-1 (CD138) BINDING AGENTS AND USES THEREOF" claims the benefit of United States Provisional Patent Application No. 62/490,463 filed on Apr. 26, 2017, entitled "SYNDECAN-1 (CD138) BINDING AGENTS AND USES THEREOF" naming Julia Coronella, Robyn Richardson, Anjuli Timmer and Roland Newman as inventors. The entire content of the foregoing patent application is incorporated herein by reference, including all text, tables and drawings.

SEQUENCE LISTING

The present application is being filed with a Sequence Listing. The Sequence Listing is submitted electronically in ASCII format via EFS-Web in the form of a text file. Said ASCII copy, created on Oct. 21, 2019, is named 674112_sequence.txt and is 56.2 KB in size, the contents of which are incorporated herein by reference in their entirety.

TECHNICAL FIELD

Field of the Invention

Embodiments of the invention relate to compositions comprising binding agents that specifically bind to syndecan-1 (CD138), or a portion thereof, and uses thereof.

BACKGROUND ART

Introduction

The syndecan family consists of four transmembrane heparan sulfate proteoglycans (HSPGs) mainly present on the cell surface. The structures of these different syndecans show high homology in vertebrates and invertebrates. All four syndecans are built up of a core protein decorated with varying number of glycosaminoglycan (GAG) side chains. Syndecans exert their function mainly through these GAG chains, but the different domains of the core protein have distinct roles as well. Syndecan-1 and syndecan-3 carry both heparan sulfate (HS) and chondroitin sulfate (CS) chains, whereas syndecan-2 and syndecan-4 carry only HS chains. Syndecans are involved in a wide range of biological processes including growth and differentiation, cell spreading, cell adhesion, cell migration, cytoskeletal organization, infiltration, and angiogenesis.

Syndecan-1 is a transmembrane (Type 1) heparan sulfate proteoglycan comprising an N-terminal extracellular domain, a transmembrane domain and a C-terminal intracellular signaling domain. In humans syndecan-1 (CD138) comprises a core protein of 310 amino acids in length and is encoded by the SDC1 gene. The SDC1 gene consists of five exons and is located in human chromosome 2. The first exon encodes a signal peptide, the second exon encodes attachment sites for heparan sulfate, the third and fourth exons encode a site for chondroitin sulfate binding and the fifth exon encodes the transmembrane and cytoplasmic domains.

Syndecan-1 is expressed on the basolateral surface of epithelial cells in adult tissues, on mesenchymal cells during development, and on lymphoid cells during distinct stages of differentiation. Syndecan-1 can bind hepatocyte growth factor (HGF), can interact with various growth factors and act as a coreceptor resulting in the activation of multiple signaling pathways effecting cell migration, cell-matrix interactions, growth, proliferation and survival. Several studies have implicated a key role of syndecan-1 in various malignancies including lung cancer, breast cancer, head and neck carcinomas, gastrointestinal malignancies, myelomas and malignant mesothelioma, a highly aggressive mesenchymal tumor.

Presented herein are novel binding agents, monoclonal antibodies and binding portions thereof, that bind specifically to syndecan-1, pharmaceutical compositions thereof and methods of using the same.

SUMMARY OF INVENTION

In some aspects, presented herein is a binding agent that specifically binds to syndecan-1, an extracellular domain of syndecan-1 or a portion thereof. In some embodiments a binding agent described herein binds specifically to a protein or polypeptide that comprises syndecan-1, an extracellular domain of syndecan-1 or a portion thereof. In certain embodiments, a binding agent binds specifically to one or more mammalian syndecan-1 polypeptides selected from a human syndecan-1, non-human primate syndecan-1 (e.g., a monkey syndecan-1), a rat syndecan-1, and a mouse syndecan-1. In certain embodiments, a binding agent specifically binds to a variant of human syndecan-1 and/or to an extracellular domain of a human syndecan-1 comprising one or more naturally occurring variants.

In some aspects, presented herein is a syndecan-1 binding agent comprising one or more light chain complementary determining regions selected from a CDR-L1, a CDR-L2 and a CDR-L3, wherein the CDR-L1 comprises a polypeptide sequence having at least 80% identity to an amino acid sequence of a CDR-L1 selected from Table 1, the CDR-L2 comprises a polypeptide sequence having at least 80% identity to an amino acid sequence of a CDR-L2 selected from Table 2, and the CDR-L3 comprises a polypeptide sequence having at least 80% identity to an amino acid sequence of a CDR-L3 selected from Table 3, where the syndecan-1 binding agent specifically binds to syndecan-1, or a portion thereof. In some embodiments, the syndecan-1 binding agent comprises the CDR-L3 and optionally the CDR-L2. In some embodiments, the syndecan-1 binding agent comprises the CDR-L1, the CDR-L2 and the CDR-L3.

In some aspects, presented herein is a syndecan-1 binding agent comprising one or more heavy chain complementary determining regions selected from a CDR-H1, a CDR-H2 and a CDR-H3, wherein the CDR-H1 comprises a polypeptide sequence having at least 80% identity to an amino acid sequence of a CDR-H1 selected from Table 6, the CDR-H2 comprises a polypeptide sequence having at least 80% identity to an amino acid sequence of a CDR-H2 selected from Table 7, and the CDR-H3 comprises a polypeptide sequence having at least 80% identity to an amino acid sequence of a CDR-H3 selected from Table 8, where the syndecan-1 binding agent specifically binds to syndecan-1, or a portion thereof. In some embodiments a syndecan-1 binding agent comprising the CDR-H3. In some embodiments the syndecan-1 binding agent comprises the CDR-H1, the CDR-H2 and the CDR-H3.

In some aspects, presented herein is a syndecan-1 binding agent comprising one or more light chain complementary determining regions selected from a CDR-L1, a CDR-L2 and a CDR-L3, where the CDR-L1 comprises a polypeptide sequence having at least 80% identity to an amino acid sequence of a CDR-L1 selected from Table 1, the CDR-L2 comprises a polypeptide sequence having at least 80% identity to an amino acid sequence of a CDR-L2 selected from Table 2, and the CDR-L3 comprises a polypeptide sequence having at least 80% identity to an amino acid sequence of a CDR-L3 selected from Table 3.

In certain embodiments of a syndecan-1 binding agent presented herein the CDR-L1 comprises a polypeptide sequence having at least 90% identity to an amino acid sequence of a CDR-L1 selected from Table 1, the CDR-L2 comprises a polypeptide sequence having at least 90% identity to an amino acid sequence of a CDR-L2 selected from Table 2, and the CDR-L3 comprises a polypeptide sequence having at least 90% identity to an amino acid sequence of a CDR-L3 selected from Table 3. In some embodiments, the CDR-L1 comprises of a polypeptide sequence selected from Table 1, the CDR-L2 comprises a polypeptide sequence selected from Table 2, and the CDR-L3 comprises a polypeptide sequence selected from Table 3.

In certain embodiments of a syndecan-1 binding agent presented herein the CDR-H1 comprises a polypeptide sequence having at least 90% identity to an amino acid sequence of a CDR-H1 selected from Table 6, the CDR-H2 comprises a polypeptide sequence having at least 90% identity to an amino acid sequence of a CDR-H2 selected from Table 7, and the CDR-H3 comprises a polypeptide sequence having at least 90% identity to an amino acid sequence of a CDR-H3 selected from Table 8. In some embodiments, the CDR-H1 comprises a polypeptide sequence selected from Table 6, the CDR-H2 comprises a polypeptide sequence selected from Table 7, and the CDR-H3 comprises a polypeptide sequence selected from Table 8.

In some embodiments, a syndecan-1 binding agent comprises or consists of a CDR-H3. In some embodiments, a syndecan-1 binding agent comprises or consists of a CDR-H3 and a CDR-L3. In some embodiments, a syndecan-1 binding agent comprises or consists of a CDR-H3, a CDR-L3 and a CDR-H2 or a CDR-L2. In some embodiments, a syndecan-1 binding agent comprises or consists of a CDR-H3, a CDR-L3, a CDR-H2, a CDR-L2 and a CDR-H1 and/or CDR-L1. In some embodiments, the CDR regions are selected from one or more of Tables 1-10.

In some aspects, presented herein is a syndecan-1 binding agent comprising a CDR-L1, a CDR-L2 and a CDR-L3 which are three polypeptide sequences of a light chain complementary determining region (CDR-L), where the CDR-L1 is selected from Table 1, the CDR-L2 is selected from Table 2 and the CDR-L3 is selected from Table 3, and where the syndecan-1 binding agent specifically binds to syndecan-1, or a portion thereof.

In some aspects, presented herein is a syndecan-1 binding agent comprising a CDR-H1, a CDR-H2 and a CDR-H3 which are three polypeptide sequences of a heavy chain complementary determining region (CDR-H), where the CDR-H1 is selected from Table 6, the CDR-H2 is selected from Table 7 and the CDR-H3 is selected from Table 8, and where the syndecan-1 binding agent specifically binds to syndecan-1, or a portion thereof.

In some aspects, presented herein is a syndecan-1 binding agent comprising a CDR-L1 selected from Table 1, a CDR-L2 selected from Table 2, a CDR-L3 selected from Table 3, a CDR-H1 selected from Table 6, a CDR-H2 selected from Table 7, and a CDR-H3 selected from Table 8, where the syndecan-1 binding agent specifically binds to syndecan-1, or a portion thereof.

In certain embodiments, a syndecan-1 binding agent is an antibody, or a binding fragment thereof. In certain embodiments, a syndecan-1 binding agent is a monoclonal antibody, or binding fragment thereof. In certain embodiments, a syndecan-1 binding agent comprises a constant region of an IgG, IgD, IgE, IgA or IgM. In certain embodiments, a syndecan-1 binding agent comprises a constant region of an $IgG_1$, $IgG_2$, $IgG_3$, or $IgG_4$. In certain embodiments, a syndecan-1 binding agent is selected from a Fab, Fab', F(ab')2, Fv, Fd, single-chain Fv (scFv), disulfide-linked Fvs (sdFv), VL, VH, diabody ((VL-VH)2 or (VH-VL)2), triabody (trivalent), tetrabody (tetravalent), minibody ((scFV-CH3)2), IgGdeltaCH2, scFv-Fc, (scFv)2-Fc, and binding fragments thereof.

In some embodiments, a syndecan-1 binding agent is humanized or comprises at least one human constant region, or a portion thereof. In some embodiments, a syndecan-1 binding agent comprises one, two or at least three human or humanized framework regions.

In some embodiments, a syndecan-1 binding agent specifically binds to a human syndecan-1. In some embodiments, a syndecan-1 binding agent specifically binds to an extracellular domain of syndecan-1. In some embodiments, a syndecan-1 binding agent specifically binds human syndecan-1, or a portion thereof, with a binding affinity (KD) of 50 nM or less.

In some embodiments, a syndecan-1 binding agent specifically binds to a polypeptide comprising the amino acid sequence of $GX_1KEX_2EAX_3VLP$ (SEQ ID NO:91), wherein $X_1$, $X_2$ and $X_3$ are selected from any amino acid. In certain embodiments, $X_1$ is selected from proline, alanine, cysteine, glycine, serine, threonine, and valine, and/or $X_2$ is selected from proline, alanine, cysteine, glycine, serine, threonine, and valine, and/or $X_3$ is selected from proline, alanine, cysteine, glycine, serine, threonine, valine, methionine, leucine, isoleucine and phenylalanine. In some embodiments, a syndecan-1 binding agent specifically binds to a polypeptide comprising the amino acid sequence of AGEGPKEGEAVVLP (SEQ ID NO:89) or GPKEGEAVVLP (SEQ ID NO:90).

In some aspects, presented herein is a pharmaceutical composition comprising a syndecan-1 binding agent. In some embodiments, the pharmaceutical composition is formulated as a sterile composition suitable for intravenous administration to a mammal. In some embodiments, the pharmaceutical composition is formulated for a route of administration selected from topical, local, transdermal, cutaneous, subcutaneous, subconjunctival, intravitreal, retrobulbar, intracameral, intranasal, transmucosal, enteral, oral, sublingual, rectal, parenteral, systemic, intravenous, intra-arterial, intramuscular, intraperitoneal, intracavity, intracranial, intrauterine, intravaginal, and intravesical infusion.

Certain aspects of the technology are described further in the following description, examples, claims and drawings.

BRIEF DESCRIPTION OF DRAWINGS

The drawings illustrate embodiments of the technology and are not limiting. For clarity and ease of illustration, the drawings are not made to scale and, in some instances, various aspects may be shown exaggerated or enlarged to facilitate an understanding of particular embodiments.

FIG. 1 shows an alignment of CD138 proteins derived from human, cynomolgus monkey (cyno) and mouse. Peptides used for immunization were derived from the boxed areas.

FIG. 3 shows the results of kinetic binding analysis (i.e., a SPR sonogram) for a representative hybridoma (i.e., F12P16F6) for binding to human CD138 (top panel) at 167 nM (L1A1) to 10.4 nM (L1A4).

FIG. 5A shows the humanized heavy chains compared to those of the parent F12P16F6 (P16F6). The designation cdr indicates the CDR grafting approach, the designation abb indicates the Grafting of abbreviated CDRs approach, the designation sdr indicates the SDR-transfer approach, the designation fra indicates The Frankenstein approach, and the designation ven indicates the Veneering approach. The designation repair indicates that the variable regions were subjected to a second round of humanization.

FIG. 5B shows the humanized light chains compared to those of the parent F12P16F6 (P16F6). The designations cdr, abb, sdr, fra, ven and repair indicate the same approach as FIG. 5A.

FIG. 6 shows a picture of an SDS-PAGE gel ran under reducing conditions illustrating the molecular weight (kDa) and purity of 11 representative humanized antibodies. Lane 1=12P16F6 hIgG1, Lane 2=hF6 aka-rep, Lane 3=hF6 aks-rep, Lane 4=hF6 akf-rep, Lane 5=hF6 cka-rep, Lane 6=hF6 ckf-rep, Lane 7=hF6 f2ka-rep, Lane 8=hF6 f2ks-rep, Lane 9=hF6 f2kf-rep, Lane 10=hF6 f1ka-rep, Lane 11=hF6 f1ks-rep, Lane 12=hF6 f1kf-rep, and MW=molecular weight marker. Molecular weight markers are labeled to the right of the gel.

FIG. 8 shows an illustration of an X-ray crystal structure derived from a human syndecan-1 peptide in complex with an antibody Fab fragment that was solved at 1.95 Å resolution. There is one copy each of the syndecan-1 peptide and Fab per asymmetric unit. FIG. 8 illustrates the syndecan-1-Fab binding interface. The Fab Heavy chain is shown in the form of ribbon side chain carbon atoms to the left of the figure. The Fab light chain is shown in the form of ribbon side chain carbon atoms to the right of the figure. The syndecan-1 peptide carbon atoms are shown sandwiched between the Fab heavy and light chains. Certain amino acids of the syndecan-1 peptide and certain side chains of the Fab fragment are labeled with their corresponding 3-letter amino acid abbreviation and positions.

DESCRIPTION OF EMBODIMENTS

Figure 2A:
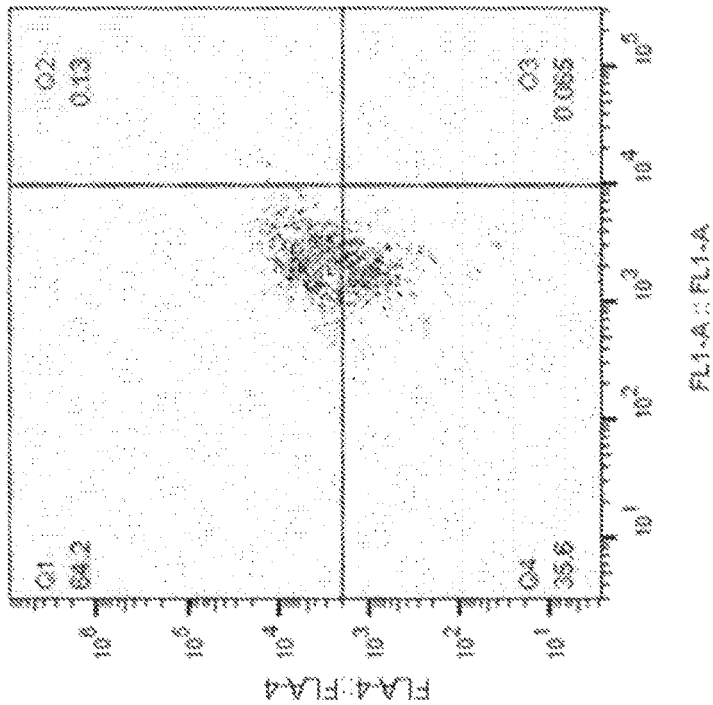
FIG. 2 shows FACS histograms for F12P16F6 (FIG. 2A) and another positive hybridoma clone F12P16G3 (FIG. 2B) binding to H929 cells.

Presented herein, in some embodiments, are monoclonal binding agents that bind syndecan-1, or a portion thereof, as well as compositions and uses thereof. Human syndecan-1 (e.g., SEQ ID NO:1) generally comprises an immature polypeptide sequence of 310 amino acids which includes an N-terminal single sequence from amino acids 1-22, an extracellular domain from about amino acid 23-254, a transmembrane domain from about amino acid 255 to 275 and a cytoplasmic domain from about amino acid 276 to 310, numbered from the N-terminus to the C-terminus. Methods of identifying leader sequences, extracellular domains, transmembrane domains, and cytoplasmic domains of a syndecan-1 receptor are known and any suitable method can be used to identify such domains or regions within a syndecan-1 polypeptide sequence derived from a suitable mammalian species.

In some embodiments syndecan-1 is a mammalian syndecan-1. A syndecan-1 may be derived from any mammalian species. In some embodiments, a synedcan-1 polypeptide is a human syndecan-1. In certain embodiments, an extracellular domain of syndecan-1 comprises an N-terminal portion of a syndecan-1 polypeptide that is typically expressed on the cell surface of an intact mammalian cell. In certain embodiments an extracellular domain of syndecan-1 is expressed in a soluble or a non-membrane bound form that lacks a cytoplasmic and/or transmembrane domain. In certain embodiments syndecan-1 and/or the extracellular domain of syndecan-1 comprises one or more amino acid additions, deletions or substitutions. A syndecan-1 polypeptide may comprise an amino acid sequence at least 80%, at least 85%, at least 90%, at least 95%, at least 98% or 100% identical to a syndecan-1 polypeptide. In certain embodiments, a syndecan-1 polypeptide comprises a portion of (e.g., a sub-sequence of) a syndecan-1 protein. In some embodiments a portion of a syndecan-1 comprises an extracellular domain of syndecan-1, or a portion thereof.

Presented herein, in some embodiments, are compositions (e.g., pharmaceutical compositions) comprising one or more binding agents that bind specifically to syndecan-1 or a portion thereof. In some embodiments binding agents presented herein are used for the treatment, prevention and/or diagnosis of a neoplastic disorder and/or a cancer in a subject.

The term "subject" refers to a mammal. Any suitable mammal can be treated by a method or composition described herein. Non-limiting examples of mammals include humans, non-human primates (e.g., apes, gibbons, chimpanzees, orangutans, monkeys, macaques, and the like), domestic animals (e.g., dogs and cats), farm animals (e.g., horses, cows, goats, sheep, and pigs) and experimental animals (e.g., mouse, rat, rabbit, and guinea pig).

In some embodiments a mammal is a human. A mammal can be any age or at any stage of development (e.g., an adult, teen, child, infant, or a mammal in utero). A mammal can be male or female. In some embodiments a subject in need is a subject who has or is suspected of having a neoplastic disorder or cancer.

In certain embodiments, a binding agent comprises or consists of one or more polypeptides or one or more proteins that bind specifically to at least one antigen (e.g., syndecan-1 or a portion thereof). A binding agent often comprises at least one antigen binding portion (i.e. a binding portion). An antigen binding portion of a binding agent is that portion that binds specifically to an antigen. In certain embodiments a binding portion of a binding agent comprises or consists of a single polypeptide (e.g., single chain antibody). In some embodiments a binding portion of a binding agent comprises or consists of two polypeptides. In some embodiments a binding portion of a binding agent comprises or consists of 2, 3, 4 or more polypeptides. In some embodiments a binding agent comprises one or more structural portions (e.g., scaffolds, structural polypeptides, constant regions and/or framework regions). In some embodiments a binding agent, or binding portion thereof is attached to a substrate (e.g., a polymer, a non-organic material, silicon, a bead, and the like).

A binding agent may comprise one antigen binding portion or multiple antigen binding portions. For example, a binding agent that comprises one binding portion is sometimes referred to as monovalent. A binding agent that comprises two binding portions is sometimes referred as divalent. In some embodiments a binding agent comprises 1, 2, 3, 4, 5, 6, 7, 8, 9, or 10 or more binding portions. In certain embodiments, all of the binding portions of a multivalent binding agent bind to the same antigen. In certain embodiments, all of the binding portions of a multivalent binding agent comprise one or more polypeptide sequences that are at least 90%, at least 95%, at least 99% or 100% identical.

In some embodiments a binding agent comprises an antibody, or a portion thereof (e.g., a binding portion thereof). In certain embodiments, a binding agent comprises or consists of an antibody, an antibody fragment and/or an antigen binding portion of an antibody (e.g., a binding fragment, i.e., a binding portion thereof). In some embodiments a binding agent is an antibody (e.g., a monoclonal antibody and/or a recombinant antibody). A binding agent or antibody can be generated, manufactured or produced by a suitable method. In some embodiments a binding agent is monoclonal. In some embodiments a binding agent is a monoclonal antibody derived from a suitable species. Certain non-limiting examples of a binding agent include monoclonal antibodies, chimeric antibodies, antibody binding fragments (e.g., an antigen binding portion of an antibody), a CDR-grafted antibody, a humanized antibody, and a human antibody, or portions thereof. Human antibodies can be obtained by any suitable method. For example, human antibodies can be obtained from trans-chromosomal animals engineered to produce fully human antibodies. In certain embodiments, a binding agent is not polyclonal, and/or is not a polyclonal antibody.

In some embodiments a binding agent is derived, produced, obtained, isolated, and/or purified from a suitable species. In some embodiments a binding agent is derived, produced, obtained, isolated, and/or purified from a rabbit, goat, horse, cow, rat, mouse, fish, bird, or llama, for example. In some embodiments a binding agent is derived, produced, obtained, isolated, and/or purified from a bird (e.g., a chicken, or a bird egg). In some embodiments a binding agent is derived, produced, obtained, isolated, and/or purified from a plant (e.g., a recombinant binding agent produced by a genetically engineered plant). In some embodiments a binding agent is derived, produced, obtained, isolated, and/or purified from a suitable mammal. In certain embodiments a suitable mammal is a genetically altered mammal (e.g., a trans-chromosomal or transgenic mammal) engineered to produce antibodies comprising human heavy chains and/or human light chains or portions thereof. In some embodiments a binding agent is produced, obtained, isolated, or purified from a prokaryotic or eukaryotic cell (e.g., a recombinant binding agent produced by a genetically engineered cell). In some embodiments a binding agent is produced, obtained, isolated, or purified from a virus (e.g., a recombinant binding agent produced by a genetically engineered virus).

A binding agent can be expressed, isolated from and/or purified from a suitable expression system non-limiting examples of which include a suitable bacteria, phage, insect, virus, plant or mammalian expression system. For example, a nucleic acid encoding a binding agent can be introduced into a suitable mammalian cell line that expresses and secretes the binding agent into the cell culture media. Any suitable mammalian cell line can be used. In certain embodiments a mammalian cell line is a Chinese hamster ovary (CHO) cell line. A method of producing a binding agent (e.g. syndecan-1 binding agent) may comprise one or more of (i) introducing one or more nucleic acids into a suitable cell line wherein the nucleic acid directs the expression of a binding agent; (ii) culturing the cell line using a suitable culturing method for a period of time that allows expression of the binding agent; (iii) harvesting the cell line (e.g., by way of generating a lysate) or harvesting conditioned media from the cell line (e.g., where the binding agent is secreted); and (iv) isolating and/or purifying the binding agent using a suitable method.

In certain embodiments, a binding agent is not found in nature and is not naturally occurring. For example, in certain embodiments, a binding agent is generated artificially in an animal by administering an emulsified cocktail that includes a foreign recombinant antigen, a powerful adjuvant, and often a mineral oil and/or a detergent, thereby inducing an artificial immune response to the foreign recombinant antigen (e.g., syndecan-1, syndecan-1-Fc).

In certain embodiments, a monoclonal antibody or a monoclonal binding agent is a substantially homogeneous population of binding agents, or binding fragments thereof, where each individual binding agent in the population is substantially identical and/or binds to the same epitope, with the exception of possible variants that may arise during production of a monoclonal binding agent. In some embodiments such variants generally are absent or may be present in minor amounts. In contrast to polyclonal antibody preparations which typically include a population of different antibodies directed against different determinants (epitopes), each binding agent of a population of monoclonal binding agents often binds a single determinant on an antigen. Monoclonal binding agents are often not contaminated by other immunoglobulins. Although one or more different monoclonal binding agents may be purposely added to a composition to form a mixture.

The modifier "monoclonal" is not to be construed as requiring production of a binding agent by any particular method. A monoclonal binding agent can be produced by any suitable method.

For example, in certain embodiments, a monoclonal antibody is made by the hybridoma method (e.g., as described by Kohler et al, Nature, 256:495 (1975)), or a variation thereof. In some embodiments a monoclonal binding agent is made by a recombinant DNA method. For example, a monoclonal binding agent can be made by screening a recombinant library using a suitable expression system (e.g., a phage display expression system). In some embodiments a monoclonal binding agent is isolated from a phage library of binding agents, for example by using a technique described in Clackson et al, Nature, 352:624-628 (1991) and/or Marks et al, J. Mol Biol, 222:581-597 (1991), or a variation thereof.

In certain embodiments, a binding agent comprises one or more structural or backbone portions, sometimes referred to as scaffolds. A binding agent may comprise a scaffold, non-limiting examples of which include a scaffold derived from an antibody, a Z domain of Protein A, gamma-B crystalline, ubiquitin, cystatin, Sac7d, a triple helix coiled coil, a lipocalin, an ankyrin repeat motif, a Kunitz domain of a suitable protease inhibitor, a fibronectin domain, a nucleic acid polymer, the like, portions thereof or combinations thereof. In some embodiments a binding agent does not comprise a scaffold. In certain embodiments, a binding agent comprises one or more structural portions of a mammalian antibody.

In certain embodiments a binding agent comprises one or more constant regions (e.g., constant regions derived from an antibody, e.g., a mammalian antibody). A binding agent may comprise any suitable constant region of an antibody, or one or more portions thereof. In certain embodiments a binding agent comprises a constant region of an antibody light chain and/or a constant region of an antibody heavy chain. In some embodiments a binding agent comprises a lambda (λ) light chain constant region, or a portion thereof. In some embodiments a binding agent comprises a kappa (κ) light chain constant region, or a portion thereof. In some embodiments a binding agent comprises a polypeptide that is at least 75%, at least 80%, at least 85%, at least 90%, at least 95% or at least 99% identical to a polypeptide sequence of a light chain constant region of a mammalian antibody, or portion thereof. In some embodiments a binding agent comprises a polypeptide that is at least 75%, at least 80%, at least 85%, at least 90%, at least 95% or at least 99% identical to a polypeptide sequence of a light chain constant region of a human antibody. In some embodiments a binding agent does not include a light chain constant region.

In certain embodiments a binding agent comprises a constant region of an antibody heavy chain. A binding agent can include any suitable heavy chain constant region, or portion thereof. In mammals, an antibody can have at least five types/classes of Ig heavy chains denoted as IgA, IgD, IgE, IgG, and IgM, which are determined by the presence of distinct heavy chain constant regions, or portion thereof (e.g., CH1, CL, CH2, CH3 domains). In some embodiments a binding agent comprises one or more heavy chain constant regions of an IgM, IgD, IgA, or IgE isotype, or a portion thereof. In some embodiments a binding agent comprises a heavy chain constant region of an $IgG_1$, $IgG_2$, $IgG_3$ or $IgG_4$, or one or more portions thereof. In some embodiments a binding agent comprises a polypeptide that is at least 75%, at least 80%, at least 85%, at least 90%, at least 95%, at least 99% identical, or 100% identical to a polypeptide sequence of a heavy chain constant region of a mammalian antibody. In some embodiments a binding agent comprises a polypeptide that is at least 75%, at least 80%, at least 85%, at least 90%, at least 95%, at least 99% identical or 100% identical to a polypeptide sequence of a heavy chain constant region of a human antibody. In some embodiments a binding agent comprises one or more additions, deletions and/or modification to a constant region. A binding agent is sometimes modified to change the antibody class, or isotype of a binding agent. In some embodiments a binding agent comprises one or more additions, deletions and/or modification (one or more amino acid substitutions, deletions or additions) to modify one or more functions of a binding agent, for example to abolish, enhance or decrease serum half-life, Fc receptor binding, complement binding (e.g., C1q binding), glycosylation, sialylation, cellular toxicity, antibody-dependent cell-mediated phagocytosis (ADCP), antibody dependent cellular cytotoxicity (ADCC), and the like. In some embodiments a binding agent does not include one or more portions of a heavy chain constant region or light chain constant region. In some embodiments a binding agent does not include a heavy chain constant region.

In some embodiments a binding agent comprises or consists of one or more variable regions of an antibody, or a portion thereof. In some embodiments a binding agent comprises one or more light chain variable regions, or a portion thereof. In some embodiments a binding agent comprises one or more heavy chain variable regions, or a portion thereof. In certain embodiments a binding agent comprises at least one light chain variable region and at least one heavy chain variable region. A light chain variable region and heavy chain variable region can be on the same or different polypeptides.

In certain embodiment, a binding agent is a non-naturally occurring binding agent. Non-limiting examples of non-naturally occurring binding agents include monoclonal binding agents (e.g., monoclonal antibodies), chimeric antibodies, CDR-grafted antibodies, humanized antibodies, single-chain antibodies, Fab, Fab', F(ab')2, Fv fragment, single-chain Fv (scFv), scFv-Fc, (scFv)2-Fc, disulfide-linked Fvs (sdFv), VL, VH, diabody (Dab), triabody (trivalent), tetrabody (tetravalent), minibody ((scFV-CH3)2), IgGdeltaCH2, synbody, fynomers, affibodies, affilins, affimers, affitins, alphabodies, anticalins, avimers, DARPins, Kunitz domain peptides, monobodies, TandAbs, nanobodies, BiTEs, SMIPs, DNLs, Duocalins, adnectins, Albu-dabs, DARTs, DVD-IG, Covx-bodies, peptibodies, scFv-Igs, SVD-Igs, dAb-Igs, Knob-in-Holes, triomAbs, the like, combinations thereof, and antigen binding portions thereof.

In some embodiments a binding agent comprises or consists of a Fab, Fab', F(ab')2, Fv fragment, single-chain Fv (scFv), diabody (Dab), synbody, the like and/or a combination or portion thereof. In some embodiments a binding agent is a Fab, Fab', F(ab')2, Fv fragment, single-chain Fv (scFv), diabody (Dab), synbody, the like and/or a combination, or portion thereof (see, e.g., U.S. Pat. Nos. 6,099,842 and 5,990,296). In some embodiments a binding agent comprises a single-chain polypeptide comprising one or more antigen binding portions. For example, a single-chain binding agent can be constructed by joining a heavy chain variable region, or antigen binding portion thereof, with a light chain variable region, or antigen binding portion thereof, with a linker (e.g., an amino acid, a polypeptide linker) using recombinant molecular biology processes. Such single chain binding agents often exhibit specificities and affinities for an antigen similar to a parent two-chain monoclonal binding agent. Binding agents often comprise engineered regions such as CDR-grafted or humanized portions. In certain embodiments a binding agent is an intact two-chain immunoglobulin, and in other embodiments a binding agent is a Fab monomer or a Fab dimer.

Nucleic acids, or portions thereof, that encode a polypeptide of a binding agent may be cloned, subcloned, rearranged or modified for recombinant expression by a suitable cloning procedure and subsequently expressed using a suitable expression system by a method known to those skilled in the art (e.g., see Maniatis et al., Molecular Cloning: A Laboratory Manual, Cold Spring Harbor Laboratory, 1982; Antibody Engineering: Methods and Protocols, Vol. 248 of Methods in molecular biology, edited by Benny K. C. Lo, Springer Science & Business Media, 2004; Antibody Engineering, Vol. 1, Roland E. Kontermann, Stefan Duebel, Edition 2, Publisher Springer Science & Business Media, 2010; Antibody Phage Display: Methods and Protocols, Biomed Protocols, Vol. 178 of Methods in molecular biology, Editors Philippa M. O'Brien, Robert Aitken, Springer Science & Business Media, 2004).

In mammals, the heavy chain variable region and light chain variable region of an antibody each contribute three CDRs (complementary determining regions) commonly referred to as CDR1, CDR2 and CDR3, that are separated and/or flanked by framework regions (e.g., FR1, FR2, FR3 and FR4). The term "CDR" as used herein refers to an amino acid sequence of a polypeptide identified as a complementary determining region. In certain embodiments, definitive delineation of a CDR polypeptide sequence and identification of residues comprising the binding site of a binding agent is accomplished by solving the structure of a binding agent and/or solving the structure of a binding agent-antigen complex. In certain embodiments, this can be accomplished by any suitable method, such as X-ray crystallography and/or computer modeling. In certain embodiments, various methods of analysis can be employed to identify or approximate the CDR sequences of a binding agent or antibody. For example, the amino acid sequence and/or location of CDRs in a polypeptide sequence of a binding agent, an antibody, a binding portion thereof or variable region thereof, can be identified using a suitable method, non-limiting examples of which include the Kabat system (e.g., see Kabat, E. A., et al., 1991; Sequences of Proteins of Immunological Interest, Fifth Edition, NIH Publication No. 91-3242, as well as Johnson, G. and Wu, T. T. 2000, Nucleic Acids Research), and/or the Chothia Numbering Scheme (e.g., Chothia & Lesk, (1987) J. Mol. Biol, 196:901-917; Chothia et al, Nature, (1989) 342:878-883; and A1-Lazikani et al., (1997) JMB 273, 927-948). In some embodiments the amino sequence and/or location of CDRs of an antibody can be identified using the AbM method and/or contact method. The "AbM" definition uses an integrated suite of computer programs produced by Oxford Molecular Group that model antibody structure (see e.g., Martin et al, Proc. Natl. Acad. Sci. (USA), 86:9268-9272 (1989); "AbM(Trademark), A Computer Program for Modeling Variable Regions of Antibodies," Oxford, UK; Oxford Molecular, Ltd.). The AbM definition models the tertiary structure of an antibody from primary sequence using a combination of knowledge databases and ab initio methods, such as those described by Samudrala et al., "Ab Initio Protein Structure Prediction Using a Combined Hierarchical Approach," in PROTEINS, Structure, Function and Genetics Suppl, 3:194-198 (1999). In certain embodiments, a contact definition is based on an analysis of the available complex crystal structures (see e.g., MacCallum et ah, J. Mol. Biol, 5:732-45 (1996)).

In some embodiments a binding agent and/or an antigen binding portion of a binding agent comprises at least 2, at least 3, at least 4, at least 5 or at least 6 CDRs. In some embodiments a binding agent comprises 3 to 60 CDRs (e.g., for binding agents having multiple antigen binding portions). In some embodiments a binding agent comprises 3 to 12 CDRs. In some embodiments an antigen binding portion of a binding agent comprises 1 to 6 CDR polypeptide sequences.

In certain embodiments, a binding agent and/or an antigen binding portion of a binding agent comprises one, two or three CDRs of a light chain variable region. In some embodiments a light chain variable region of a binding agent comprises one or more CDRs (e.g., one, two, three, or more CDRs). The amino acid sequences representing a CDR in a light chain variable region of an antibody or binding agent is referred to as CDR-L1, CDR-L2, and CDR-L3 which are numbered sequentially (i.e., L1, L2 and L3) in the direction from the amino terminus (N-terminus) to the carboxy terminus (C-terminus) of a light chain variable region. For example, in a polypeptide representing a light chain variable region of a binding agent, CDR-L1, when present, is the most N-terminal light chain CDR; CDR-L3, when present, is the most C-terminal light chain CDR; and CDR-L2, when present, is located (i) between CDR-L1 and CDR-L3, (ii) on the N-terminal side of CDR-L3 or (iii) on the C-terminal side of CDR-L1, of a light chain variable region or binding portion of a binding agent. The terms "CDR-L1", "CDR-L2" and "CDR-L3" refer to, in part, an amino acid sequence of a polypeptide identified as, or disclosed herein as, a complementary determining region of a binding agent (e.g., a CDR of a light chain variable region). Non-limiting examples of amino acid sequences of a CDR-L1, CDR-L2 and CDR-L3 are provided in Tables 1-3, respectively. A light chain variable region or antigen binding portion of a binding agent described herein may comprise any combination of a CDR-L1, a CDR-L2, and a CDR-L3 disclosed herein, wherein the binding agent retains specific binding to syndecan-1, or a portion thereof. In certain embodiments, a light chain variable region or antigen binding portion of a binding agent described herein comprises a single light chain CDR comprising an amino acid sequence at least 70% identical to a CDR-L3 selected from Table 3. In certain embodiments, a light chain variable region or antigen binding portion of a binding agent described herein comprises an amino acid sequence at least 70% identical to a CDR-L3 selected from Table 3, and any other suitable CDR-L2 and/or CDR-L1 polypeptide sequence, where the binding agent retains specific binding to syndecan-1, or a portion thereof. In certain embodiments, the light chain CDRs of a light chain variable region or antigen binding portion of a binding agent consists of a CDR-L3 and a CDR-L2, where the CDR-L3 comprises an amino acid sequence at least 70% identical to a CDR-L3 selected from Table 3 and the CDR-L2 comprises an amino acid sequence at least 70% identical to a CDR-L2 selected from Table 2. In certain embodiments, a light chain variable region or antigen binding portion of a binding agent described herein comprises an amino acid sequence at least 70% identical to a CDR-L3 selected from Table 3 and an amino acid sequence at least 70% identical to a CDR-L2 selected from Table 2, and any other suitable CDR-L1 polypeptide sequence, where the binding agent retains specific binding to syndecan-1, or a portion thereof. In certain embodiments, a light chain variable region or antigen binding portion of a binding agent described herein comprises three light chain CDRs consisting of an amino acid sequence at least 70% identical to a CDR-L3 selected from Table 3, an amino acid sequence at least 70% identical to a CDR-L2 selected from Table 2 and an amino acid sequence selected at least 70% identical to a CDR-L1 of Table 1. In certain embodiments, a light chain variable region or antigen binding portion of a binding agent described herein comprises an amino acid sequence at least 70% identical to a CDR-L3 selected from Table 3, an amino acid sequence at least 70% identical to a CDR-L2 selected from Table 2 and an amino acid sequence at least 70% identical to a CDR-L1 selected from Table 1, where the binding agent retains specific binding to syndecan-1, or a portion thereof.

In some embodiments a binding agent comprises one or more light chain CDRs that are at least 70%, 75%, 85%, 86%, 87%, 88%, 89%, 90%, 91%, 92%, 93%, 94%, 95%, 96%, 97%, 98%, or at least 99% identical to any one of the CDR sequences listed in Tables 1, 2 or 3. In some embodiments a binding agent or the antigen binding portion of a binding agent comprises a CDR-L1 that is at least 700, 750, 850, 860, 87%, 88%, 890, 900, 910, 920, 930, 94%, 95%, 96%, 97%, 98%, or at least 99% identical to any one of the sequences shown in Table 1. In some embodiments a binding agent or the antigen binding portion of a binding agent comprises a CDR-L1 of any one of the sequences shown in Table 1.

TABLE 1

CDR-L1 Sequences

| SEQ ID | Hybridoma Clone/ Antibody Name | Amino Acid Sequence |
|---|---|---|
| SEQ ID NO: 2 | F12P16F6 | KSSQSLLASDGKTYLN |
| SEQ ID NO: 3 | F12P16F6 | QSLLASDGKTY |
| SEQ ID NO: 4 | F13P30A7 | KASENVGNYVS |
| SEQ ID NO: 5 | F13P30A7 | ENVGNY |
| SEQ ID NO: 6 | F13P18D8 | KASENVGTYVS |
| SEQ ID NO: 7 | F13P18D8 | ASENVGTY |
| SEQ ID NO: 8 | F12P7G11 | RASSSVMYMH |
| SEQ ID NO: 9 | F12F7G11 | ASSSVNY |
| SEQ ID NO: 10 | F13P14D3 | KASENVGSYVS |
| SEQ ID NO: 11 | F13P14D3 | ASENVGSY |
| SEQ ID NO: 12 | F11AP11E5 | KSGQSLLYSNGKTYLT |
| SEQ ID NO: 13 | F11AP11E5 | KSGQSLLYSNG |
| SEQ ID NO: 14 | F12P18D4.a | KSSQSLLYSNGKTYLN |
| SEQ ID NO: 15 | F12P18D4.a | KSSQSLLYSNG |

In some embodiments a syndecan-1 binding agent or the antigen binding portion of a syndecan-1 binding agent comprises a CDR-L2 that is at least 70%, 75%, 85%, 86%, 87%, 88%, 89%, 90%, 91%, 92%, 93%, 94%, 95%, 96%, 97%, 98%, or at least 99% identical to any one of the sequences shown in Table 2. In some embodiments a syndecan-1 binding agent or the antigen binding portion of a syndecan-1 binding agent comprises a CDR-L2 of any one of the sequences shown in Table 2.

TABLE 2

CDR-L2 Sequences

| SEQ ID | Hybridoma Clone/ Antibody Name | Amino Acid Sequence |
|---|---|---|
| SEQ ID NO: 16 | F12P16F6 | YDVSKLDS |
| SEQ ID NO: 17 | F12P16F6 | LVSKLDS |
| SEQ ID NO: 18 | F12P16F6 | LVSKLD |
| SEQ ID NO: 19 | F13P30A7 | YGASYRYT |
| SEQ ID NO: 20 | F13P3QA7 | GASYRYT |
| SEQ ID NO: 21 | F13P30A7 | GASYRY |
| SEQ ID NO: 22 | F13P18D8 | GASNRYT |
| SEQ ID NO: 23 | F12P7G11 | ATSYLAS |
| SEQ ID NO: 24 | F13P14D3 | GASNRNT |
| SEQ ID NO: 25 | F11AP11E5 | QVSKLDP |
| SEQ ID NO: 26 | F12P1SD4.a | LVSKVDS |

In some embodiments a syndecan-1 binding agent or the antigen binding portion of a syndecan-1 binding agent comprises a CDR-L3 that is at least 70%, 75%, 85%, 86%, 87%, 88%, 89%, 90%, 91%, 92%, 93%, 94%, 95%, 96%, 97%, 98%, or at least 99% identical to any one of the sequences shown in Table 3. In some embodiments a syndecan-1 binding agent or the antigen binding portion of a syndecan-1 binding agent comprises a CDR-L3 of any one of the sequences shown in Table 3.

TABLE 3

CDR-L3 Sequences

| SEQ ID | Hybridoma Clone/ Antibody Name | Amino Acid Sequence |
|---|---|---|
| SEQ ID NO: 27 | F12P16F6 | WQGAHFPFT |
| SEQ ID NO: 28 | F12P16F6 | QGAHFPF |
| SEQ ID NO: 29 | F13P30A7/ F13P14D3 | GQSSRYPLT |
| SEQ ID NO: 30 | F13P30A7/ F13P14D3 | QSSRYPL |
| SEQ ID NO: 31 | F13P18D8 | GQSSRYPLT |
| SEQ ID NO: 32 | F12P7G11 | QQWSSDPLT |
| SEQ ID NO: 33 | F11AP11E5 | LQNTYYPHT |
| SEQ ID NO: 34 | F12P18D4.a | VQGTHFPLT |

In some embodiments a syndecan-1 binding agent or the antigen binding portion of a syndecan-1 binding agent comprises a light chain variable region having at least 70%, 75%, 85%, 86%, 87%, 88%, 890, 900, 910, 92%, 93%, 94%, 950, 960, 970, 980, or at least 99% identity to an amino acid sequence of Table 4. In some embodiments a syndecan-1 binding agent or the antigen binding portion of a syndecan-1 binding agent comprises a light chain variable region sequence of Table 4.

TABLE 4

VARIABLE LIGHT CHAIN SEQUENCES

| SEQ ID | Hybridoma Clone/ Antibody Name | Amino Acid Sequence |
|---|---|---|
| SEQ ID NO: 35 | F12P16F0 | DVVMTQTPLTLSVTIGQPASISCKSSQSLLASDGKTYLNWLLQ RPGQSPKRLIYLVSKLDSGVPDRFTGSGSGTGFTLQISRVEAE DLGIYYCWQGAHFPFTFGSGTKLEIKR |

TABLE 4-continued

VARIABLE LIGHT CHAIN SEQUENCES

| SEQ ID | Hybridoma Clone/ Antibody Name | Amino Acid Sequence |
|---|---|---|
| SEQ ID NO: 36 | F13P30A7 | NIIMTQSPKSMAMSVGERVTLSCKASENVGNYVSWYQQKPEQS PKLLIYGASYRYTGVPDRFTGSGSGTDFTLTISSVQAEDLADY HCGQSSRYPLTFGAGTKLELKR |
| SEQ ID NO: 37 | F13P18D8 | NIVMTQSPKSMSMSVGERVTLSCKASENVGTYVSWYQQKSDQS PKLLIYGASNRYTGVPDRFTGSGSATDFTLTITSVQSEDLADY HCGQSSRYPLTFGAGTKLELKR |
| SEQ ID NO: 38 | F12P7G11 | QIVLSQSPAILSASPGEKVTMTCRASSSVNYMHWYQQKPGSSP KHWIYATSYLASGVPARFSGSGSGTSYSLTISRVEAEDAATYY CQQWSSDPLTFGAGTKLELKR |
| SEQ ID NO: 39 | F13P14D3 | NIVMTQSPKSMSMSVGQRVTLSCKASENVGSYVSWYQQKPEQS PKLLIYGASNRNTGVPDRFTGSGSATDFTLTISSVQAEDLADY HCGQSSRYPLTFGGGTKLELKR |
| SEQ ID NO: 40 | F11AP11E5 | DVVMTQTPLSLSVTIGQPASISCKSGQSLLYSNGKTYLTWLQQ RPGQAPKLLMYQVSKLDPGIPDRFSGSGSETDFTLKISRVEAE DLGVYYCLQNTYYPHTFGAGTKLELKR |
| SEQ ID NO: 41 | F12P18D4.a | DVVMTQTPLTLSVTIGQSASISCKSSQSLLYSNGKTYLNWLLQ RPGQSPKRLIYLVSKVDSGVPDRFTGSGSGTDFTLSISRVEAE DLGVYYCVQGTHFPLTFGVGTKLELKR |

In some embodiments a syndecan-1 binding agent or the antigen binding portion of a syndecan-1 binding agent comprises a humanized light chain variable region having at least 70%, 75%, 85%, 860, 870, 88%, 890, 900, 910, 920, 930, 94%, 950, 960, 97%, 98%, or at least 99% identity to a sequence of Table 5. In some embodiments a syndecan-1 binding agent or the antigen binding portion of a syndecan-1 binding agent comprises a humanized light chain variable region sequence of Table 5.

CDR-H3, which are numbered sequentially (i.e., H1, H2 and H3) in the direction from the amino terminus (N-terminus) to the carboxy terminus (C-terminus) of a heavy chain variable region. For example, in a polypeptide representing a heavy chain variable region of a syndecan-1 binding agent, CDR-H1, when present, is the most N-terminal CDR; CDR-H3, when present, is the most C-terminal CDR; and CDR-H2, when present, is located (i) between CDR-H1 and CDR-H3, (ii) on the N-terminal side of CDR-H3 or (iii) on

TABLE 5

Humanzied Light Chains Variable Regions

| SEQ ID | Humanized Light Chain Name | Light Chains Variable Region Amino Acid Sequence |
|---|---|---|
| SEQ ID NO: 42 | P16F6 sdr/cdr/ ven-rep | DVVMTQTPLSLSVTPGQPASISCKSSQSLLASDGKTYLNWLL QRPGQSPKRLIYLVSKLDSGVPNRFSGSGSGTDFTLQISRVE AEDVGLYYCWQGAHFPFTFGSGTKLEIKR |
| SEQ ID NO: 43 | P16F6 abb-rep | DVVMTQTPLSLSVTPGQPASISCKSSQSLLASDGKTYLNWLL QRPGQSPKRLIYLVSKLDSGVPNRFSGSGSGTDFTLQISRVE AEDVGLYYCMQGAHFPFTFGGGTKVEIKR |
| SEQ ID NO: 44 | P16F6 fra-rep | DVVMTQSPLSLSVTLGQPASISCKSSQSLLASDGKTYLNWLQ QRPGQSPRRLIYLVSKLDSGVPNRFSGSGSGTDFTLQISRVE AEDVGLYYCWQGAHFPFTFGSGTKLEIKR |
| SEQ ID NO: 45 | P16F6 sdr/cdr/ ven-rep (Final) | DVVMTQTPLSLSVTPGQPASISCKSSQSLLASDGKTYLNWLL QRPGQSPKRLIYLVSKLDSGVPNRFSGSGSGTDFTLQISRVE AEDVGLYYCWQGAHFPFTFGSGTKLEIKRTVAAPSVFIFPPS DEQLKSGTASVVCLLNNFYPREAKVQWKVDNALQSGNSQESV TEQDSKDSTYSLSSTLTLSKADYEKHKVYACEVTHQGLSSPV TKSFNRGEC |

In certain embodiments, a syndecan-1 binding agent and/or an antigen binding portion of a syndecan-1 binding agent comprises one, two or three CDRs of a heavy chain variable region. In some embodiments a heavy chain variable region comprises one or more CDRs (e.g., one, two, three, or more CDRs). The amino acid sequences representing a CDR in a heavy chain variable region of an antibody or binding agent is referred to as CDR-H1, CDR-H2, and the C-terminal side of CDR-H, of a heavy chain variable region. The terms "CDR-H1", "CDR-H2" and "CDR-H3" refer to, in part, an amino acid sequence of a polypeptide identified as, or disclosed herein as, a complementary determining region of a syndecan-1 binding agent (e.g., a CDR of a heavy chain variable region of a syndecan-1 binding agent). Non-limiting examples of amino acid sequences of a CDR-H1, CDR-H2 and CDR-H3 are provided in Tables 6-8, respectively. A heavy chain variable region or antigen binding portion of a syndecan-1 binding agent described herein may comprise any combination of a CDR-H1, a CDR-H2, and a CDR-H3 disclosed herein where The syndecan-1 binding agent retains specific binding to syndecan-1, or a portion thereof. In certain embodiments, a heavy chain variable region or antigen binding portion of a syndecan-1 binding agent described herein comprises a single heavy chain CDR consisting of an amino acid sequence at least 70% identical to a CDR-H3 selected from Table 8. In certain embodiments, a heavy chain variable region or antigen binding portion of a syndecan-1 binding agent described herein comprises an amino acid sequence at least 70% identical to a CDR-H3 selected from Table 8, and any other suitable CDR-H2 and/or CDR-H1 polypeptide sequence, where The syndecan-1 binding agent retains specific binding to syndecan-1, or a portion thereof. In certain embodiments, the heavy chain CDRs of a heavy chain variable region or antigen binding portion of a syndecan-1 binding agent consists of a CDR-H3 and a CDR-H2, where the CDR-H3 comprises an amino acid sequence at least 70% identical to a CDR-H3 selected from Table 8 and the CDR-H2 comprises an amino acid sequence at least 70% identical to a CDR-H2 selected from Table 7. In certain embodiments, a heavy chain variable region or antigen binding portion of a syndecan-1 binding agent described herein comprises an amino acid sequence at least 70% identical to a CDR-H3 selected from Table 8 and an amino acid sequence at least 70% identical to a CDR-H2 selected from Table 7, and any other suitable CDR-H1 polypeptide sequence, where The syndecan-1 binding agent retains specific binding to syndecan-1 or a portion thereof. In certain embodiments, a heavy chain variable region or antigen binding portion of a syndecan-1 binding agent described herein comprises three heavy chain CDRs consisting of an amino acid sequence at least 70% identical to a CDR-H3 selected from Table 8, an amino acid sequence at least 70% identical to a CDR-H2 selected from Table 7 and an amino acid sequence selected at least 70% identical to a CDR-H1 of Table 6. In certain embodiments, a heavy chain variable region or antigen binding portion of a syndecan-1 binding agent described herein comprises an amino acid sequence at least 70% identical to a CDR-H3 selected from Table 8, an amino acid sequence at least 70% identical to a CDR-H2 selected from Table 7 and an amino acid sequence at least 70% identical to a CDR-H1 selected from Table 6, where The syndecan-1 binding agent retains specific binding to syndecan-1, or a portion thereof.

In some embodiments a syndecan-1 binding agent comprises one or more heavy chain CDRs with at least 70%, 75%, 85%, 86%, 87%, 88%, 89%, 90%, 91%, 92%, 93%, 94%, 95%, 96%, 97%, 98%, or at least 99% identity to any one of the CDRs of Tables 6, 7 or 8. In some embodiments a syndecan-1 binding agent or the antigen binding portion of a syndecan-1 binding agent comprises a CDR-H1 that is at least 70%, 75%, 85%, 86%, 87%, 88%, 89%, 90%, 91%, 92%, 93%, 94%, 95%, 96%, 97%, 98%, or at least 99% identical to any one of the sequences shown in Table 6. In some embodiments a syndecan-1 binding agent or the antigen binding portion of a syndecan-1 binding agent comprises a CDR-H1 of any one of the sequences shown in Table 6.

TABLE 6

CDR-H1 Sequences

| SEQ ID | Hybridoma Clone/ Antibody Name | Amino Acid Sequence |
| --- | --- | --- |
| SEQ ID NO: 46 | F12P16F6 | KASGYTFTSYYLY |
| SEQ ID NO: 47 | F12F16F6 | GYTFTSYYLY |
| SEQ ID NO: 48 | F13P30A7 | AASGFTFNTYAMN |
| SEQ ID NO: 49 | F13P30A7 | ASGFTFNTYAM |
| SEQ ID NO: 50 | F13P18D8 | GFAFNTYAMN |
| SEQ ID NO: 51 | F12P7G11 | GYTFSSHWHQ |
| SEQ ID NO: 52 | F13P14D3 | GFTFNTYAMN |
| SEQ ID NO: 53 | F11AP11E5 | KASGYTFTNYYMY |
| SEQ ID NO: 54 | F12P18D4.a | YTFAD |
| SEQ ID NO: 55 | F12P18D4.a | YTFADYYMK |

In some embodiments a syndecan-1 binding agent or the antigen binding portion of a syndecan-1 binding agent comprises a CDR-H2 that is at least 70%, 75%, 85%, 86%, 87%, 88%, 89%, 90%, 91%, 92%, 93%, 94%, 95%, 96%, 97%, 98%, or at least 99% identical to any one of the sequences shown in Table 7. In some embodiments a syndecan-1 binding agent or the antigen binding portion of a syndecan-1 binding agent comprises a CDR-H2 of any one of the sequences shown in Table 7.

TABLE 7

HDR-H2 Sequences

| SEQ ID | Hybridoma Clone/ Antibody Name | Amino Acid Sequence |
| --- | --- | --- |
| SEQ ID NO: 56 | F12P16F6 | EIYPRSGGTN |
| SEQ ID NO: 57 | F12P16F6 | EIYPRSGGTNINEKFLS |
| SEQ ID NO: 58 | F13P30A7, F13P18D8, F13P14D3 | RIRSKSNNYATY |
| SEQ ID NO: 59 | F13P30A7, F13P18D3 | RIRSKSNNYATYYADSVKD |
| SEQ ID NO: 60 | F13P30A7, F13P18D8, F13P14D3 | IRSKSNNYATY |
| SEQ ID NO: 61 | F12P7G11 | AIYPGDGDTRFTQKFKG |
| SEQ ID NO: 62 | F12P7G11 | YPGDGDTRFTQK |
| SEQ ID NO: 63 | F13P14D3 | RIRSKSNNYATYYVDSVKD |
| SEQ ID NO: 64 | F11AP11E5 | EINPGNGGTNFNEKFKN |
| SEQ ID NO: 65 | F11AP11E5 | NPGNGGTNFNEKF |
| SEQ ID NO: 66 | F12P18D4.a | DINPNSGDTF |
| SEQ ID NO: 67 | F12P18D4.a | DINPNSGDTFYNHKFKG |

In some embodiments a syndecan-1 binding agent or the antigen binding portion of a syndecan-1 binding agent comprises a CDR-H3 that is at least 70%, 75%, 85%, 86%, 87%, 88%, 89%, 90%, 91%, 92%, 93%, 94%, 95%, 96%, 97%, 98%, or at least 99% identical to any one of the sequences shown in Table 8. In some embodiments a syndecan-1 binding agent or the antigen binding portion of a syndecan-1 binding agent comprises a CDR-H3 of any one of the sequences shown in Table 8.

TABLR 8

CDR-H3 Sequences

| SEQ ID | Hybridoma Clone/ Antibody Name | Amino Acid Sequence |
| --- | --- | --- |
| SEQ ID NO: 68 | F12P16F6 | TRSLLY |
| SEQ ID NO: 69 | F12P16F6 | SLLY |
| SEQ ID NO: 70 | F13P30A7 | VTDYGYVYFDA |
| SEQ ID NO: 71 | F13P30A7 | DYGYVYFDA |
| SEQ ID NO: 72 | F13P18D8 | DYYYVYFDV |
| SEQ ID NO: 73 | F12P7G11 | GIYYDRSRAMDY |

TABLR 8-continued

CDR-H3 Sequences

| SEQ ID | Hybridoma Clone/ Antibody Name | Amino Acid Sequence |
| --- | --- | --- |
| SEQ ID NO: 74 | F13P14D3 | VTDYGHVYFDV |
| SEQ ID NO: 75 | F11P11E5 | RFAY |
| SEQ ID NO: 76 | F12P1SD4.a | TYYDY |

In some embodiments a syndecan-1 binding agent or the antigen binding portion of a syndecan-1 binding agent comprises a heavy chain variable region having at least 70%, 75%, 85%, 86%, 87%, 88%, 890, 900, 910, 92%, 93%, 94%, 950, 960, 970, 980, or at least 99% identity to a sequence of Table 9. In some embodiments a syndecan-1 binding agent or the antigen binding portion of a syndecan-1 binding agent comprises a heavy chain variable region sequence of Table 9.

TABLE 9

VARIABLE HEAVY CHAIN SEQUENCES

| SEQ ID | Hybridoma Clone/ Antibody Name | Amino Acid Sequence |
| --- | --- | --- |
| SEQ ID NO: 77 | F12P16F6 | QVQLQQSGAEVVKPGASVKLSCKASGYTFTSYYLYWVKKGPG QGLDWIGEIYPRSGGTNINEKFLSKATLTADESSSTAYLQLS SLTSEDSAVYYCTRSLLYWGQGTTLIVSS |
| SEQ ID NO: 78 | P13P30A7 | EVQLVESGGGLVQPKGSLKLSCAASGFTFNTYAMNWVRQAPG KGLEWIARIRSKSNNYATYYADSVKDRFTISRDDSQSLLYLQ MNNLKTEDTAIFYCVTDYGYVYFDAWGAGTTVTVSS |
| SEQ ID NO: 79 | F13P18D8 | EVQLLSSGGGLVQPEGSLKLSCAASGFAFNTYAMNWVRQAPG KGLEWLARIRSKSNNYATYYADSVKDRFTISRDDSQGMLYLQ MNNLKTEDTAMYYCVTDYYYVYFDVWGAGTTVTVSS |
| SEQ ID NO: 80 | F12P7G11 | QVQLQQSGAELARPGASVKLSCKASGYTFSSHWMQWVKQRPG QGLEWIGAIYPGDGDTRFTQKFKGKATLTADKSSNTAYMQLS SLASEDSAVYYCARGIYYDRSRAMDYNGQGTSVTVSS |
| SEQ ID NO: 81 | F13P14D3 | EVQLVESGGGLVQPKGSLKLSCATSGFTFNTYAMNWVRQAPG KGLEWVARIRSKSNNYATYYVDSVKDRFTISRDDSQSTVHLQ MNNLKTEDTAIYYCVTDYGHVYFDVHGAGTTVTVSS |
| SEQ ID NO: 82 | F11AP11E5 | QVQLQQSGAELVKPGASVKLSCKASGYTFTNYYMYWVKQRPG QGLEWIGEINPGNGGTNFNEKFKNKATLTVDKSSSTAYMQLS SLTSEDSAVYYCTTRFAYWGQGTLVIVSA |
| SEQ ID NO: 83 | F12P18B4.a | EVQLQQSGPELVKPGASVKMSCKASGYTFADYYMKWVKQSHG KSLEWIGDINPNSGDTFYNHKFKGKATLTVDKSSSTAYMQLN SLTSEDSAVYYCARTYYDYWGQGTTLTVSS |

In some embodiments a syndecan-1 binding agent or the antigen binding portion of a syndecan-1 binding agent comprises a humanized heavy chain variable region having at least 70%, 75%, 85%, 860, 870, 88%, 890, 900, 910, 920, 930, 94%, 950, 960, 97%, 98%, or at least 99% identity to a sequence of Table 10. In some embodiments a syndecan-1 binding agent or the antigen binding portion of a syndecan-1 binding agent comprises a humanized heavy chain variable region sequence of Table 10.

TABLE 10

Humanized Heavy Chains

| SEQ ID | Heavy Chain Name | Heavy Chain Variable Region Amino Acid Sequence |
|---|---|---|
| SEQ ID NO: 84 | P16F6 abb/sdr-rep | QVQLVQSGAEVVKPGASVKLSCKASGYTFTSYYLYWVKKAPGQGL DWIGEIYPRSGGTNYAEKFQGRVTLTADTSTSTAYLELSSLTSED TAVYYCTRSLLYWGQGTTLTVSS |
| SEQ ID NO: 85 | P16F6 cdr/ven-rep | QVQLVQSGAEVVKPGASVKLSCKASGYTFTSYYLYWVKKAPGQGL DWIGEIYPRSGGTNINEKFLSRVTLTADTSTSTAYLELSSLTSED TAVYYCTRSLLYWGQGTTLTVSS |
| SEQ ID NO: 86 | P16F6 fra1-rep | QVQLQQSGAEVVKPGASVKLSCKASGYTFTSYYLYWVKKAPGQGL DWIGEIYPRSGGTNINEKFLSRVTLTADTSTSTAYMDLSSLTSED TAVYYCTRSLLYWGQGTTLTVSS |
| SEQ ID NO: 87 | P16F6 fra2-rep | QVQLQQSGAEVVKPGASVKLSCKASGYTFTSYYLYWVKKAPGQGL DWIGEIYPRSGGTNINEKFLSRVTITADESTSTVYMQLSSLTSED SAVYYCTRSLLYWGQGTTLTVSS |
| SEQ ID NO: 88 | P16F6 cdr/ven-rep (final) | QVQLVQSGAEVVKPGASVKLSCKASGYTFTSYYLYWVKKAPGQGL DWIGEIYPRSGGTNINEKFLSRVTLTADTSTSTAYLELSSLTSED TAVYYCTRSLLYWGQGTTLTVSSASTKGPSVFPLAPSSKSTSGGT AALGCLVKDYFPEPVTVSWNSGALTSGVHTFPAVLQSSGLYSLSS VVTVPSSSLGTQTYICNVNHKPSNTKVDKKVEPKSCDKTHTCPPC PAPELLGGPSVFLFPPKPKDTLMISRTPEVTCVVVDVSHEDPEVK FNWYVDGVEVHNAKTKPREEQYNSTYRVVSVLTVLHQDWLNGKEY KCKVSNKALPAPIEKTISKAKGQPREPQVYTLPPSEEEMTKNQVS LTCLVKGFYPSDIAVEWESNGQPENNYKTTPPVLDSDGSFFLYSK LTVDKSRWQQGNVFSCSVMHEALHNHYTQKSLSLSPGK |

In some embodiments a binding agent, or an antigen binding portion of a binding agent, comprises, or consists of, a CDR-L3 comprising an amino acid sequence at least 70%, at least 75%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identical to any one of the amino acid sequences of SEQ ID NOs: 27 to 34 (e.g., a CDR-L3 sequence selected from Table 3) and a CDR-H3 comprising an amino acid sequence at least 70%, at least 75%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identical to any one of the amino acid sequences of SEQ ID NOs: 68 to 76 (e.g., a CDR-H3 sequence selected from Table 8). In some embodiments a binding agent, or an antigen binding portion of a binding agent, comprises a CDR-L3 comprising an amino acid sequence at least 70%, at least 90%, at least 95%, at least 98%, at least 99% or 100% identical to the amino acid sequence of SEQ ID NO:27, 28, 29 or 30, and a CDR-H3 comprising an amino acid sequence at least 70%, at least 90%, at least 95%, at least 98%, at least 99% or 100% identical to the amino acid sequence of SEQ ID NO:68, 69, 70 or 71.

In some embodiments a binding agent, or an antigen binding portion of a binding agent, comprises, or consists of, a CDR-L3 comprising an amino acid sequence at least 70%, at least 90%, or 100% identical to any one of the amino acid sequences of SEQ ID NOs: 27 to 34 (e.g., a CDR-L3 sequence selected from Table 3), a CDR-L2 comprising an amino acid sequence at least 70%, at least 90%, or 100% identical to any one of the amino acid sequences of SEQ ID NOs: 16 to 26 (e.g., a CDR-L2 sequence selected from Table 2), a CDR-H3 comprising an amino acid sequence at least 70%, at least 90%, or 100% identical to any one of the amino acid sequences of SEQ ID NOs: 68 to 76 (e.g., a CDR-H3 sequence selected from Table 8) and a CDR-H2 comprising an amino acid sequence at least 70%, at least 90%, or 100% identical to any one of the amino acid sequences of SEQ ID NOs: 56 to 67 (e.g., a CDR-H2 sequence selected from Table 7). In some embodiments a binding agent, or an antigen binding portion of a binding agent, comprises a CDR-L3 comprising an amino acid sequence at least 70%, at least 90%, or 100% identical to the amino acid sequence of SEQ ID NO:27 or 29, a CDR-L2 comprising an amino acid sequence at least 70%, at least 90%, or 100% identical to the amino acid sequence of SEQ ID NO:16 or 19, a CDR-H3 comprising an amino acid sequence at least 70%, at least 90%, or 100% identical to the amino acid sequence of SEQ ID NO:68 or 70 and a CDR-H2 comprising an amino acid sequence at least 70%, at least 90%, or 100% identical to the amino acid sequence of SEQ ID NO:56 or 58.

In some embodiments a binding agent, or an antigen binding portion of a binding agent, comprises, or consists of, a CDR-L3 comprising an amino acid sequence at least 70%, at least 90%, or 100% identical to any one of the amino acid sequences of SEQ ID NOs: 27 to 34 (e.g., a CDR-L3 sequence selected from Table 3), a CDR-L2 comprising an amino acid sequence at least 70%, at least 90%, or 100% identical to any one of the amino acid sequences of SEQ ID NOs: 16 to 26 (e.g., a CDR-L2 sequence selected from Table 2), a CDR-L1 comprising an amino acid sequence at least 70%, at least 90%, or 100% identical to any one of the amino acid sequences of SEQ ID NOs: 2 to 15 (e.g., a CDR-L1 sequence selected from Table 1), a CDR-H3 comprising an amino acid sequence at least 70%, at least 90%, or 100% identical to any one of the amino acid sequences of SEQ ID NOs: 68 to 76 (e.g., a CDR-H3 sequence selected from Table 8), a CDR-H2 comprising an amino acid sequence at least 70%, at least 90%, or 100% identical to any one of the amino acid sequences of SEQ ID NOs: 56 to 67 (e.g., a CDR-H2 sequence selected from Table 7), and a CDR-H1 comprising an amino acid sequence at least 70%, at least 90%, or 100% identical to any one of the amino acid sequences of SEQ ID NOs: 46 to 55 (e.g., a CDR-H1 sequence selected from Table 6). In some embodiments a binding agent, or an antigen binding portion of a binding agent, comprises a CDR-L3 comprising an amino acid sequence at least 70%, at least 90%, or 100% identical to the amino acid sequence of SEQ ID NOs: 27 or 29, a CDR-L2 comprising an amino acid sequence at least 70%, at least 90%, or 100% identical to the amino acid sequence of SEQ ID NO:16 or 19, a CDR-L1 comprising an amino acid sequence at least 70%, at least 90%, or 100% identical to the amino acid sequence of SEQ ID NO:2 or 5, a CDR-H3 comprising an amino acid sequence at least 70%, at least 90%, or 100% identical to the amino acid sequence of SEQ ID NO:68 or 70, a CDR-H2 comprising an amino acid sequence at least 70%, at least 90%, or 100% identical to the amino acid sequence of SEQ ID NO:56 or 58, and a CDR-H1 comprising an amino acid sequence at least 70%, at least 90%, or 100% identical to the amino acid sequence of SEQ ID NO:46 or 48.

In some embodiments, a binding agent, or an antigen binding portion of a binding agent, comprises, or consists of, a CDR-L1 comprising an amino acid sequence at least 95%, at least 96%, at least 97%, at least 98%, at least 99% or 100% identical to any one of the amino acid sequences of SEQ ID NOs: 2 or 3; a CDR-L2 comprising an amino acid sequence at least 95%, at least 96%, at least 97%, at least 98%, at least 99% or 100% identical to any one of the amino acid sequences of SEQ ID NOs: 16, 17 or 18; and a CDR-L3 comprising an amino acid sequence at least 95%, at least 96%, at least 97%, at least 98%, at least 99% or 100% identical to any one of the amino acid sequences of SEQ ID NOs: 27 or 28.

In some embodiments, a binding agent, or an antigen binding portion of a binding agent, comprises, or consists of, a CDR-L1 comprising an amino acid sequence at least 95%, at least 96%, at least 97%, at least 98%, at least 99% or 100% identical to any one of the amino acid sequences of SEQ ID NOs: 4 or 5; a CDR-L2 comprising an amino acid sequence at least 95%, at least 96%, at least 97%, at least 98%, at least 99% or 100% identical to any one of the amino acid sequences of SEQ ID NOs: 19, 20 or 21; and a CDR-L3 comprising an amino acid sequence at least 95%, at least 96%, at least 97%, at least 98%, at least 99% or 100% identical to any one of the amino acid sequences of SEQ ID NOs: 29 or 31.

In some embodiments, a binding agent, or an antigen binding portion of a binding agent, comprises, or consists of, a CDR-H1 comprising an amino acid sequence at least 95%, at least 96%, at least 97%, at least 98%, at least 99% or 100% identical to any one of the amino acid sequences of SEQ ID NOs: 46 or 47; a CDR-H2 comprising an amino acid sequence at least 95%, at least 96%, at least 97%, at least 98%, at least 99% or 100% identical to any one of the amino acid sequences of SEQ ID NOs: 56 or 57; and a CDR-H3 comprising an amino acid sequence at least 95%, at least 96%, at least 97%, at least 98%, at least 99% or 100% identical to any one of the amino acid sequences of SEQ ID NOs: 68 or 69.

In some embodiments, a binding agent, or an antigen binding portion of a binding agent, comprises, or consists of, a CDR-H1 comprising an amino acid sequence at least 95%, at least 96%, at least 97%, at least 98%, at least 99% or 100% identical to any one of the amino acid sequences of SEQ ID NOs: 48 or 49; a CDR-H2 comprising an amino acid sequence at least 95%, at least 96%, at least 97%, at least 98%, at least 99% or 100% identical to any one of the amino acid sequences of SEQ ID NOs: 58, 59 or 60; and a CDR-H3 comprising an amino acid sequence at least 95%, at least 96%, at least 97%, at least 98%, at least 99% or 100% identical to any one of the amino acid sequences of SEQ ID NOs: 70 or 71.

In some embodiments, a binding agent, or an antigen binding portion of a binding agent, comprises, or consists of, a CDR-L1 comprising an amino acid sequence at least 95%, at least 96%, at least 97%, at least 98%, at least 99% or 100% identical to any one of the amino acid sequences of SEQ ID NOs: 2 or 3; a CDR-L2 comprising an amino acid sequence at least 95%, at least 96%, at least 97%, at least 98%, at least 99% or 100% identical to any one of the amino acid sequences of SEQ ID NOs: 16, 17 or 18; a CDR-L3 comprising an amino acid sequence at least 95%, at least 96%, at least 97%, at least 98%, at least 99% or 100% identical to any one of the amino acid sequences of SEQ ID NOs: 27 or 28; a CDR-H1 comprising an amino acid sequence at least 95%, at least 96%, at least 97%, at least 98%, at least 99% or 100% identical to any one of the amino acid sequences of SEQ ID NOs: 46 or 47; a CDR-H2 comprising an amino acid sequence at least 95%, at least 96%, at least 97%, at least 98%, at least 99% or 100% identical to any one of the amino acid sequences of SEQ ID NOs: 56 or 57; and a CDR-H3 comprising an amino acid sequence at least 95%, at least 96%, at least 97%, at least 98%, at least 99% or 100% identical to any one of the amino acid sequences of SEQ ID NOs: 68 or 69.

In some embodiments, a binding agent, or an antigen binding portion of a binding agent, comprises, or consists of, a CDR-L1 comprising an amino acid sequence at least 95%, at least 96%, at least 97%, at least 98%, at least 99% or 100% identical to any one of the amino acid sequences of SEQ ID NOs: 4 or 5; a CDR-L2 comprising an amino acid sequence at least 95%, at least 96%, at least 97%, at least 98%, at least 99% or 100% identical to any one of the amino acid sequences of SEQ ID NOs: 19, 20 or 21; a CDR-L3 comprising an amino acid sequence at least 95%, at least 96%, at least 97%, at least 98%, at least 99% or 100% identical to any one of the amino acid sequences of SEQ ID NOs: 29 or 30; a CDR-H1 comprising an amino acid sequence at least 95%, at least 96%, at least 97%, at least 98%, at least 99% or 100% identical to any one of the amino acid sequences of SEQ ID NOs: 48 or 49; a CDR-H2 comprising an amino acid sequence at least 95%, at least 96%, at least 97%, at least 98%, at least 99% or 100% identical to any one of the amino acid sequences of SEQ ID NOs: 58, 59 or 60; and a CDR-H3 comprising an amino acid sequence at least 95%, at least 96%, at least 97%, at least 98%, at least 99% or 100% identical to any one of the amino acid sequences of SEQ ID NOs: 70 or 71.

In some embodiments a binding agent, or an antigen binding portion of a binding agent, comprises, or consists of, a heavy chain variable region comprising an amino acid sequence at least 70%, at least 75%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identical to any one of the amino acid sequences of SEQ ID NOs: 77 to 88 (e.g., a heavy chain variable region selected from Tables 9 and 10), and/or a light chain variable region comprising an amino acid sequence at least 70%, at least 75%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identical to any one of the amino acid sequences of SEQ ID NOs: 35 to 45 (e.g., a light chain variable region selected from Tables 4 and 5). In some embodiments a binding agent, or an antigen binding portion of a binding agent, comprises a heavy chain variable region comprising an amino acid sequence at least 90% identical to any one of the amino acid sequences of SEQ ID NOs: 84 to 88 (e.g., a heavy chain variable region selected from Table 10), and a light chain variable region comprising an amino acid sequence at least 90% identical to any one of the amino acid sequences of SEQ ID NOs: 42 to 45 (e.g., a light chain variable region selected from Table 5).

The term "percent identical" or "percent identity" refers to sequence identity between two amino acid sequences. Identity can be determined by comparing a position in each sequence which may be aligned for purposes of comparison. When an equivalent position in the compared sequences is occupied by the same amino acid, then the molecules are identical at that position. When the equivalent site is occupied by the same or a similar amino acid residue (e.g., similar in steric and/or electronic nature), then the molecules can be referred to as homologous (similar) at that position. Expression as a percentage of homology, similarity, or identity refers to a function of the number of identical or similar amino acids at positions shared by the compared sequences. Expression as a percentage of homology, similarity, or identity refers to a function of the number of identical or similar amino acids at positions shared by the compared sequences. Various alignment algorithms and/or programs may be used, including FASTA, BLAST, or ENTREZ. FASTA and BLAST are available as a part of the GCG sequence analysis package (University of Wisconsin, Madison, Wis.), and can be used with, e.g., default settings. ENTREZ is available through the National Center for Biotechnology Information, National Library of Medicine, National Institutes of Health, Bethesda, Md. In one embodiment, the percent identity of two sequences can be determined by the GCG program with a gap weight of 1, e.g., each amino acid gap is weighted as if it were a single amino acid or nucleotide mismatch between the two sequences.

Other techniques for alignment are described in Methods in Enzymology, vol. 266: Computer Methods for Macromolecular Sequence Analysis (1996), ed. Doolittle, Academic Press, Inc., a division of Harcourt Brace & Co., San Diego, Calif., USA. In some embodiments an alignment program that permits gaps in the sequence is utilized to align the sequences. The Smith-Waterman is one type of algorithm that permits gaps in sequence alignments. See Meth. Mol. Biol. 70:173-187 (1997). Also, the GAP program using the Needleman and Wunsch alignment method can be utilized to align sequences. An alternative search strategy uses MPSRCH software, which runs on a MASPAR computer. MPSRCH uses a Smith-Waterman algorithm to score sequences on a massively parallel computer. This approach improves ability to pick up distantly related matches, and is especially tolerant of small gaps and nucleotide sequence errors. Nucleic acid-encoded amino acid sequences can be used to search both protein and DNA databases.

In some embodiments a binding agent, or antigen binding portion of a binding agent comprises one or more CDRs selected from a light chain variable region of Tables 4 and 5. In some embodiments a binding agent, or antigen binding portion of a binding agent comprises one or more CDRs selected from a heavy chain variable region of Tables 9 and 10. In some embodiments a binding agent, or antigen binding portion of a binding agent comprises one or more CDRs selected from a light chain variable region of Tables 4 and 5 and one or more CDRs selected from a heavy chain variable region of Tables 9 and 10. In certain embodiments, a binding agent, or antigen binding portion of a binding agent, comprises a CDR-L1, a CDR-L2, and a CDR-L3, each selected from any one of the light chain variable regions of Tables 4 and 5, and a CDR-H1, a CDR-H2, and a CDR-H3, each selected from any one of the heavy chain variable regions of Tables 9 and 10. An amino acid sequence of a CDR (e.g., a CDR-L1, CDR-L2, CDR-L3, CDR-H1, CDR-H2, and CDR-H3) can be identified within a heavy chain or light chain variable region disclosed herein by any suitable method described herein or known to those skilled in the art.

In some embodiments a binding agent comprises one or more suitable sequences selected from Tables 1-10 wherein the selected polypeptide sequence comprises 0 to 5, 1 to 5, 0 to 10, 1 to 10, 0 to 15, or 1 to 12 amino acid modifications where an amino acid modification can be an amino acid addition, an amino acid deletion and/or an amino acid substitution. In some embodiments, a binding agent disclosed herein comprises one or more amino acid analogues, non-native amino acids or amino acid derivatives.

In certain embodiments, a binding agent, or antigen binding portion of a binding agent comprises one or more framework regions (FR). Framework regions are often located between CDRs and/or flank CDR sequences of a heavy or light chain variable region of an antibody or binding agent. In mammals, a heavy chain variable region often comprises four framework regions and a light chain variable region often comprises four framework regions. Any suitable method can be used to identify one or more framework regions in an antibody, in a variable region of an antibody or in a binding agent. A binding agent may comprise synthetic or naturally occurring framework regions which are unmodified or modified (e.g., optimized) as discussed below.

In some embodiments a binding agent, or antigen binding portion thereof is chimeric, grafted and/or humanized. Chimeric, grafted and or humanized binding agents often comprise modified or substituted constant regions and/or framework regions while maintaining binding specificity to syndecan-1, or a portion thereof. In some embodiments a binding agent, or antigen binding portion thereof, comprises constant regions, framework regions, or portions thereof, derived from a human antibody. In some embodiments a binding agent, or antigen binding portion thereof, comprises fully synthetic portions, one or more amino acids, or sequences of amino acids that are not found in native antibody molecules.

Naturally occurring framework regions, or portions thereof may be obtained from any suitable species. In certain embodiments the complementarity determining regions (CDRs) of the light and heavy chain variable regions of a binding agent, or an antigen binding portion thereof, is grafted into framework regions from the same, or another, species. For example, one or more framework regions of a binding agent may be derived from a rodent species (e.g., a mouse or rat) or a primate species (e.g., a human).

In certain embodiments, the CDRs of the light and/or heavy chain variable regions of a binding agent, or an antigen binding portion thereof, can be grafted to consensus human framework regions. To create consensus human framework regions, in certain embodiments, framework regions from several human heavy chain or light chain amino acid sequences can be aligned to identify a consensus sequence. In certain embodiments, the heavy chain or light chain framework regions of an antibody or binding agent are replaced with one or more framework regions, or portions thereof, from a different heavy chain or light chain variable region. In some embodiments a binding agent, or antigen binding portion thereof, comprises one or more human framework regions. In certain embodiments a binding agent, or antigen binding portion thereof, comprises at least 1, 2, 3, 4, 5, 6, 7, 8, 9 or 10 human framework regions. In some embodiments a binding agent, or antigen binding portion thereof, comprises one or more mouse framework regions. In certain embodiments a binding agent, or antigen binding portion thereof, comprises at least 1, 2, 3, 4, 5, 6, 7, 8, 9 or 10 mouse framework regions. In certain embodiments a binding agent, or antigen binding portion thereof, comprises one or more human framework regions and one or more mouse framework regions.

Methods of generating chimeric, humanized and/or optimized antibodies or binding agents, for example by modifying, substituting or deleting framework regions, or portions thereof, are known. Non-limiting examples of CDR grafting are described, e.g., in U.S. Pat. Nos. 6,180,370, 6,054,297, 5,693,762, 5,859,205, 5,693,761, 5,565,332, 5,585,089, and 5,530, 101, and in Jones et al, Nature, 321:522-525 (1986); Verhoeyen et al, Science, 239:1534-1536 (1988), and Winter, FEBS Letts., 430:92-(1998). Additional non-limiting examples of generating chimeric, grafted and/or humanized binding agents include U.S. Pat. Nos. 5,530,101; 5,707,622; 5,994,524; 6,245,894; Queen et al., (1988) PNAS 86:10029-10033; Riechmann et al., Nature (1988) 332:323-327; Antibody Engineering: Methods and Protocols, Vol. 248 of Methods in molecular biology, edited by Benny K. C. Lo, Springer Science & Business Media, (2004); and Antibody Engineering, Vol. 1, Roland E. Kontermann, Stefan Duebel, Edition 2, Publisher Springer Science & Business Media, (2010). In some embodiments a binding agent can be humanized by exchanging one or more framework regions, or portions thereof (e.g., one or more amino acids), with one or more framework regions, or portions thereof from a human antibody. In certain embodiments, an antibody or binding agent can be humanized or grafted by transferring one or more CDRs (e.g., 1, 2, 3, 4, 5 or all 6 CDRs) from a donor binding agent (e.g., a mouse monoclonal antibody) to an acceptor binding agent (e.g., a human antibody) while retaining the binding specificity of the donor binding agent. In certain embodiments, the process of making a chimeric, grafted or humanized binding agent comprises making one or more amino acid substitutions, additions or deletions in a constant region or framework region of a binding agent. In certain embodiments, techniques such as "reshaping", "hyperchimerization," or "veneering/resurfacing" can be used to produce humanized binding agents. (e.g., see Vaswami et al, Annals of Allergy, Asthma, & Immunol. 81:105 (1998); Roguska et al, Prot. Engin., 9:895-904 (1996); and U.S. Pat. No. 6,072,035). In some aspects, a binding agent is modified by a method discussed above, or by another suitable method, to reduce immunogenicity (e.g., see Gilliland et al, J. Immunol, 62(6): 3663-71 (1999)).

In certain embodiments, an amino acid sequence of a binding agent is modified to optimize binding affinity for a target (e.g., syndecan-1), species cross-reactivity, solubility and/or function (e.g., agonist activity, or lack thereof). In some embodiments a specific combination of CDRs disclosed herein can be optimized for binding to syndecan-1, and/or to optimize a function or characteristic of a binding agent disclosed herein. For example, a characterized light chain variable region disclosed herein (e.g., a light chain variable region of any one of SEQ ID NOs:35-45) can be co-expressed, using a suitable expression system, with a library of heavy chain variable regions comprising a CDR-H1 and CDR-H2 of a characterized heavy chain variable region (e.g., a heavy chain variable region selected from Tables 6 or 7), where the CDR-H3 is replaced with a library of CDR-H3 sequences, which may include one or more CDR-H3 regions of Table 8, for example. The resulting light chain/heavy chain binding agents can be screened for binding to syndecan-1 and/or for a specific function. Optimized binding agents can be identified and the amino acid sequence of the CDR-H3 can be identified by a suitable method. The above screening method can be used to identify binding agents comprising specific combinations of CDRs, or specific optimized CDR sequences (e.g., CDR sequences comprising amino acid substitutions, additions or deletions) that provide a binding agent with improved binding specificity, binding affinity and/or function. Such methods of screening and optimizing binding agents are known (e.g., see Portolano et al., (1993) Journal of Immunology 150: 880-887; and Clarkson et al., (1991) Nature 352:624-628). Such references teach methods of producing antibodies that bind a specific antigen by using known variable light chain, known variable heavy chains, or portion thereof (e.g., CDRs thereof) by screening a library of complementary variable regions.

In certain embodiments, a binding agent is modified to eliminate or add glycosylation sites in order to optimize affinity and/or function of a binding agent (e.g., see Co et al, Mol. Immunol, 30:1361-1367 (1993)). In some embodiments the number and/or type of glycosylation sites in a binding agent is modified or altered. An N-linked glycosylation site is often characterized by the sequence Asn-X-Ser or Asn-X-Thr, where the amino acid residue designated as X can be any amino acid residue except proline. The substitution of amino acid residues to create this sequence provides a potential new site for the addition of an N-linked carbohydrate chain. Alternatively, substitutions which eliminate this sequence will remove an existing N-linked carbohydrate chain. Also provided in certain embodiments is a rearrangement of N-linked carbohydrate chains where one or more N-linked glycosylation sites (typically those that are naturally occurring) are eliminated and one or more new N-linked sites are created. In some embodiments a binding agent is modified by deleting one or more cysteine residues or substituting one or more cysteine residues for another amino acid (e.g., serine) as compared to an unmodified binding agent. In certain embodiments cysteine variants can be useful for optimizing expression, secretion, and/or solubility.

In certain embodiments a binding agent is modified to include certain amino acid additions, substitutions, or deletions designed or intended, for example, to reduce susceptibility of a binding agent to proteolysis, reduce susceptibility of a binding agent to oxidation, increase serum half-life and/or confer or modify other physicochemical, pharmacokinetic or functional properties of a binding agent.

In some embodiments a binding agent specifically binds to a mammalian syndecan-1, or portion thereof. In certain embodiments, a binding agent described herein specifically binds to a mammalian syndecan-1, or portion thereof, with a binding affinity (KD) of $10^{-5}$ M or less, $10^{-6}$ M or less, $10^{-7}$ M or less, $10^{-8}$ M or less, 50 nM or less, 10 nM or less, or 1 nM or less. In certain embodiments, a binding agent described herein specifically binds to a mammalian syndecan-1, or portion thereof, with a binding affinity (KD) from about $10^{-5}$ to $10^{-15}$ M, $10^{-6}$ to $10^{-15}$ M, $10^{-7}$ to $10^{-15}$ M, $10^{-9}$ to $10^{-15}$ M, $10^{-9}$ to $10^{-14}$ M, $10^{-9}$ to $10^{-13}$ M, or $10^{-9}$ to about $10^{-12}$ M. In some embodiments a binding agent specifically binds to an extracellular domain or extracellular region of a mammalian syndecan-1, or a portion thereof. In certain aspects, a binding agent specifically binds to a wild-type syndecan-1 produced by a cell of an unaltered (non-genetically modified) mammal found in nature. In certain aspects a binding agent specifically binds to a naturally occurring syndecan-1 variant. In certain aspects a binding agent specifically binds to a syndecan-1 comprising one or more amino acid substitutions, additions or deletions. In certain embodiments a binding agent specifically binds to a syndecan-1 produced and/or expressed on the surface of a cell of a human, non-human primate, dog, cat, or rodent (e.g., a mouse or rat). In certain embodiments, a binding agent specifically binds to one or more syndecan-1 polypeptides, or a portion thereof (e.g., an extracellular domain), comprising an amino acid sequence of any one of SEQ ID NOs: 1 and 99 to 102. In certain embodiments, a binding agent described herein specifically binds to one or more syndecan-1 polypeptides, or a portion thereof, having an amino acid sequence of any one of SEQ ID NOs: 1 and 99 to 102 with a binding affinity (KD) of 50 nM or less, 10 nM or less, or 1 nM or less. In certain embodiments, a binding agent specifically binds to a human syndecan-1. In certain embodiments, a binding agent specifically binds to an extracellular domain of human syndecan-1. In certain embodiments, a binding agent specifically binds to a human syndecan-1, and/or an extracellular domain thereof.

In certain embodiments, a binding agent specifically binds to a polypeptide sequence comprising or consisting of the amino acid sequence of AGEGPKEGEAVVLP (SEQ ID NO:89) or GPKEGEAVVLP (SEQ ID NO:90). In certain embodiments, a binding agent described herein specifically binds to a polypeptide sequence comprising or consisting of the amino acid sequence of AGEGPKEGEAVVLP (SEQ ID NO:89) or GPKEGEAVVLP (SEQ ID NO:90) with a binding affinity (KD) of $10^{-5}$ M or less, $10^{-6}$ M or less, $10^{-7}$ M or less, $10^{-8}$ M or less, 50 nM or less, 10 nM or less, or 1 nM or less. In certain embodiments, a binding agent specifically binds to a polypeptide sequence comprising or consisting of the amino acid sequence of $GX_1KEX_2EAX_3VLP$ (SEQ ID NO:91), wherein $X_1$, $X_2$ and $X_3$ are selected from any amino acid. In some embodiments $X_1$ is selected from proline, alanine, cysteine, glycine, serine, threonine, and valine, and/or $X_2$ is selected from proline, alanine, cysteine, glycine, serine, threonine, and valine, and/or $X_3$ is selected from proline, alanine, cysteine, glycine, serine, threonine, valine, methionine, leucine, isoleucine and phenylalanine. In certain embodiments, a binding agent described herein specifically binds to a polypeptide sequence comprising or consisting of the amino acid sequence of $GX_1KEX_2EAX_3VLP$ (SEQ ID NO:91) with a binding affinity (KD) of 50 nM or less, 10 nM or less, or 1 nM or less, where $X_1$ is selected from proline, alanine, cysteine, glycine, serine, threonine, and valine, $X_2$ is selected from proline, alanine, cysteine, glycine, serine, threonine, and valine, and $X_3$ is selected from proline, alanine, cysteine, glycine, serine, threonine, valine, methionine, leucine, isoleucine and phenylalanine. In certain embodiments, $X_1$ is proline, $X_2$ is selected from alanine, glycine, or serine and $X_3$ is selected from alanine, glycine, and valine.

The term "specifically binds" refers to a binding agent that binds to a target peptide in preference to binding other molecules or other peptides as determined by, for example, as determined by a suitable in vitro assay (e.g., an Elisa, Immunoblot, Flow cytometry, and the like). A specific binding interaction discriminates over non-specific binding interactions by about 2-fold or more, often about 10-fold or more, and sometimes about 100-fold or more, 1000-fold or more, 10,000-fold or more, 100,000-fold or more, or 1,000,000-fold or more.

In some embodiments a binding agent that specifically binds to syndecan-1, or a portion thereof, is a binding agent that binds syndecan-1, or a portion thereof (e.g., an extracellular domain of syndecan-1), with a binding affinity constant (KD) equal to or less than 100 nM, equal to or less than 50 nM, equal to or less than 25 nM, equal to or less than 10 nM, equal to or less than 5 nM, equal to or less than 1 nM, equal to or less than 900 pM, equal to or less than 800 pM, equal to or less than 750 pM, equal to or less than 700 pM, equal to or less than 600 pM, equal to or less than 500 pM, equal to or less than 400 pM, equal to or less than 300 pM, equal to or less than 200 pM, or equal to or less than 100 pM. In some embodiments a binding agent that specifically binds to syndecan-1, or a portion thereof, is a binding agent that binds human syndecan-1, or a portion thereof (e.g., an extracellular domain of human syndecan-1), with a binding affinity constant (KD) equal to or less than 100 nM, equal to or less than 50 nM, equal to or less than 25 nM, equal to or less than 10 nM, equal to or less than 5 nM, equal to or less than 1 nM, equal to or less than 900 pM, equal to or less than 800 pM, equal to or less than 750 pM, equal to or less than 700 pM, equal to or less than 600 pM, equal to or less than 500 pM, equal to or less than 400 pM, equal to or less than 300 pM, equal to or less than 200 pM, or equal to or less than 100 pM. In some embodiments a binding agent that specifically binds to syndecan-1, or a portion thereof, is a binding agent that binds specifically to syndecan-1, or a portion thereof, derived from a non-human species (e.g., a non-human primate, or rodent; e.g., a mouse or rat), with a binding affinity constant (KD) equal to or less than 100 nM, equal to or less than 50 nM, equal to or less than 25 nM, equal to or less than 10 nM, equal to or less than 5 nM, equal to or less than 1 nM, equal to or less than 900 pM, equal to or less than 800 pM, equal to or less than 750 pM, equal to or less than 700 pM, equal to or less than 600 pM, equal to or less than 500 pM, equal to or less than 400 pM, equal to or less than 300 pM, equal to or less than 200 pM, or equal to or less than 100 pM.

In certain embodiments, a binding agent disclosed herein specifically binds human syndecan-1, or a portion thereof, and specifically binds to syndecan-1, or a portion thereof, derived from a non-human primate. In certain embodiments, a binding agent disclosed herein specifically binds to human syndecan-1, or a portion thereof, and specifically binds to syndecan-1, or a portion thereof, derived from a rodent (e.g., a mouse or rat). In certain embodiments, a binding agent (i) specifically binds to a human syndecan-1, or portion thereof (e.g., an extracellular domain of human syndecan-1) with a binding affinity (KD) of 10 nM or less, or 1 nM or less, and (ii) specifically binds to a rat or mouse syndecan-1, or portion thereof (e.g., an extracellular domain of rat or mouse syndecan-1) with a binding affinity (KD) of 100 nM or less, 90 nM or less, 80 nM or less, 70 nM or less, 60 nM or less, 50 nM or less, 40 nM or less, 30 nM or less, 20 nM or less or 10 nM or less.

In certain embodiments, a second binding agent (e.g., a second syndecan-1 binding agent) is a binding agent that competes for binding with a first syndecan-1 binding agent to syndecan-1, a portion thereof, or epitope thereof, where a first syndecan-1 binding agent is a binding agent comprising one or more CDRs shown in Tables 1-10, or one or more CDRs that are substantially similar to those shown in Tables 1-10. In certain embodiments, the epitope of syndecan-1 comprises a polypeptide comprising the amino acid sequence of SEQ ID NO:89, 90 or 91. In certain embodiments, a second binding agent competes for binding of a first binding agent described herein to a polypeptide comprising or consisting of the amino acid sequence of SEQ ID NO: 89, 90 or 91. In some embodiments, the second binding agent may have an amino acid sequence that is distinct and/or different from a first binding agent described herein. For example, a second syndecan-1 binding agent that competes for binding to a binding agent described herein often does not contain a CDR sequence shown in Tables 1-2 or 6-8. A second syndecan-1 binding agent may have a light chain variable region sequence that is substantially different from the light chain variable regions shown in Tables 3 and 4. A second syndecan-1 binding agent may have a heavy chain variable region sequence that is substantially different from the heavy chain variable regions shown in Tables 9 and 10.

Methods of identifying binding agents that compete for binding to an antigen are known. Any suitable method can be used to determine if a second syndecan-1 binding agent completes with a first syndecan-1 binding agent for binding to a syndecan-1 antigen. For example, ELISA-based methods can be used where a syndecan-1 antigen, or portion thereof, is coated on a 96-well plate. A second syndecan-1 binding agent is added and allowed to bind to the coated antigen. The plate is then washed and a first binding agent described herein (e.g., a syndecan-1 binding agent described herein) is added to the plate and allowed to bind. The amount of binding of the first binding agent is measured in the presence or absence of the second syndecan-1 binding agent to determine if the first binding agent and second binding compete for binding to the plate coated antigen.

In some embodiments a binding agent comprises a label. As used herein, the terms "label" or "labeled" refers to incorporation of a detectable marker, e.g., by incorporation of a labeled amino acid or attachment to a polypeptide of biotin moieties that can be detected by labeled avidin (e.g., streptavidin containing a fluorescent marker or enzymatic activity that can be detected by optical or colorimetric methods). In certain embodiments, a label or marker can be attached to a binding agent to generate a diagnostic agent. A binding agent can be attached covalently or non-covalently to any suitable label or marker. Various methods of labeling polypeptides and glycoproteins are known to those skilled in the art and can be used. Non-limiting examples of labels for polypeptides include, but are not limited to fluorescent labels, enzymatic labels (e.g., horseradish peroxidase, β-galactosidase, luciferase, alkaline phosphatase), chemiluminescent labels, a metallic label, a chromophore, an electrochemiluminescent label, a phosphorescent label, a quencher (e.g., a fluorophore quencher), a fluorescence resonance energy transfer (FRET) pair (e.g., donor and acceptor), a dye, an enzyme substrate, a small molecule, a mass tag, quantum dots, nanoparticles, biotinyl groups, predetermined polypeptide epitopes recognized by a secondary reporter (e.g., leucine zipper pair sequences, binding sites for secondary antibodies, metal binding domains, epitope tags), the like or combinations thereof.

In some embodiments a binding agent comprises a suitable carrier. A binding agent can be attached covalently or non-covalently to a suitable carrier. Non-limiting examples of a carrier include agents or molecules that alter or extend the in vivo half-life of a binding agent, polyethylene glycol, glycogen (e.g., by glycosylation of a binding agent), a dextran, a carrier or vehicle described in U.S. Pat. No. 6,660,843, the like or combinations thereof.

In some embodiments a label or carrier is bound to a binding agent by use of a suitable linker. Non-limiting examples of a suitable linker include silanes, thiols, phosphonic acid, polyethylene glycol (PEG), amino acids and peptides, polymers thereof, derivatives thereof, the like and combinations thereof. Methods of attaching two or more molecules using a linker are to those skilled in the art and are sometimes referred to as "crosslinking."

In some embodiments a label, carrier or linker is attached to a suitable thiol group of a binding agent (e.g., a thiol group of a cysteine residue). Any suitable amino acid residue of a constant region or framework region of a binding agent can be substituted with an amino acid residue containing a thiol group (e.g., a cysteine) for the purpose of attaching a label, carrier or linker. Non-limiting examples of amino acids that can be substituted with a thiol containing amino acid residue include A118, S119, S239, V282, T289, N361, and V422 of an $IgG_2$, S115, S252, V289, T306, and N384 of an $IgG_1$, or a corresponding position in an $IgG_1$, $IgG_2$, $IgG_3$ or $IgG_4$. Other non-limiting examples of attaching a label, carrier and/or linker to a binding agent include reacting an amine with an N-hydroxysuccinimide (NHS) ester, an imidoester, a pentafluorophenyl (PFP) ester, a hydroxymethyl phosphine, an oxirane or any other carbonyl compound; reacting a carboxyl with a carbodiimide; reacting a sulfhydryl with a maleimide, a haloacetyl, a pyridyldisulfide, and/or a vinyl sulfone; reacting an aldehyde with a hydrazine; reacting any non-selective group with diazirine and/or aryl azide; reacting a hydroxyl with isocyanate; reacting a hydroxylamine with a carbonyl compound; the like and combinations thereof.

In some embodiments, presented herein is a composition or pharmaceutical composition comprising one or more binding agents that binds specifically to syndecan-1, or a portion thereof (e.g., an extracellular domain of syndecan-1, or a portion thereof).

A pharmaceutical composition can be formulated for a suitable route of administration. In some embodiments a pharmaceutical composition is formulated for subcutaneous (s.c.), intradermal, intramuscular, intraperitoneal and/or intravenous (i.v.) administration. In certain embodiments, a pharmaceutical composition can contain formulation materials for modifying, maintaining, or preserving, for example, the pH, osmolarity, viscosity, clarity, color, isotonicity, odor, sterility, stability, rate of dissolution or release, adsorption or penetration of the composition. In certain embodiments, suitable formulation materials include, but are not limited to, amino acids (such as glycine, glutamine, asparagine, arginine or lysine); antimicrobials; antioxidants (such as ascorbic acid, sodium sulfite or sodium hydrogen-sulfite); buffers (such as borate, bicarbonate, Tris-HCl, citrates, phosphates (e.g., phosphate buffered saline) or suitable organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counter ions (such as sodium); solvents (such as glycerin, propylene glycol or polyethylene glycol); diluents; excipients and/or pharmaceutical adjuvants (Remington's Pharmaceutical Sciences, 18th Ed., A. R. Gennaro, ed., Mack Publishing Company (1995)).

In certain embodiments, a pharmaceutical composition comprises a suitable excipient, non-limiting example of which include anti-adherents (e.g., magnesium stearate), a binder, fillers, monosaccharides, disaccharides, other carbohydrates (e.g., glucose, mannose or dextrins), sugar alcohols (e.g., mannitol or sorbitol), coatings (e.g., cellulose, hydroxypropyl methylcellulose (HPMC), microcrystalline cellulose, synthetic polymers, shellac, gelatin, corn protein zein, enterics or other polysaccharides), starch (e.g., potato, maize or wheat starch), silica, colors, disintegrants, flavors, lubricants, preservatives, sorbents, sweeteners, vehicles, suspending agents, surfactants and/or wetting agents (such as pluronics, PEG, sorbitan esters, polysorbates such as polysorbate 20, polysorbate 80, triton, tromethamine, lecithin, cholesterol, tyloxapal), stability enhancing agents (such as sucrose or sorbitol), and tonicity enhancing agents (such as alkali metal halides, sodium or potassium chloride, mannitol, sorbitol), and/or any excipient disclosed in Remington's Pharmaceutical Sciences, 18th Ed., A. R. Gennaro, ed., Mack Publishing Company (1995). The term "binder" as used herein refers to a compound or ingredient that helps keeps a pharmaceutical mixture combined. Suitable binders for making pharmaceutical formulations and are often used in the preparation of pharmaceutical tablets, capsules and granules are known to those skilled in the art. For clarification, the term "binding agent" as used herein does not refer to a "binder" that is used in certain pharmaceutical formulations. Although a pharmaceutical composition, in certain embodiments, may comprise a binding agent that specifically binds syndecan-1 as well as a binder.

In some embodiments a pharmaceutical composition comprises a suitable pharmaceutically acceptable additive and/or carrier. Non-limiting examples of suitable additives include a suitable pH adjuster, a soothing agent, a buffer, a sulfur-containing reducing agent, an antioxidant and the like. Non-limiting examples of a sulfur-containing reducing agent includes those having a sulfhydryl group such as N-acetylcysteine, N-acetylhomocysteine, thioctic acid, thiodiglycol, thioethanolamine, thioglycerol, thiosorbitol, thioglycolic acid and a salt thereof, sodium thiosulfate, glutathione, and a C1-C7 thioalkanoic acid. Non-limiting examples of an antioxidant include erythorbic acid, dibutylhydroxytoluene, butylhydroxyanisole, alpha-tocopherol, tocopherol acetate, L-ascorbic acid and a salt thereof, L-ascorbyl palmitate, L-ascorbyl stearate, sodium bisulfite, sodium sulfite, triamyl gallate and propyl gallate, as well as chelating agents such as disodium ethylenediaminetetraacetate (EDTA), sodium pyrophosphate and sodium metaphosphate. Furthermore, diluents, additives and excipients may comprise other commonly used ingredients, for example, inorganic salts such as sodium chloride, potassium chloride, calcium chloride, sodium phosphate, potassium phosphate and sodium bicarbonate, as well as organic salts such as sodium citrate, potassium citrate and sodium acetate.

The pharmaceutical compositions used herein can be stable over an extended period of time, for example on the order of months or years. In some embodiments a pharmaceutical composition comprises one or more suitable preservatives. Non limiting examples of preservatives include benzalkonium chloride, benzoic acid, salicylic acid, thimerosal, phenethyl alcohol, methylparaben, propylparaben, chlorhexidine, sorbic acid, hydrogen peroxide, the like and/or combinations thereof. A preservative can comprise a quaternary ammonium compound, such as benzalkonium chloride, benzoxonium chloride, benzethonium chloride, cetrimide, sepazonium chloride, cetylpyridinium chloride, or domiphen bromide (BRADOSOL(registered trademark)). A preservative can comprise an alkyl-mercury salt of thiosalicylic acid, such as thimerosal, phenylmercuric nitrate, phenylmercuric acetate or phenylmercuric borate. A preservative can comprise a paraben, such as methylparaben or propylparaben. A preservative can comprise an alcohol, such as chlorobutanol, benzyl alcohol or phenyl ethyl alcohol. A preservative can comprise a biguanide derivative, such as chlorohexidine or polyhexamethylene biguanide. A preservative can comprise sodium perborate, imidazolidinyl urea, and/or sorbic acid. A preservative can comprise stabilized oxychloro complexes, such as known and commercially available under the trade name PURITE(registered trademark). A preservative can comprise polyglycol-polyamine condensation resins, such as known and commercially available under the trade name POLYQUART (registered trademark) from Henkel KGaA. A preservative can comprise stabilized hydrogen peroxide. A preservative can be benzalkonium chloride. In some embodiments a pharmaceutical composition is free of preservatives.

In some embodiments a composition, pharmaceutical composition or binding agent is substantially free of blood, or a blood product contaminant (e.g., blood cells, platelets, polypeptides, minerals, blood borne compounds or chemicals, and the like). In some embodiments a composition, pharmaceutical composition or binding agent is substantially free of serum and serum contaminants (e.g., serum proteins, serum lipids, serum carbohydrates, serum antigens and the like). In some embodiments a composition, pharmaceutical composition or binding agent is substantially free a pathogen (e.g., a virus, parasite or bacteria). In some embodiments a composition, pharmaceutical composition or binding agent is substantially free of endotoxin. In some embodiments a composition, pharmaceutical composition or binding agent is sterile. In certain embodiments, a composition or pharmaceutical composition comprises a binding agent that specifically binds an extracellular domain of syndecan-1 and a diluent (e.g., phosphate buffered saline). In certain embodiments, a composition or pharmaceutical composition comprises a binding agent that specifically binds an extracellular domain of syndecan-1 and an excipient, (e.g., sodium citrate dehydrate, or polyoxyethylene-sorbitan-20 mono-oleate (polysorbate 80)).

The pharmaceutical compositions described herein may be configured for administration to a subject in any suitable form and/or amount according to the therapy in which they are employed. For example, a pharmaceutical composition configured for parenteral administration (e.g., by injection or infusion), may take the form of a suspension, solution or emulsion in an oily or aqueous vehicle and it may contain formulation agents, excipients, additives and/or diluents such as aqueous or non-aqueous solvents, co-solvents, suspending solutions, preservatives, stabilizing agents and or dispersing agents. In some embodiments a pharmaceutical composition suitable for parental administration may contain one or more excipients. In some embodiments a pharmaceutical composition is lyophilized to a dry powder form. In some embodiments a pharmaceutical composition is lyophilized to a dry powder form, which is suitable for reconstitution with a suitable pharmaceutical solvent (e.g., water, saline, an isotonic buffer solution (e.g., PBS), and the like). In certain embodiments, reconstituted forms of a lyophilized pharmaceutical composition are suitable for parental administration (e.g., intravenous administration) to a mammal.

In certain embodiments, a pharmaceutical composition is configured for oral administration and may be formulated as a tablet, microtablet, minitablets, micropellets, powders granules, capsules (e.g., capsules filled with microtablets, micropellets, powders or granules), emulsions or solutions. Pharmaceutical compositions configured for oral administration may comprise suitable coatings to delay or sustain release of the active ingredient (e.g., a binding agent), non-limiting examples of which include enteric coatings such as fatty acids, waxes, shellac, plastics, methyl acrylate-methacrylic acid copolymers, cellulose acetate phthalate (CAP), cellulose acetate succinate, hydroxypropyl methyl cellulose phthalate, hydroxypropyl methyl cellulose acetate succinate (hypromellose acetate succinate), polyvinyl acetate phthalate (PVAP), methyl methacrylate-methacrylic acid copolymers, cellulose acetate trimellitate, sodium alginate, zein, plant fibers, the like and combinations thereof.

In some embodiments a pharmaceutical compositions described herein may be configured for topical administration and may include one or more of a binding and/or lubricating agent, polymeric glycols, gelatins, cocoa-butter or other suitable waxes or fats. In some embodiments a pharmaceutical composition described herein is incorporated into a topical formulation containing a topical carrier that is generally suited to topical drug administration and comprising any suitable material known to those skilled in the art. In certain embodiments, a topical formulation of a pharmaceutical composition is formulated for administration of a binding agent from a topical patch.

In certain embodiments, an optimal pharmaceutical composition will be determined by one skilled in the art depending upon, for example, the intended route of administration, delivery format and desired dosage (see e.g., Remington's Pharmaceutical Sciences, supra). In certain embodiments, such compositions may influence the physical state, stability, rate of in vivo release and rate of in vivo clearance of the antibodies of the invention.

In some embodiments a composition, pharmaceutical composition or binding agent described herein is used to treat a subject having or suspected of having a neoplastic disorder or cancer. In certain embodiments, a binding agent or pharmaceutical composition described herein is used in treating a neoplastic disorder or cancer in a subject, wherein the binding agent specifically binds to an extracellular domain of human syndecan-1. In some embodiments, presented herein is a method of treating a subject having or suspected of having a neoplastic disorder or cancer. In certain embodiments, a method of treating a subject having or suspected of having a neoplastic disorder or cancer comprises administering a therapeutically effective amount of a composition, pharmaceutical composition or binding agent described herein to the subject. In certain embodiments, a method of treatment comprises contacting a cell (e.g., one or more cells) of a subject with a therapeutically effective amount of a composition, pharmaceutical composition or binding agent described herein. In certain embodiments, a method of treatment comprises contacting a cell (e.g., one or more cells) of a subject with a therapeutically effective amount of a binding agent that specifically binding to an extracellular portion of human syndecan-1, or variant thereof. The cell of a subject is often a cell that expresses an extracellular portion of syndecan-1. A cell of a subject may be found inside a subject (e.g., in vivo) or outside the subject (e.g., in vitro or ex vivo).

A composition, pharmaceutical composition or binding agent disclosed herein can be used to treat a suitable neoplastic order or cancer involving a cell type that expresses syndecan-1. Non-limiting examples of a neoplastic disorder or cancer that can be treated by a method herein includes a lung carcinoma, breast carcinoma, ovarian carcinoma, kidney carcinoma, colorectal carcinoma, gastric carcinoma, thyroid carcinoma, pancreas carcinoma, neuroblastoma, or a squamous cell carcinoma of the head and neck, cervical cancer, hepatocellular cancer, sarcomas, mesothelioma, glioblastoma, multiple myeloma, melanoma, prostate and esophageal carcinoma. In certain embodiments a neoplastic cell of a cancer or neoplastic order can be quickly assayed for expression of syndecan-1 using a suitable anti-syndecan-1 binding agent, or a novel binding agent described herein by using a suitable method (e.g., whole cell ELISA, FACS, any suitable immunoassay, and the like).

Any suitable method of administering a composition, pharmaceutical composition or binding agent to a subject can be used. The exact formulation and route of administration for a composition for use according to the methods of the invention described herein can be chosen by the individual physician in view of the patient's condition. See, e.g., Fingl et al. 1975, in "The Pharmacological Basis of Therapeutics," Ch. 1, p. 1; which is incorporated herein by reference in its entirety. Any suitable route of administration can be used for administration of a pharmaceutical composition or a binding agent described herein. Non-limiting examples of routes of administration include topical or local (e.g., transdermally or cutaneously, (e.g., on the skin or epidermis), in or on the eye, intranasally, transmucosally, in the ear, inside the ear (e.g., behind the ear drum)), enteral (e.g., delivered through the gastrointestinal tract, e.g., orally (e.g., as a tablet, capsule, granule, liquid, emulsification, lozenge, or combination thereof), sublingual, by gastric feeding tube, rectally, and the like), by parenteral administration (e.g., parenterally, e.g., intravenously, intra-arterially, intramuscularly, intraperitoneally, intradermally, subcutaneously, intracavity, intracranial, intra-articular, into a joint space, intracardiac (into the heart), intracavernous injection, intralesional (into a skin lesion), intraosseous infusion (into the bone marrow), intrathecal (into the spinal canal), intra-uterine, intravaginal, intravesical infusion, intravitreal), the like or combinations thereof.

In some embodiments a composition herein is provided to a subject. A composition that is provided to a subject is sometimes provided to a subject for self-administration or for administration to a subject by another (e.g., a non-medical professional). For example a composition described herein can be provided as an instruction written by a medical practitioner that authorizes a patient to be provided a composition or treatment described herein (e.g., a prescription). In another example, a composition can be provided to a subject where the subject self-administers a composition orally, intravenously or by way of an inhaler, for example.

Alternately, one can administer compositions for use according to the methods of the invention in a local rather than systemic manner, for example, via direct application to the skin, mucous membrane or region of interest for treating, including using a depot or sustained release formulation.

In some embodiments a pharmaceutical composition comprising a binding agent can be administered alone (e.g., as a single active ingredient (AI or e.g., as a single active pharmaceutical ingredient (API)). In other embodiments, a pharmaceutical composition comprising a binding agent can be administered in combination with one or more additional AIs/APIs, for example, as two separate compositions or as a single composition where the one or more additional AIs/APIs are mixed or formulated together with the binding agent in a pharmaceutical composition.

In certain embodiments, a syndecan-1 binding agent is delivered to a cell (e.g., a mammalian cell). A syndecan-1 binding agent can be delivered to a cell using any suitable method. In certain embodiments, delivering a syndecan-1 binding agent to a cell comprises contacting a mammalian cell, in vitro or in vivo, with a composition comprising a syndecan-1 binding agent under conditions that allow the binding agent to bind to the cell.

A pharmaceutical composition can be manufactured by any suitable manner, including, e.g., by means of conventional mixing, dissolving, granulating, dragee-making, levigating, emulsifying, encapsulating, entrapping or tableting processes.

In some embodiments a pharmaceutical composition comprising a binding agent is administered at a suitable frequency or interval as needed to obtain an effective therapeutic outcome. An effective therapeutic outcome can be determined by monitoring the number, viability, growth, mitosis, or metastasis of neoplastic or cancerous cells in a subject affected with a neoplastic disorder or cancer. Accordingly, in certain embodiments, a decrease in the number, viability, growth, mitosis, or metastasis of neoplastic or cancerous cells in a subject is considered an effective therapeutic outcome. In some embodiments, a pharmaceutical composition comprising a binding agent can be administered hourly, once a day, twice a day, three times a day, four times a day, five times a day, and/or at regular intervals, for example, every day, every other day, three times a week, weekly, every other week, once a month and/or simply at a frequency or interval as needed or recommended by a medical professional.

In some embodiments, an amount of a binding agent in a composition is an amount needed to obtain an effective therapeutic outcome. In certain embodiments, the amount of a binding agent in a composition (e.g., a pharmaceutical composition) is an amount sufficient to prevent, treat, reduce the severity of, delay the onset of, and/or alleviate a symptom of a neoplastic disorder or cancer, as contemplated herein.

A "therapeutically effective amount" means an amount sufficient to obtain an effective therapeutic outcome and/or an amount necessary sufficient to prevent, treat, reduce the severity of, delay the onset of, and/or alleviate a symptom of a neoplastic disorder or cancer. In certain embodiments, a "therapeutically effective amount" means an amount sufficient to terminate the growth of, and/or slow the growth of a neoplasm or cancer. In certain embodiments, a "therapeutically effective amount" means an amount sufficient to inhibit the replication of, and/or induce the death of one or more neoplastic cells. Determination of a therapeutically effective amount is well within the capability of those skilled in the art, especially in light of the detailed disclosure provided herein.

In some embodiments, an amount of a binding agent in a composition is an amount that is at least a therapeutically effective amount and an amount low enough to minimize unwanted adverse reactions. The exact amount of a binding agent or combinations of active agents required will vary from subject to subject, depending on age, weight, and general condition of a subject, the severity of the condition being treated, and the particular combination of drugs administered. Thus, it is not always possible to specify an exact therapeutically effective amount to treat a neoplastic disorder in a diverse group of subjects. As is well known, the specific dosage for a given patient under specific conditions and for a specific disease will routinely vary, but determination of the optimum amount in each case can readily be accomplished by simple routine procedures. Thus, a therapeutically effective amount of a binding agent used to treat a neoplastic disorder may be determined by one of ordinary skill in the art using routine experimentation.

In certain embodiments, an amount of a binding agent in a composition is administered at a suitable therapeutically effective amount or a dose (e.g., at a suitable volume and concentration, which sometimes depends, in part, on a particular route of administration). Within certain embodiments, a binding agent (e.g., a binding agent in a composition) can be administered at a dose from about 0.01 mg/kg (e.g., per kg body weight of a subject) to 500 mg/kg, 0.1 mg/kg to 500 mg/kg, 0.1 mg/kg to 400 mg/kg, 0.01 mg/kg to 300 mg/kg, 0.1 mg/kg to 300 mg/kg, 0.1 mg/kg to 200 mg/kg, 0.1 mg/kg to 150 mg/kg, 0.1 mg/kg to 100 mg/kg, 0.1 mg/kg to 75 mg/kg, 0.1 mg/kg to 50 mg/kg, 0.1 mg/kg to 25 mg/kg, 0.1 mg/kg to 10 mg/kg, 0.1 mg/kg to 5 mg/kg or 0.1 mg/kg to 1 mg/kg. In some aspects the amount of a binding agent can be about 10 mg/kg, 9 mg/kg, 8 mg/kg, 7 mg/kg, 6 mg/kg, 5 mg/kg, 4 mg/kg, 3 mg/kg, 2 mg/kg, 1 mg/kg, 0.9 mg/kg, 0.8 mg/kg, 0.7 mg/kg, 0.6 mg/kg, 0.5 mg/kg, 0.4 mg/kg, 0.3 mg/kg, 0.2 mg/kg, or 0.1 mg/kg. In some embodiments a therapeutically effective amount of a binding agent is between about 0.1 mg/kg to 500 mg/kg, or between about 1 mg/kg and about 300 mg/kg. Volumes suitable for intravenous administration are well known.

In some embodiments a binding agent is used to detect syndecan-1, in vitro or in vivo. In some embodiments a binding agent is used to detect syndecan-1 on a cell surface and/or to determine the presence or absence of a neoplastic cell (e.g., a malignant cell), where the cell expresses syndecan-1. In some embodiments a binding agent is used to determine if a subject has a neoplastic disorder or cancer. In some embodiments a method of detecting syndecan-1 comprises determining the presence or absence of syndecan-1 on a cell in a sample, (e.g., a sample obtained directly or indirectly from a subject). In some embodiments, a method of identifying a cell expressing syndecan-1 comprises (i) contacting the cell with a syndecan-1 binding agent and/or (ii) detecting the presence or absence of a bound complex comprising the syndecan-1 binding agent and the cell, wherein the presence of a bound complex indicates the cell expresses syndecan-1.

Any suitable method can be used to detect and/or quantitate the presence, absence and/or amount of a binding agent specifically bound to syndecan-1, or a portion thereof, non-limiting examples of such methods can be found in Immunology, Werner Luttmann; Academic Press, 2006 and/or Medical Detection and Quantification of Antibodies to Biopharmaceuticals: Practical and Applied Considerations, Michael G. Tovey; John Wiley & Sons, Jul. 12, 2011. Additional non-limiting examples of methods that can be used to detect and/or quantitate the presence, absence and/or amount of a binding agent specifically bound to syndecan-1, or a portion thereof, include use of a competitive immunoassay, a non-competitive immuno assay, western blots, a radioimmunoassay, an ELISA (enzyme linked immunosorbent assay), a competition or sandwich ELISA, a sandwich immunoassay, an immunoprecipitation assay, an immunoradiometric assay, a fluorescent immunoassay, a protein A immunoassay, a precipitin reaction, a gel diffusion precipitin reaction, an immunodiffusion assay, an agglutination assay, a complement fixation assay, an immunohistochemical assay, a Western blot assay, an immunohistological assay, an immunocytochemical assay, a dot blot assay, a fluorescence polarization assay, a scintillation proximity assay, a homogeneous time resolved fluorescence assay, an IAsys analysis, a BIAcore analysis, the like or a combination thereof.

A pharmaceutical composition comprising an amount or dose of a binding agent can, if desired, be provided in a kit, pack or dispensing device, which can contain one or more doses of a binding agent. The pack can for example comprise metal or plastic foil, such as a blister pack. The pack or dispenser device can be accompanied by instructions for administration. The pack or dispenser can also be accompanied with a notice associated with the container in a form prescribed by a governmental agency regulating the manufacture, use, or sale of pharmaceuticals, which notice is reflective of approval by the agency of the form of the drug for human or veterinary administration. Such notice, for example, can be the labeling approved by the U.S. Food and Drug Administration for prescription drugs, or the approved product insert.

In some embodiments a kit or pack comprises an amount of a binding agent sufficient to treat a patient for 1 day to 1 year, 1 day to 180 days, 1 day to 120 days, 1 day to 90 days, 1 day to 60 days, 1 day to 30 days, or any day or number of days there between, 1-4 hours, 1-12 hours, or 1-24 hours.

A kit optionally includes a product label or packaging inserts including a description of the components or instructions for use in vitro, in vivo, or ex vivo, of the components therein. Exemplary instructions include instructions for a diagnostic method, treatment protocol or therapeutic regimen. In certain embodiments, a kit comprises packaging material, which refers to a physical structure housing components of the kit. The packaging material can maintain the components sterilely, and can be made of material commonly used for such purposes (e.g., paper, corrugated fiber, glass, plastic, foil, ampules, vials, tubes, etc.). Product labels or inserts include "printed matter," e.g., paper or cardboard, or separate or affixed to a component, a kit or packing material (e.g., a box), or attached to an ampule, tube or vial containing a kit component. Labels or inserts can additionally include a computer readable medium, optical disk such as CD- or DVD-ROM/RAM, DVD, MP3, magnetic tape, or an electrical storage media such as RAM and ROM or hybrids of these such as magnetic/optical storage media, FLASH media or memory type cards. Product labels or inserts can include identifying information of one or more components therein, dose amounts, clinical pharmacology of the active ingredient(s) including mechanism of action, pharmacokinetics (PK) and pharmacodynamics (PD). Product labels or inserts can include information identifying manufacturer information, lot numbers, manufacturer location, date, information on an indicated condition, disorder, disease or symptom for which a kit component may be used. Product labels or inserts can include instructions for the clinician or for a subject for using one or more of the kit components in a method, treatment protocol or therapeutic regimen. Instructions can include dosage amounts, frequency or duration, and instructions for practicing any of the methods, treatment protocols or therapeutic regimes set forth herein. Kits of the invention therefore can additionally include labels or instructions for practicing any of the methods and uses of the invention described herein. Product labels or inserts can include information on potential adverse side effects and/or warnings.

In certain embodiments, a kit comprises one or more controls having a known amount of syndecan-1. In some embodiments, a kit comprises cells expressing syndecan-1. The cells in the kit can be maintained under appropriate storage conditions until the cells are ready to be used.

In some embodiments, a kit is a diagnostic kits comprising a binding agent. A binding agent comprised in a diagnostic kit can take any suitable form. In some embodiments, a diagnostic comprises a binding agent and a detectable label. In certain embodiments, for example, a diagnostic kit comprises or consists of a stick test, including necessary reagents to perform the method of the invention and to produce, for example, a colorimetric result which can be compared against a color chart or standard curve. A diagnostic kit can also comprise components necessary for detecting a binding agent that specifically binds to syndecan-1, for example a secondary antibody.

Example 1

Examples

Example 1—Generation of Anti-CD138 Antibodies

Monoclonal antibodies were generated against human CD138 that (i) bind with high affinity and specificity, (ii) display rapid internalization, (iii) display cross-reactivity with cynomolgus monkey derived CD138. To generate antibodies, mice (dBalb/C mice; female 6-8 weeks old) were immunized and boosted with a mix of CD138 peptides 1-3 (Fusion 12) or peptides 4-6 (Fusion 13), see Table 11.

These peptides were designed to be distal to glycosylation sites, and in regions that were poorly conserved between human and mouse, but strongly conserved between human and cynomolgus species. Mice were immunized with the indicated peptides which were conjugated to KLH carrier protein following an immunization schedule using Complete Freund's Adjuvant (CFA) for the primary injection and Incomplete Freund's Adjuvant for all the subsequent boosts. Antibody serum titers of the immunized mice were assessed for binding by human CD138 and CD138-Fc binding ELISA. Mice with high titers were selected for fusion. Hybridomas were produced by electrofusion of mouse B cells and SP2/O myeloma cells using an optimized method.

TABLE 11

CD138 peptides used for immunization.

| Peptide 1 | AGEGPKEGEAVVLPEVEPG | SEQ ID NO: 92 |
| Peptide 2 | KEGEAVVLPEVEPGLTARE | SEQ ID NO: 93 |
| Peptide 3 | VVLPEVEPGLTAREQEATP | SEQ ID NO: 94 |
| Peptide 4 | PEPTGLEATTASTSTLP | SEQ ID NO: 95 |
| Peptide 5 | ETTQLPTTHQA | SEQ ID NO: 96 |
| Peptide 6 | ATTAQEPATSHPHRDMQPGHHETS | SEQ ID NO: 97 |

Unlike in traditional methods, cloning of hybridomas was performed simultaneously in a single step wherein fused cells were selected by HAT selection, and single cell colonies were transferred into 96 well plates containing HT media, grown under limited selection and supernatants screened for antigen binding. Positive hybridomas were expanded into larger volumes and the cells were frozen for storage.

Primary Hybridoma FACS Screen on CD138 Positive Cells (H929)

Figure 2B:
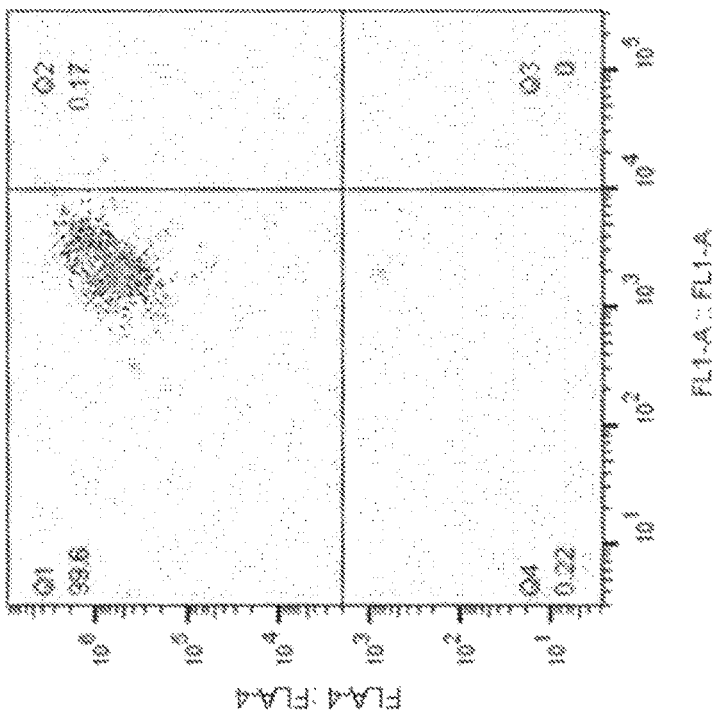

Hybridoma supernatants from Fusion 12 (plates 12-19) were screened by Fluorescence-activated cell sorting (FACS) using 96-well plates containing 20,000 H929 cells per well. H929 cells are a human B-lymphocyte cell line that expresses CD138 on its cell surface. Hybridoma supernatants were added to H929 cells for 1 hour at 4° C. The cells were washed followed by addition of an AlexaFluro 647 anti-mouse antibody and washed again to remove unbound antibody. The cells were analyzed by FACS to detect binding. FACS Data was analyzed by Flowjo software. If supernatant antibodies bound cells at a level 3 standard deviations above the average signal of the plate, they were selected for confirmation FACS and further characterization. A total of 5013 hybridomas from Fusion 12 underwent this primary FACS screen with 134 positive hits; a total hit rate of 2.7% in primary screening. A sample of the positive hybridoma clones from fusion 12 plate 16 is shown in Table 12 below. A FACS histogram of two representative positive hybridoma clones is shown in FIG. 2.

TABLE 12

Table from representative H929 FACS screen showing representative positive hybridomas from fusion 12 plate 16.

| Hybridoma Clone/Antibody Name | Well plate | Well ID | % Q1 | Q1 Geom. Mean | % Q4 | Q4 Geom. Mean | Cells \| Geom. Mean (FL4-A) |
|---|---|---|---|---|---|---|---|
| F12P16A4 | 16 | A4 | 58.3 | 3971 | 41.6 | 1139 | 2363 |
| F12P16B10 | 16 | B10 | 72 | 5051 | 27.8 | 1219 | 3409 |
| F12P16F6 | 16 | F6 | 99.6 | 7.07E+05 | 0.223 | 146 | 6.94E+05 |
| F12P16G3 | 16 | G3 | 64.1 | 4245 | 35.8 | 1136 | 2652 |
| F12P16H6 | 16 | H6 | 58 | 3733 | 41.7 | 1027 | 2182 |

*Geom. Mean indicates the average fluorescence intensity of cells within the indicated quadrant shown in FIG. 2; Q1 indicates positive binding of antibody to H929 cells, while Q4 indicates unbound cells.

Secondary FACS Screen of Fusion 12 Hybridomas

Hybridomas demonstrating positive binding in the primary FACS screening were selected and further characterized. For secondary screening, hybridoma supernatants were assayed by FACS for positive binding to H929 (CD138 expressing) and negative binding to ARH-77 (negative CD138 expression) cells. Negative cells were CSFE stained to help distinguish better positive and negative cell lines. The supernatants were then compared with their non-specific binding versus specific CD138 binding. The results of the representative secondary FACS screen are summarized in Table 13.

TABLE 13

FACS data summary for representative hybridoma clone F12P16F6 (12P16F6) showing positive binding on CP138-positive H292 cells and negative binding on CD138-negative ARH77 cells.

| Hybridoma Clone/Antibody Name | H929 Q1% | H929 GeoMean | % ARH77 (—) | ARH77 Geom. Mean |
|---|---|---|---|---|
| F12P16F6 | 99.32% | 6.46E+05 | 21.85% | 1.12E+04 |

*Geom. Mean indicates the average fluorescence intensity of cells; Q1% indicates the percentage of H929 cells bound by antibody.

Secondary ELISA Screen on Fusion 12 Hybridomas

CD138 and IgG1 isotype ELISAs were also conducted after the secondary screens to help confirm binding specificity and IgG type. CD138 binding ELISA was performed using recombinant CD138-Flag. Data indicated that all FACS-positive hybridomas also bound CD138 by ELISA. The IgG ELISA identified IgG positive antibodies. IgM antibodies were eliminated from further studies. A summary of the selection process to this point is shown in Table 14.

TABLE 14

Summary of primary and secondary screening results.

| Screening Characterization | number of hybridoma clones |
|---|---|
| Total Hybridomas Screened | 5013 |
| Primary Screen hits | 134 |
| No Expression | 39 |
| IgM positive | 23 |
| No Secondary Binding | 60 |
| IgG positive | 72 |
| Secondary FACS binders | 12 |

Experiment 6: Kinetic Binding of Representative Antibodies by SPR

Murine IgGs were purified from the hybridoma supernatants and the IgGs were subject to SPR (surface plasmon resonance) for kinetic binding measurements. Human or mouse CD138 His was immobilized on a GLM chip at 50 pg/mL on a BioRad Proteon. The antibodies were flowed over the bound chip at a rate of 30 µl/min at a concentration range of 167 nM to 10.4 nM to detect kinetic binding. KDs were measured using bivalent analyte fit. Kinetic results are shown in Table 15 and FIG. 3.

TABLE 15

SPR kinetic measurement for representative antibodies.

| Antibody Name | hCD138 ka (1/Ms) | hCD138 kd (1/s) | hCD138 KD | hCD138 KD (nM) | mCD138 KD (nN) |
|---|---|---|---|---|---|
| mBT062 | $3.42 \times 10^5$ | $6.66 \times 10^{-4}$ | $1.95 \times 10^{-9}$ | 2.0 | NB |
| F13P30A7 | $2.38 \times 10^5$ | $1.27 \times 10^{-3}$ | $5.32 \times 10^{-9}$ | 5.3 | NA |
| F12P16F6 | $5.57 \times 10^4$ | $1.17 \times 10^{-3}$ | $2.10 \times 10^{-8}$ | 21.0 | NB |
| F13P18D8 | $2.78 \times 10^5$ | $5.23 \times 10^{-4}$ | $1.88 \times 10^{-9}$ | 1.9 | NA |
| F12P7G11 | $3.81 \times 10^6$ | $3.30 \times 10^{-2}$ | $8.66 \times 10^{-9}$ | 8.6 | NB |
| E13P14D3 | $1.07 \times 10^5$ | $1.04 \times 10^{-3}$ | $9.67 \times 10^{-9}$ | 9.7 | NA |
| F11AP11E5 | $1.28 \times 10^5$ | $1.17 \times 10^{-2}$ | $9.16 \times 10^{-8}$ | 91.6 | NB |
| F12P18D4.a | $6.31 \times 10^5$ | $1.8 \times 10^{-2}$ | $2.86 \times 10^{-8}$ | 28.6 | 672 |

*NB = No binding;

NA = Not Analysed.

**Those marked NA were not analyzed by SPR but were shown to not cross-react with mouse CD138 via an ELISA binding assay (data not shown).

TABLE 16

CDRs of the antibodies

| Antibody | CDR-L1 SEQ ID NOs | CDR-L2 SEQ ID NOs | CDR-L3 SEQ ID NOs | CDR-H1 SEQ ID NOs | CDR-H2 SEQ ID NOs | CDR-H3 SEQ ID NOs |
|---|---|---|---|---|---|---|
| F12P16F6 | 2 or 3 | 16, 17 or 18 | 27 or 28 | 46 or 47 | 56 or 57 | 68 or 69 |
| F13P30A7 | 4 or 5 | 19, 20 or 21 | 29 or 30 | 48 or 49 | 58, 59 or 60 | 70 or 71 |
| F13P18D8 | 6 or 7 | 22 | 31 | 50 | 58, 59 or 60 | 72 |
| F12P7G11 | 8 or 9 | 23 | 32 | 51 | 61 or 62 | 73 |
| F13P14D3 | 10 or 11 | 24 | 29 or 30 | 52 | 58, 60 or 63 | 74 |
| F11AP11E5 | 12 or 13 | 25 | 33 | 53 | 64 or 65 | 75 |
| F12P18D4.a | 14 or 15 | 26 | 34 | 54 or 55 | 66 or 67 | 76 |

Antibody Expression

Expression of two representative chimeric antibodies were assessed to determine the potential for scale-up production. Expi293 cells (250 mL) were transiently transfected with a vector directing the expression of 12P16F6 hIgG1 (also referred to as chF6) or 13P30A7 hIgG1 (also referred to as chP30a7). The chimeric antibody 12P16F6 hIgG1 includes the murine heavy chain variable region (SEQ ID NO:77) and light chain variable region (SEQ ID NO:35) of F12P16F6 and constant regions of human IgG$_1$, kappa isotype. The chimeric antibody 13P30A7 hIgG1 includes the murine heavy chain variable region (SEQ ID NO:78) and light chain variable region (SEQ ID NO:36) of F13P30A7 and constant regions of human IgG1, kappa isotype. The results are summarized in Table 17 below. The expressed antibodies were also analyzed by SDS-PAGE and size exclusion chromatography (data not shown).

TABLE 17

| Name | Transfection Volume (mL) | Purification Lot# | [Conc] (mg/mL) | Volume (mL) | Total Yield (mg) | Endotoxin (Eu/mg) |
|---|---|---|---|---|---|---|
| 12P16F6 hIgG1 | 250 mL | AB150616-F6 | 2.21 | 3.2 | 7.07 | <4.5 |
| 13P30A7 hIgG1 | 250 mL | AB150616-A7 | 1.02 | 1.05 | 1.07 | <9.8 |

Cynomolgus Cross-Reactivity of Representative Antibodies.

Figure 4A:
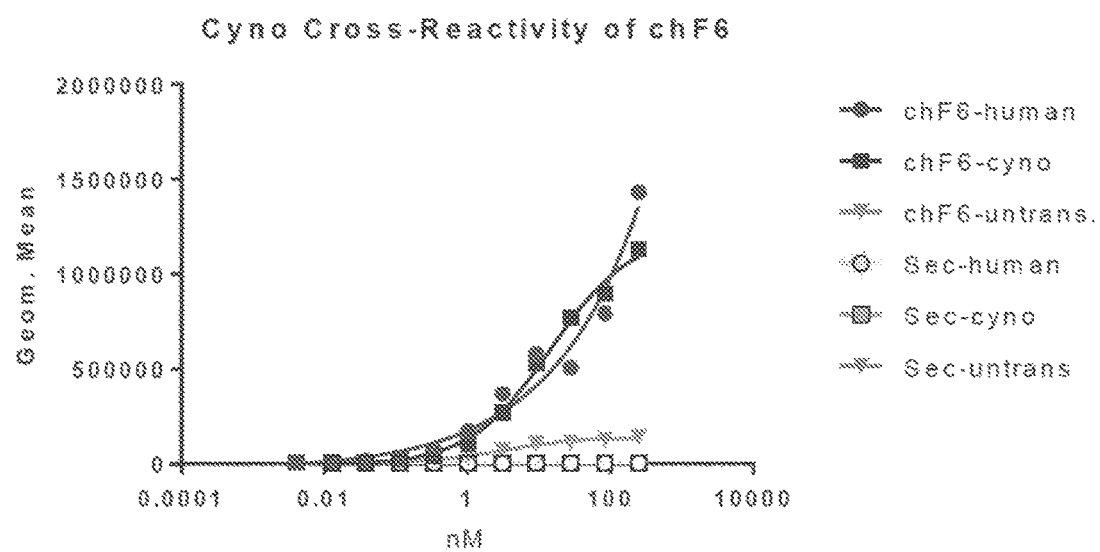
FIG. 4 shows binding of representative chimeric antibodies 12P16F6 hIgG1 (chF6, FIG. 4A) and 13P30A7 hIgG1 (chP30A7, FIG. 4B) to human CD138 expressing cells (human) and cynomolgus CD138 expressing cells (cyno). Control antibody (Sec) showed little or no specific binding to CD138.
Figure 4B:
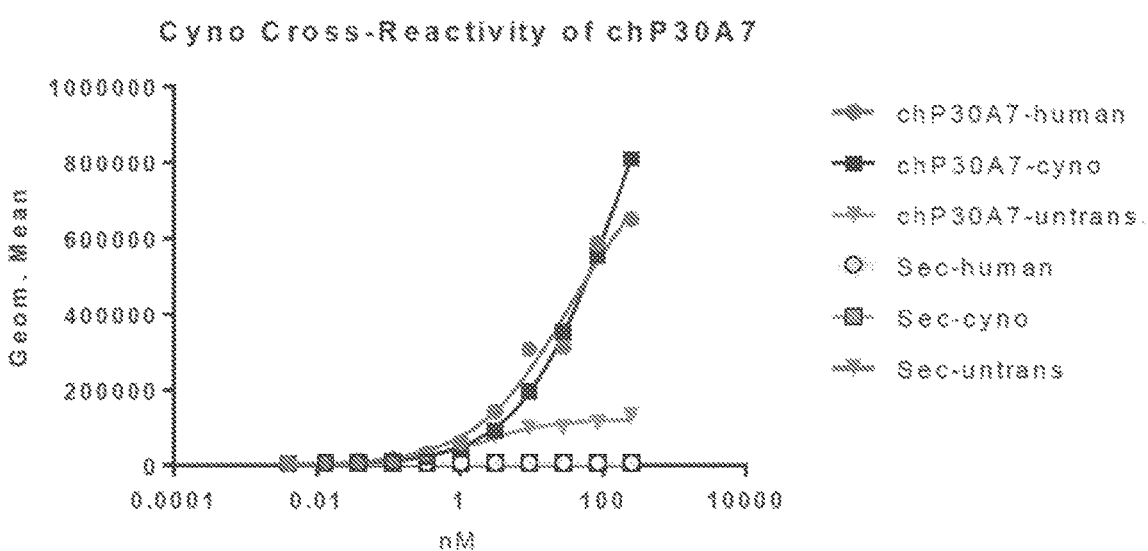

12P16F6 hIgG1 or 13P30A7 hIgG1 were tested for cross-reactivity to cynomolgus monkey CD138. Antibodies that cross-react with CD138 from cynomolgus monkey (cyno) have an advantage that they can be tested for toxicity in this strain of non-human primate prior to conducting efficacy trials. Briefly, a vector directing the cell-surface expression of human CD138 or cyno CD138 was transfected in Expi293 cells. Binding of 12P16F6 hIgG1 and 13P30A7 hIgG1 to transfected Expi293 cells was tested at 3-fold dilutions starting at 33.3 µg/ml. Secukinumab (Sec) was used as a negative control to ensure the transfected cells did not have any background binding. Representative antibodies 12P16F6 hIgG1 and 13P30A7 hIgG1 showed specific binding to both human and cyno CD138 (FIG. 4).

TABLE 18

Summary of data for representative CD138 hybridoma-derived antibodies.

| Antibody Name | SPR mCD138 KD (nM) | SPR hCD138 KD (nM) |
|---|---|---|
| mBT062 IgG2a | NB | 2 |
| 13P30A7 | NA | 5 |

TABLE 18-continued

Summary of data for representative CD138 hybridoma-derived antibodies.

| Antibody Name | SPR mCD138 KD (nM) | SPR hCD138 KD (nM) |
|---|---|---|
| 12P16F6 | NB | 21 |
| 13P18D8 | NA | 2 |
| 12P7G11 | NB | 9 |
| 13P14D3 | NA | 10 |
| 11AP11E5 | NB | 92 |
| 12P18D4.a | 672 | 29 |

Definitions of Certain Reagents and Materials Used in Example 1

Note that the name of a hybridoma clone here can refer to either the hybridoma cells or the antibody produced from the hybridoma cells, depending on the context in which the name is used. The name of a hybridoma clone often refers to the fusion (e.g., fusion #12 or #13, abbreviated F12 and F13 respectively), followed by the plate number preceded by the letter "P", and the well number. For example, the hybridoma clone F12P16F6 (also referred to herein as 12P16F6 or P16F6), refers to an antibody obtained from a hybridoma derived from Fusion 12, plate 16, and well F6. mBT-062 is an IgG1, CD138 binding control antibody.

Example 2

Example 2—Humanization

A strategy was developed to design and create humanized versions of the murine anti-CD138 antibodies described herein where the humanized version of the antibody retains the properties of the parental monoclonal antibody. Provided herein are examples of humanizing the mouse monoclonal anti-CD138 antibody designated as F12P16F6.

The humanized versions of F12P16F6 generated herein were often benchmarked against the chimeric antibody 12P16F6 IgG1. Other positive and negative controls were also used where appropriate.

Five humanization strategies were employed in parallel which resulted in the generation of three humanized F12P16F6 light chain sequences and four humanized F12P16F6 heavy chain sequences. In general, the methods involve grafting of the murine complementarity determining regions (CDRs) onto human framework and constant regions. Each of the three light and four heavy chains were expressed in combination with each other, and purified, which resulted in a total of twelve humanized anti-CD138 monoclonal antibodies. The humanized antibodies were analyzed for their expression/purification profiles, biophysical properties, binding to a CD138 peptide antigen, binding to native CD138, and specificity. Representative humanized antibodies were also evaluated for other biophysical properties.

Methods

Expression and Purification of chP16F6

A vector directing the expression of the chimeric antibody chP16F6 was transfected in a volume of 250 ml into Expi293 cells using EXPIFECTAMINE(Trademark) 293 Transfection Kit. The supernatant was purified utilizing pH dependent, protein A purification. The chimeric antibodies were purified using HiTrap MabSelect SuRe 5 ml. After purification, the antibodies were buffer exchanged into 1×DPBS using zeba spin columns. The recovery of chP16F6 was 7.1 mg at 2.21 mg/mL.

Humanization of F12P16F6.

Humanization of the heavy and light chain variable domains was performed using a method selected from (i) CDR grafting (designated as cdr) which was performed according to Jones et al. (1986) "Replacing the complementarity determining regions in a human antibody with those from a mouse" Nature 321:522-525 and Verhoeyen et al. (1988) "Reshaping human antibodies: grafting an anti-lysozyme activity" Science 239:1534-1536, where the CDRs as defined by Kabat et al. (1991) "Sequences of Proteins of Immunological Interest" 5th ed. US Department of Health and Human Services, Public Health Service, National Institutes of Health (NIH Publication No 91-3242), are grafted onto an appropriate human scaffold, while the critical framework residues are preserved; (ii) Grafting of abbreviated CDRs (designated as abb) which was performed according to Padlan et al. (1995) "Identification of specificity-determining residues in antibodies" FASEB J 9:133-139 were abbreviated CDRs, defined as residues 27D-34, 50-55, and 89-96 in the light chain, and 31-35B, 50-58, and 95-101 in the heavy chain, are grafted onto an appropriate human scaffold while the critical framework residues are preserved; (iii) SDR-transfer (designated as sdr) which was performed according to Padlan et al. (1995) "Identification of specificity determining residues in antibodies" FASEB J 9:133-139 where the residues that could be involved in antigen binding, are transplanted into an appropriate human sequence while the critical framework residues are preserved; (iv) The Frankenstein approach (designated as fra) which was perform according to Wu and Kabat (1992) "Possible use of similar framework region amino acid sequences between human and mouse immunoglobulins for humanizing mouse antibodies" Mol Immunol 29:1141-1146 where the CDRs are grafted onto a human scaffold made up of individual framework regions coming from appropriate human antibodies while the critical framework residues are preserved; and (v) Veneering (designated as ven) which was performed according to Padlan (1991) "A possible procedure for reducing the immunogenicity of antibody variable domains while preserving their ligand-binding properties" Mol Immunol 28:489-498 where the residues which are exposed in the nonhuman antibody, if the structure is known, or in a homologous molecule, if the structure is not known, are changed to the corresponding residues from an appropriate human antibody while the CDRs and the critical framework residues are preserved. In all of the methods described, 'an appropriate human antibody' is used to denote the closest human sequence (available in GenBank). The term "critical framework residue" is used to denote a residue that is deemed essential for the maintenance of three-dimensional structure (from the analysis of relevant high-resolution X-ray structures in the PDB). Sometimes a second "repaired" round of humanization was performed to improve the SEC profile of the antibody. Humanized antibodies produced in a second round are indicated by the designation rep or repair. The amino acid sequences of the resulting humanized heavy and light chain variable regions are shown in FIGS. 10A and 10B, respectively.

Expression and Purification of Humanized P16F6 Repaired Constructs

Each of the four humanized heavy chains was paired with each of the 3 light chains to yield 12 different antibodies (Table 19). The 12 humanized P16F6 antibodies were expressed in Expi293 cells using EXPIFECTAMINE(Trademark) 293 Transfection Kit. All constructs were transfected in a volume of 125 ml except F6 cks-rep (more was needed for additional studies) and 375 ml of F6 f2ka-rep due to low protein expression. The supernatants were filtered through a 0.22 μm filter and treated with a protease inhibitor. Antibodies providing an expression level of >5 mg/L after buffer exchange and the ability to concentrate above ≥1 mg/mL were selected for further analysis.

TABLE 19

| Antibody Name | Heavy Chain Variable Region Name (SEQ ID) | Light Chain Variable Region Name (SEQ ID) |
|---|---|---|
| F6 aka-zap | P16F6 abb/sdr-rep (SEQ ID NO: 84) | P16F6 abb-rep (SEQ ID NO: 43) |
| F6 akf-rep | P16F6 abb/sdr-rep (SEQ ID NO: 84) | P16F6 fra-rep (SEQ ID NO: 44) |
| F6 aks-rep | P16F6 abb/sdr-rep (SEQ ID NO: 84) | P16F6 sdr/cdr/ven-rep (SEQ ID NO: 42) |
| F6 cka-rep | P16F6 cdr/ven-rep (SEQ ID NO: 85) | P16F6 abb-rep (SEQ ID NO: 43) |
| F6 ckf-rep | P16F6 cdr/ven-rep (SEQ ID NO: 85) | P16F6 fra-rep (SEQ ID NO: 44) |
| F6 cks-rep | P16F6 cdr/ven-ren (SEQ ID NO: 85) | P16F6 sdr/cdr/ven-rep (SEQ ID NO: 42) |
| F6 f1ka-rep | P16F6 fra1-rep (SEQ ID NO: 86) | P16F6 abb-rep (SEQ ID NO: 43) |
| F6 f1kf-rep | P16F6 fra1-rep (SEQ ID NO: 86) | P16F6 fra-rep (SEQ ID NO: 44) |
| F6 f1ks-rep | P16F6 fra1-rep (SEQ ID NO: 86) | P16F6 sdr/cdr/ven-rep (SEQ ID NO: 42) |
| F6 f2ka-rep | P16F6 fra2-rep (SEQ ID NO: 87) | P16F6 abb-rep (SEQ ID NO: 43) |
| F6 f2kf-rep | P16F6 fra2-rep (SEQ ID NO: 87) | P16F6 fra-rep (SEQ ID NO: 44) |
| F6 f2ks-rep | P16F6 fra2-rep (SEQ ID NO: 87) | P16F6 sdr/cdr/ven-rep (SEQ ID NO: 42) |

*F6 and P16F6 indicates that the humanized antibody chains were derived from F12P16F6.

The antibodies were purified utilizing pH dependent, protein A purification (HiTrap MabSelect SuRe 5 mL). After purification, the antibodies were buffer exchanged into 1×DPBS using zeba spin columns. The recovery and relative stability as determined by size exclusion chromatography (SEC) analysis varied between the humanized antibodies (SEC profiles not shown). Table 20 summarizes the recovery, concentration and the percent monomer as determined by SEC. An SDS-PAGE analysis of eleven representative humanized antibodies is shown in FIG. 6. The nomenclature sometimes takes the form of hF6 xky-rep where h stands for humanized, F6 stands for F12P16F6-derived, x stands for the first letter of the first procedure used to generate the humanized heavy chain sequence (a=abb, s=sdr, f=fra, c=cdr), k stands for kappa light chain, and y stands for the first letter of the first procedure used to generate the humanized light chain sequence (a=abb, s=sdr, f=fra, c=cdr). The term "rep" stands for "repaired" indicating that at least a second round of humanization was performed, often using a different method.

TABLE 20

| Antibody Name | Final Recovery (mg) | Concentration (mg/ml) | Recovery (mg/ml) | SEC % Monomer |
|---|---|---|---|---|
| F6 aka-rep | 1.2 | 1.44 | 9.6 | 75.2 |
| F6 akf-rep | 3.28 | 1.13 | 26.24 | 95.4 |
| F6 aks-rep | 4.89 | 1.63 | 39.12 | 95.2 |
| F6 cka-rep | 1.72 | 1.23 | 13.76 | 88.8 |
| F6 ckf-rep | 8.4 | 1.05 | 67.2 | 95.3 |
| F6 cks-rep | 15.25 | 1.22 | 68.8 | 99.3 |
| F6 f1ka-rep | 0.79 | 1.08 | 6.32 | 92.9 |
| F6 f1kf-rep | 2.86 | 1.1 | 22.88 | 94.3 |
| F6 f1ks-rep | 3.5 | 1.25 | 28 | 95.6 |
| F6 f2ka-rep (Lot 1) | 0.37 | 1.06 | 2.96 | 79.1 |
| F6 f2ka-rep (Lot 2) | 0.71 | 1.23 | 2.84 | 95 |
| F6 f2kf-rep | 1.8 | 1.8 | 14.4 | 95.1 |
| F6 f2ks-rep | 2.81 | 1.34 | 22.48 | 77.6 |

CD138 Binding of Humanized P16F6 Repaired Constructs by FACS

Figure 7A:
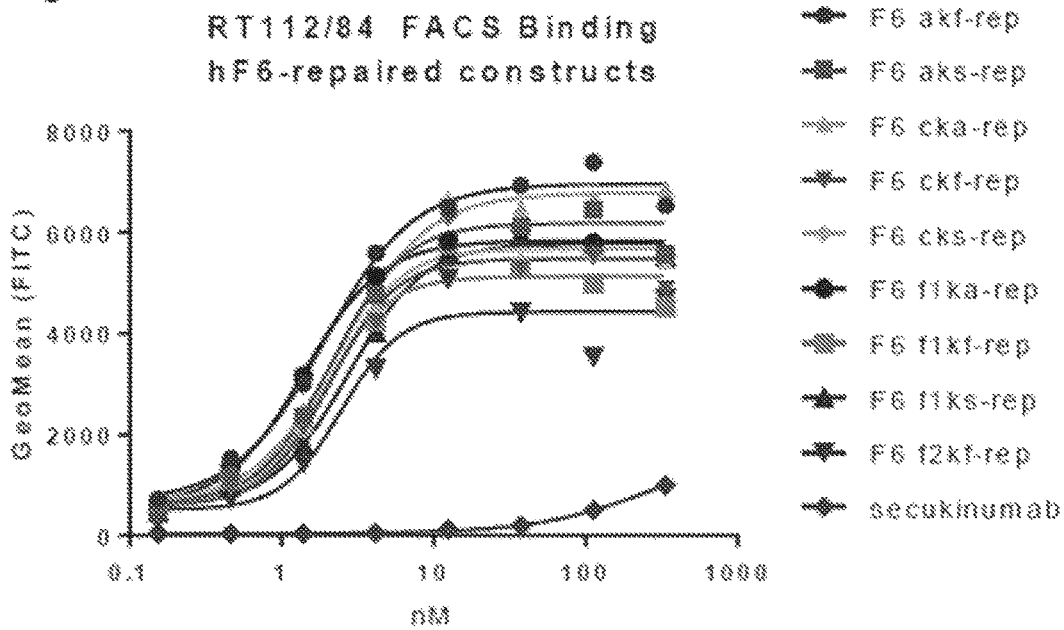
FIG. 7 shows FACS analysis of cell-surface binding of eleven representative humanized antibodies to human CD138 on the surface of multiple myeloma cell line KMS-11 (FIG. 7B) and bladder cancer line RT112/84 (FIG. 7A). Secukinumab was used as a negative control.
Figure 7B:
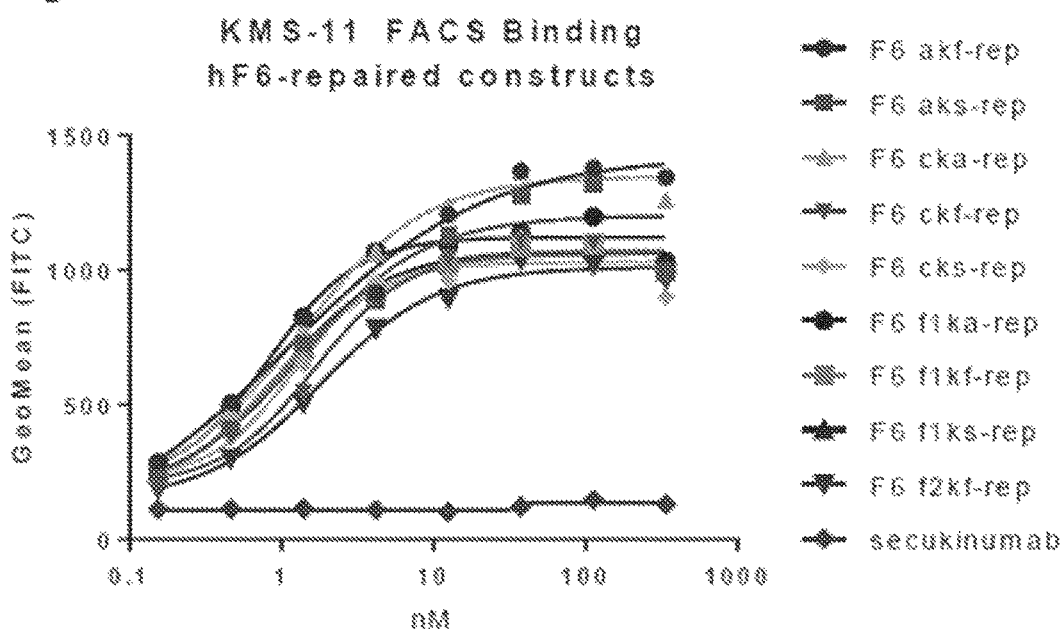

Analysis of cell-surface binding to human CD138 was performed on 9 representative humanized anti-CD138 antibodies by FACS (FIG. 7). Secukinumab was used as a negative control. Two cell lines expressing moderate levels of CD138 were used to test binding; multiple myeloma cell line KMS-11 and bladder cancer line RT112/84. In previous experiments, 12P16F6 hIgG1 showed an EC50 of approximately 9 nM in RT-122/84 cells and ~3 nM in KMS-11 cells. EC50s were calculated using four parameter fit curves (Table 21). The constructs were also tested against ARH-77 cells, which are CD138 negative lymphoblasts. NB indicates no specific binding observed.

TABLE 21

Calculated EC50 values of binding to endogenous CD138

| Antibody Name | KMS-11 | RT-112 | ARH-77 |
|---|---|---|---|
| F6 akf-rep | 1.09 | 1.88 | NB |
| F6 aks-rep | 1.36 | 2.13 | NB |
| F6 cka-rep | 1.30 | 2.44 | NB |
| F6 ckf-rep | 1.64 | 2.09 | NB |
| F6 cks-rep | 1.2 | 2.2 | NB |
| F6 f1ka-rep | 0.83 | 1.39 | NB |
| F6 f1kf-rep | 0.94 | 1.93 | NB |
| F6 f1ks-rep | 0.97 | 2.73 | NB |
| F6 f2kf-rep | 1.81 | 2.46 | NB |
| secukinumab | NB | NB | — |

CD138 Binding ELISA of Humanized P16F6 Repaired Constructs.

A CD138 binding ELISA was performed with 9 representative humanized antibodies to determine binding to portion of the linear CD138 peptide used for immunization (FIG. 7). Plates were coated with the hCD138 peptide (AGEGPKEGEAVVLP; SEQ ID NO:89) and a negative control peptide (QAAVTSHPHGGMQPGLHETSA; SEQ ID NO:98), or a mouse CD138 peptide for which F12P16F6 does not bind. Coated plates were incubated with various dilutions of each of the 9 representative antibodies overnight and binding was detected with a goat anti-human IgG (H+L)-HRP. EC50s were determined using four parameter fit curves (Table 22). An ELISA was also performed to detect binding to plate-coated human CD138-Fc protein (Table 22). The analysis and results were similar.

TABLE 22

| Antibody Name | hCD138 peptide EC50 (nM) | hCD138-Fc EC50 (nM) |
|---|---|---|
| 12P16F6 hIgG1 | 0.599 | 0.4715 |
| F6 akf-rep | 1.54 | 0.8791 |
| F6 aks-rep | 1.285 | 0.9694 |
| F6 cka-rep | 1.654 | 0.8549 |
| F6 ckf-rep | 0.9812 | 0.5354 |
| F6 cks-rep | 0.3299 | 0.1974 |
| F6 f1ka-rep | 0.7443 | 0.433 |
| F6 f1kf-rep | 0.4133 | 0.2247 |
| F6 f1ks-rep | 1.314 | 0.7616 |
| F6 f2kf-rep | 0.7257 | 0.4051 |

Summary of Selected Study Results

Table 23 shows a summary of the analytic results for 13 representative humanized anti-CD138 monoclonal antibodies.

TABLE 23

Summary of biophysical characteristics of representative humanized antibodies.

| Antibody Name | Recovery (mg/L) | SEC % monomer | FACS binding (KMS11) | ELISA CD138 Fc binding |
|---|---|---|---|---|
| F6 aka-rep | 9.6 | 75.2 | — | — |
| F6 akf-rep | 26.24 | 95.4 | 1.09 | 0.8791 |
| F6 aks-rep | 39.12 | 95.2 | 1.36 | 0.9694 |
| F6 cka-rep | 13.76 | 88.8 | 1.30 | 0.8549 |
| F6 ckf-rep | 67.2 | 95.3 | 1.64 | 0.5354 |
| F6 cks-rep | 68.8 | 99.3 | 1.20 | 0.1974 |
| F6 f1ka-rep | 6.32 | 92.9 | 0.83 | 0.433 |
| F6 f1kf-rep | 22.88 | 94.3 | 0.94 | 0.2247 |
| F6 f1ks-rep | 28 | 95.6 | 0.97 | 0.7616 |
| F6 f2ka-rep (lot 1) | 2.96 | 79.1 | — | — |
| F6 f2ka-rep (lot 2) | 2.84 | 95 | — | — |
| F6 f2kf-rep | 14.4 | 95.1 | 1.81 | 0.4051 |
| F6 f2ks-rep | 22.48 | 77.6 | — | — |

Example 3

Example 3—Determination of Crystal Structure

The X-ray crystal structure of a human syndecan-1 peptide in complex with a humanized anti-CD138 antibody Fab fragment was solved at 1.95 Å resolution. The structure included one copy each of syndecan-1 peptide and Fab per asymmetric unit (FIG. 8).

Structure Description

The humanized antibody Fab comprises the humanized heavy chain variable region (SEQ ID NO: 84) and the humanized light chain variable region (SEQ ID NO:42). The CDR canonical structures were analyzed in accordance with the PyIgClassify database. The heavy chain CDRs were classified as follows: H1-13-1 (CDR-length-cluster), H2-10-1 and H3-6-1. The light chain CDRs were classified as follows: L1-16-1, L2-8-1 and L3-9-cis7-1. Syndecan-1 peptide binds to a single Fab, and complex formation buries 540 Å2 of the solvent-accessible surface areas of syndecan-1 peptide and Fab (313.6 Å2 chains A and H; 226.4 Å2 chains A and L).

All visible syndecan-1 peptide residues from 98-108 participate in direct contacts with Fab (FIG. 8). The specific Fab residues involved in the interface are 31-33, 35, 47, 50, 52, 58, 94-96 and 101-102 from chain H and 27-28, 32, 34, 46, 49-50, 89-94 and 96 from chain L. This means that four residues from CDR H1 participate in the interface, along with three residues from CDR H2 and five residues from CDR H3. In addition, four residues from CDR L1, two residues from CDR L2 and seven residues from CDR L3 participate in the interface.

A 1 mL aliquot of Fab at 5.88 mg/mL (approx. 125 µM) was mixed with 250 µM syndecan-1 peptide (AGEGPKEG-EAVVLP; SEQ ID NO:89) and incubated at 4° C. for two hours. The complex was fractionated on an 5200 size exclusion column which had been pre-equilibrated with buffer containing 20 mM Tris pH 7.5 and 150 mM NaCl. Peak fractions were pooled and concentrated for crystallization. The final protein concentration as determined by Bradford assay was 3 mg/mL.

Approximately 400 crystallization conditions were screened by the hanging drop method of vapour diffusion in 96 well format using a mosquito robot (TTP Labtech). Crystal growth was observed at 20° C. in two conditions: 2.1 M DL-malic acid pH 7.0, and 60% Tacsimate pH 7.0. Crystallization was optimized further in 24 well format.

Crystal Cooling and Data Collection

The crystal described was grown using the hanging drop method of vapour diffusion in a 24 well plate with a precipitant solution containing 1.7 M DL-Malic acid, pH 7.0. In house X-ray diffraction screening indicated that resolution could be improved by pre-soaking crystals in a solution containing 3.0 M DL-Malic acid, pH 7.0 for 24 hours. The crystal was cryo-cooled by capturing it in a loop directly from the soaking drop and plunging it into liquid nitrogen. A synchrotron data set was collected at ESRF beamline ID30A-1.

Structure Solution and Refinement

Data processing in MOSFLM (CCP4) and AIMLESS (CCP4) indicated that the most likely space group was P212121 with unit cell dimensions a=60.6 Å, b=132.9 Å and c=51.2 Å, giving a total cell volume of 411706.34 Å. Calculation of the Matthews coefficient (2.14 Å3/Da and 42.7% solvent content) indicated that there was most probably one complete Fab-syndecan-1 complex per asymmetric unit. Models for use in molecular replacement (MR) were chosen by BLAST searching the sequences of each component (Fab heavy and light chains) against the PDB. Models with highest sequence identity were 3sqo (Fab heavy chain) and 4ojf (Fab light chain). The large number of Fab crystal structures deposited in the PDB has revealed a wide variety in elbow angles present between variable and constant domains. This variation in elbow angles can cause the overall tertiary structure of two otherwise highly homologous Fab fragments to be significantly different, which in turn causes MR to fail. For this reason the hinge regions between the variable and constant domains of the heavy and light chains were removed to create four separate MR search ensembles (VH, VL, CH and CL). Amino acid residues were trimmed from the CDRs of the heavy and light variable domain models after visual inspection in COOT to prevent any potential clashes that might also cause MR to fail. All four of the input search ensembles (VH, VL, CH and CL) that were required to build a complete Fab were correctly located by MR using PHASER (McCoy et al., 2007) (CCP4). The MR output model was given 20 cycles of jelly body refinement using REFMAC5 (CCP4). The protein sequence was mutated to match that of Fab using CHAIN-SAW(CCP4). The model was improved iteratively through successive cycles of model building and refinement until all of the ordered regions of Fab visible in the electron density maps were complete. The heavy and light chain amino acids were renumbered in accordance with the Kabat antibody numbering convention. Electron density corresponding to the syndecan-1 peptide was clearly visible. Syndecan-1 amino acid residues were added by hand in COOT and the correct numbering was applied. Water molecules were added using the water placement option in COOT and the complete model was refined using REFMAC5 (CCP4). The final Fab model contained heavy chain residues 1-216 (chain H) and light chain residues 1-212 (chain L) with no breaks in either chain. The final syndecan-1 model contained residues 98-108 (chain A). The final model also contained 205 water molecules. Final Rwork=21.2%, Rfree=26.1%.

TABLE 24

| Data collection and processing statistics | |
|---|---|
| Synchrotron, Beam line | ESRF, ID30A-1 |
| Date and time of data collection | 28 Jan. 2017, 04:13:17 |
| Wavelength (Å) | 0.966 |
| Detector type | Dectris Pilatus3 2M |
| Transmission (%) | 100 |
| Temperature (K) | 100 |
| Exposure time (s) | 0.1 |
| Oscillation range per frame (*) | 0.2 |
| Overall rotation (*) | 180 |
| Resolution range (Å) | 44.76-1.95 |
| Number of observed reflections | 197864 |
| Number of unique reflections | 30915 |
| Multiplicity (overall and last shell) | 6.4 (6.1) |
| Completeness (%) (overall and last shell) | 99.9 (99.9) |
| Rmerge (%) (overall and last shell) | 12.0 (92.1) |
| Mean I/aigma (overall and last shell) | 12.1 (1.1) |
| CC (1/2) (overall and last shell) | 0.996 (0.592) |
| Space group | P212121 |
| Unit cell parameters (Å), (*) | 60.57 132.87 51.16 90.00 90.00 90.00 |
| Refinement statistics | |
| Refinement program | REFMAC5 |
| Resolution range (Å) | 66.43-1.95 |
| Number of reflections (working/test) | 23294/1561 |
| Rwork (%) | 21.2 |
| Rfree (%) | 26.1 |
| Protein residues modelled | 435 |
| Number of protein atoms modelled | 3324 |
| Number of water atoms modelled | 205 |
| RMSD Bond lengths (Å) | 0.007 |
| RMSD Bond angles (*) | 1.289 |
| Mean overall B value (Å2) | 28.9 |
| Ramachandran plot favoured (%) | 96.8 |
| Ramachandran plot allowed (%) | 3.2 |
| Ramachandran plot outlier region (%) | 0.0 |

Example 4

Example 4-Certain Representative Syndecan-1 (CD138) Sequences

Human syndecan-1 (syndecan-1)-UniProtKB-P18827
SEQ ID NO: 1
MRRAALWLWLCALALSLQPALPQIVATNLPPEDQDGSGDDSDNFSGSGAGALQDITLSQQTPST

WKDTQLLTAIPTSPEPTGLEATAASTSTLPAGEGPKEGEAVVLPEVEPGLTAREQEATPRPRET

TQLPTTHLASTTTATTAQEPATSHPHRDMQPGHHETSTPAGPSQADLHTPHTEDGGPSATERAA

EDGASSQLPAAEGSGEQDFTFETSGENTAVVAVEPDRRNQSPVDQGATGASQGLLDRKEVLGGV

IAGGLVGLIFAVCLVGFMLYRMKKKDEGSYSLEEPKQANGGAYQKPTKQEEFYA

Mouse syndecan-1 (syndecan-1)-UniProtKB-P18828
SEQ ID NO: 99
MRRAALWLWLCALALRLQPALPQIVAVNVPPEDQDGSGDDSDNFSGSGTGALPDTLSRQTPSTW

KDVWLLTATPTAPEPTSSNTETAFTSVLPAGEKPEEGEPVLHVEAEPGFTARDKEKEVTTRPRE

TVQLPITQRASTVRVTTAQAAVTSHPHGGMQPGLHETSAPTAPGQPDHQPPRVEGGGTSVIKEV

VEDGTANQLPAGEGSGEQDFTFETSGENTAVAAVEPGLRNQPPVDEGATGASQSLLDRKEVLGG

VIAGGLVGLIFAVCLVAFMLYRMKKKDEGSYSLEEPKQANGGAYQKPTKQEEFYA

Rat syndecan-1 (syndecan-1)-UniProtKB-P26260
SEQ ID NO: 100
MRRAALWLWLCALALRLQPALPQIVTANVPPEDQDGSGDDSDNFSGSGTGALPDMTLSRQTPST

WKDVWLLTATPTAPEPTSRDTEATLTSILPAGEKPEEGEPVAHVEAEPDFTARDKEKEATTRPR

ETTQLPVTQQASTAARATTAQASVTSHPHGDVQPGLHETLAPTAPGQPDHQPPSVEDGGTSVIK

EVVEDETTNQLPAGEGSGEQDFTFETSGENTAVAGVEPDLRNQSPVDEGATGASQGLLDRKEVL

GGVIAGGLVGLIFAVCLVAFMLYRMKKKDEGSYSLEEPKQANGGAYQKPTKQEEFYA

*Macaca mulatta* (Rhesus macaque) syndecan-1-UniProtKB-A0A1D5RIX8
SEQ ID NO: 101
MGATAYIPNSNSLSALLRGLELPHQTELLRVRALPTLLCPCALCRAPGCVQIVATNLPPEDQDG

SGDDSDNFSGSGAGALQDITLSQQTPSTWKDTWLLTATPMSPEPTGLEATAASTSTLPAGEGPK

EGEAVVLLEVEPDLTAREQEATPQPTETTQLPTTHQAPTARATTAQEPATSHPHRDMQPGHHET

SAPAGPGQADLHTPRTEDGGPSATERAAEDGASSQLPAAEGSGEQDFTFETSGENTAIVAVEPD

HRNQSPVDPGATGASQGLLDRKEVLGGIIAGGLVGLIFAVCLVGFMLYRMKKKDEGSYSLEEPK

QANGGAYQKPTKQEEFYA

*Canis lupus familiaris* (Dog) (*Canis familiaris*) syndecan-1-UniProtKB-E2R170
SEQ ID NO: 102
MRRAALWLWLCALALRLQPALPQIVATNVPPEDQDGSGDDSDNFSGSGAGALQDITLSQQTPST

WKDMALLTAMPTAQEPTGADDIDSSTSILLTREGPEGGEAVLVAEAEPGFTDREKETAHPPSET

TPHPTTHRASTARATTAQGPATLHPHRDAQPDHHQISVLAEPSQLDPHTPRVEDGGPSATERAA

EDGVSTQLPAGEGSGEQDFTFDVSGENTAGTAVEPDQRNQPPVDRGATGASQGLLDRKEVLGGV

IAGGLVGLIFAVCLVGFMLYRMKKKDEGSYSLEEPKQANGGAYQKPSKQEEFYA

*Macaca fascicularis* (Cynomolgus Monkey) Syndecan-1
SEQ ID NO: 103
MRRAALWLWLCALALSLQPAMPQIVATNLPPEDQDGSGDDSDNFSGSGAGALQDITLSQQTPST

WKDTWLVRATPMSPEPTGLEATAASTSTIQAGEGPKEGEAVVLLEVEPDLTAREQEATPQPTET

TQLPTTHQAPTARATTAQEPATSHPHRDMQPGHHETSAPAGPGQADLHTPRTEDGGPSATERAA

-continued

```
EDGASSQLPAAEGSGEQDFTFETSGENTAIVAVEPDHRNQSPVDPGATGASQGLLDRKEVLGGI

IAGGLVGLIFAVCLVGFMLYRMKKKDEGSYSLEEPKQANGGAYQKPTKQEEFYA
```

Example 5

Example 5—Certain Embodiments

A1. A binding agent that specifically binds to syndecan-1, or a portion thereof, wherein the binding agent comprises a CDR-L1, CDR-L2 and a CDR-L3, each independently selected from a light chain variable domain selected from Table 1, Table 2 and Table 3.

A2. A binding agent that specifically binds to syndecan-1, or a portion thereof, wherein the binding agent comprises a CDR-H1, CDR-H2 and a CDR-H3, each independently selected from a heavy chain variable domain selected from Table 6, Table 7 and Table 8.

A3. A binding agent that specifically binds to syndecan-1, or a portion thereof, wherein the binding agent comprises (i) a CDR-L1, CDR-L2 and a CDR-L3, each independently selected from a light chain variable domain selected from Table 4 or Table 5 and (ii) a CDR-H1, CDR-H2 and a CDR-H3, each independently selected from a heavy chain variable domain selected from Table 9 or Table 10.

A4. A binding agent that specifically binds to syndecan-1, or a portion thereof, wherein the binding agent comprises three CDRs of a light chain variable domain selected from the CDRs of Tables 1, 2 and 3, and three CDRs of a heavy chain variable domain selected from the CDRs of Tables 6, 7 and 8.

A5. A binding agent that specifically binds to syndecan-1, or a portion thereof, wherein the binding agent comprises a CDR-L1 selected from Table 1, a CDR-L2 selected from Table 2, a CDR-L3 selected from Table 3, a CDR-H1 selected from Table 6, a CDR-H2 selected from Table 7 and a CDR-H3 selected from Table 8.

A6. The binding agent of any one of embodiments A3 to A5, comprising: a CDR-L3 comprising the amino acid sequence of SEQ ID NO:27 or 28; a CDR-L2 comprising the amino acid sequence of SEQ ID NO:16, 17 or 18, a CDR-L1 comprising the amino acid sequence of SEQ ID NO:2 or 3; a CDR-H3 comprising the amino acid sequence of SEQ ID NO:68 or 69; a CDR-H2 comprising the amino acid sequence of SEQ ID NO:56 or 57; and a CDR-H1 comprising the amino acid sequence of SEQ ID NO:46 or 47.

A7. The binding agent of A6, comprising: a CDR-L3 comprising the amino acid sequence of SEQ ID NO:27; a CDR-L2 comprising the amino acid sequence of SEQ ID NO:16, a CDR-L1 comprising the amino acid sequence of SEQ ID NO:2; a CDR-H3 comprising the amino acid sequence of SEQ ID NO:69, a CDR-H2 comprising the amino acid sequence of SEQ ID NO:57; and a CDR-H1 comprising the amino acid sequence of SEQ ID NO:46.

A8. The binding agent of any one of embodiments A3 to A5, comprising: a CDR-L3 comprising the amino acid sequence of SEQ ID NO:29 or 30; a CDR-L2 comprising the amino acid sequence of SEQ ID NO:19, 20 or 21, a CDR-L1 comprising the amino acid sequence of SEQ ID NO:4 or 5; a CDR-H3 comprising the amino acid sequence of SEQ ID NO:70 or 71; a CDR-H2 comprising the amino acid sequence of SEQ ID NO:58, 59 or 60; and a CDR-H1 comprising the amino acid sequence of SEQ ID NO:48 or 49.

A9. The binding agent of any one of embodiments A3 to A5, comprising: a CDR-L3 comprising the amino acid sequence of SEQ ID NO:31; a CDR-L2 comprising the amino acid sequence of SEQ ID NO:22, a CDR-L1 comprising the amino acid sequence of SEQ ID NO:6 or 7; a CDR-H3 comprising the amino acid sequence of SEQ ID NO:72; a CDR-H2 comprising the amino acid sequence of SEQ ID NO:58, 59 or 60; and a CDR-H1 comprising the amino acid sequence of SEQ ID NO:50.

A10. The binding agent of any one of embodiments A3 to A5, comprising: a CDR-L3 comprising the amino acid sequence of SEQ ID NO:32; a CDR-L2 comprising the amino acid sequence of SEQ ID NO:23, a CDR-L1 comprising the amino acid sequence of SEQ ID NO:8 or 9; a CDR-H3 comprising the amino acid sequence of SEQ ID NO:73; a CDR-H2 comprising the amino acid sequence of SEQ ID NO:61 or 62; and a CDR-H1 comprising the amino acid sequence of SEQ ID NO:51.

A11. The binding agent of any one of embodiments A3 to A5, comprising: a CDR-L3 comprising the amino acid sequence of SEQ ID NO:29 or 30; a CDR-L2 comprising the amino acid sequence of SEQ ID NO:24, a CDR-L1 comprising the amino acid sequence of SEQ ID NO:10 or 11; a CDR-H3 comprising the amino acid sequence of SEQ ID NO:74; a CDR-H2 comprising the amino acid sequence of SEQ ID NO:58, 60 or 63; and a CDR-H1 comprising the amino acid sequence of SEQ ID NO:52.

A12. The binding agent of any one of embodiments A3 to A5, comprising: a CDR-L3 comprising the amino acid sequence of SEQ ID NO:33; a CDR-L2 comprising the amino acid sequence of SEQ ID NO:25, a CDR-L1 comprising the amino acid sequence of SEQ ID NO:12 or 13; a CDR-H3 comprising the amino acid sequence of SEQ ID NO:75; a CDR-H2 comprising the amino acid sequence of SEQ ID NO:64 or 65; and a CDR-H1 comprising the amino acid sequence of SEQ ID NO:53.

A13. The binding agent of any one of embodiments A3 to A5, comprising: a CDR-L3 comprising the amino acid sequence of SEQ ID NO:34; a CDR-L2 comprising the amino acid sequence of SEQ ID NO:26, a CDR-L1 comprising the amino acid sequence of SEQ ID NO:14 or 15; a CDR-H3 comprising the amino acid sequence of SEQ ID NO:76; a CDR-H2 comprising the amino acid sequence of SEQ ID NO:66 or 67; and a CDR-H1 comprising the amino acid sequence of SEQ ID NO:54 or 55.

A14. The binding agent of embodiment A6 or A7, comprising a heavy chain variable region comprising an amino acid sequence having at least 80% or at least 90% identity to an amino acid sequence selected from SEQ ID NOS: 84-88, and a light chain variable region comprising an amino acid sequence having at least 80% or at least 90% identity to an amino acid sequence selected from SEQ ID NOS: 42-45.

A15. The binding agent of embodiment A14, comprising a heavy chain variable region comprising an amino acid sequence selected from SEQ ID NOS: 84-88, and a light chain variable region comprising an amino acid sequence selected from SEQ ID NOS: 42-45.

A16. The binding agent of embodiment A14, comprising a heavy chain variable region comprising an amino acid sequence having at least 80% or at least 90% identity to an amino acid sequence of SEQ ID NO: 85 and a light chain variable region comprising an amino acid sequence having at least 80% or at least 90% identity to an amino acid sequence of SEQ ID NO: 42.

A17. The binding agent of embodiment A16, comprising a heavy chain variable region comprising an amino acid sequence of SEQ ID NO: 85 and a light chain variable region comprising an amino acid sequence of SEQ ID NO: 42.

A18. The binding agent of any one of embodiments A1 to A17, wherein the binding agent is a monoclonal antibody.

A19. The binding agent of any one of embodiments A1 to A18, wherein the binding agent comprises a constant region of an IgD, IgE, IgA or IgM.

A20. The binding agent of any one of embodiments A1 to A19, wherein the binding agent comprises a constant region of an $IgG_1$, $IgG_2$, $IgG_3$, or $IgG_4$.

A21. The binding agent of any one of embodiments A1 to A20, wherein the binding agent is humanized, chimeric or CDR grafted.

A22. The binding agent of any one of embodiments A1 to A21, wherein the binding agent is humanized.

A23. A pharmaceutical composition comprising:
a binding agent of any one of embodiments A1 to A22, and
a pharmaceutical acceptable excipient, diluent, additive or carrier.

The entirety of each patent, patent application, publication or any other reference or document cited herein hereby is incorporated by reference. In case of conflict, the specification, including definitions, will control.

Citation of any patent, patent application, publication or any other document is not an admission that any of the foregoing is pertinent prior art, nor does it constitute any admission as to the contents or date of these publications or documents.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described herein.

All of the features disclosed herein may be combined in any combination. Each feature disclosed in the specification may be replaced by an alternative feature serving a same, equivalent, or similar purpose. Thus, unless expressly stated otherwise, disclosed features (e.g., antibodies) are an example of a genus of equivalent or similar features.

As used herein, all numerical values or numerical ranges include integers within such ranges and fractions of the values or the integers within ranges unless the context clearly indicates otherwise. Further, when a listing of values is described herein (e.g., about 50%, 60%, 70%, 80%, 85% or 86%) the listing includes all intermediate and fractional values thereof (e.g., 54%, 85.4%). Thus, to illustrate, reference to 80% or more identity, includes 81%, 82%, 83%, 84%, 85%, 86%, 87%, 88%, 89%, 90%, 91%, 92%, 93%, 94% etc., as well as 81.1%, 81.2%, 81.3%, 81.4%, 81.5%, etc., 82.1%, 82.2%, 82.3%, 82.4%, 82.5%, etc., and so forth.

Reference to an integer with more (greater) or less than includes any number greater or less than the reference number, respectively. Thus, for example, a reference to less than 100, includes 99, 98, 97, etc. all the way down to the number one (1); and less than 10, includes 9, 8, 7, etc. all the way down to the number one (1).

As used herein, all numerical values or ranges include fractions of the values and integers within such ranges and fractions of the integers within such ranges unless the context clearly indicates otherwise. Thus, to illustrate, reference to a numerical range, such as 1-10 includes 1, 2, 3, 4, 5, 6, 7, 8, 9, 10, as well as 1.1, 1.2, 1.3, 1.4, 1.5, etc., and so forth. Reference to a range of 1-50 therefore includes 1, 2, 3, 4, 5, 6, 7, 8, 9, 10, 11, 12, 13, 14, 15, 16, 17, 18, 19, 20, etc., up to and including 50, as well as 1.1, 1.2, 1.3, 1.4, 1.5, etc., 2.1, 2.2, 2.3, 2.4, 2.5, etc., and so forth.

Reference to a series of ranges includes ranges which combine the values of the boundaries of different ranges within the series. Thus, to illustrate reference to a series of ranges, for example, of 1-10, 10-20, 20-30, 30-40, 40-50, 50-60, 60-75, 75-100, 100-150, 150-200, 200-250, 250-300, 300-400, 400-500, 500-750, 750-1,000, 1,000-1,500, 1,500-2,000, 2,000-2,500, 2,500-3,000, 3,000-3,500, 3,500-4,000, 4,000-4,500, 4,500-5,000, 5,500-6,000, 6,000-7,000, 7,000-8,000, or 8,000-9,000, includes ranges of 10-50, 50-100, 100-1,000, 1,000-3,000, 2,000-4,000, etc.

Modifications can be made to the foregoing without departing from the basic aspects of the technology. Although the technology has been described in substantial detail with reference to one or more specific embodiments, those of ordinary skill in the art will recognize that changes can be made to the embodiments specifically disclosed in this application, yet these modifications and improvements are within the scope and spirit of the technology.

The invention is generally disclosed herein using affirmative language to describe the numerous embodiments and aspects. The invention also specifically includes embodiments in which particular subject matter is excluded, in full or in part, such as substances or materials, method steps and conditions, protocols, or procedures. For example, in certain embodiments or aspects of the invention, materials and/or method steps are excluded. Thus, even though the invention is generally not expressed herein in terms of what the invention does not include aspects that are not expressly excluded in the invention are nevertheless disclosed herein.

The technology illustratively described herein suitably can be practiced in the absence of any element(s) not specifically disclosed herein. Thus, for example, in each instance herein any of the terms "comprising," "consisting essentially of," and "consisting of" can be replaced with either of the other two terms. The terms and expressions which have been employed are used as terms of description and not of limitation, and use of such terms and expressions do not exclude any equivalents of the features shown and described or segments thereof, and various modifications are possible within the scope of the technology claimed. The term "a" or "an" can refer to one of or a plurality of the elements it modifies (e.g., "a reagent" can mean one or more reagents) unless it is contextually clear either one of the elements or more than one of the elements is described. The term "about" as used herein refers to a value within 10% of the underlying parameter (i.e., plus or minus 10%), and use of the term "about" at the beginning of a string of values modifies each of the values (i.e., "about 1, 2 and 3" refers to about 1, about 2 and about 3). For example, a weight of "about 100 grams" can include weights between 90 grams and 110 grams. The term, "substantially" as used herein refers to a value modifier meaning "at least 95%", "at least 96%", "at least 97%", "at least 98%", or "at least 99%" and may include 100%. For example, a composition that is substantially free of X, may include less than 5%, less than 4%, less than 3%, less than 2%, or less than 1% of X, and/or X may be absent or undetectable in the composition.

Thus, it should be understood that although the present technology has been specifically disclosed by representative embodiments and optional features, modification and variation of the concepts herein disclosed can be resorted to by those skilled in the art, and such modifications and variations are considered within the scope of this technology.

The invention claimed is:

1. A syndecan-1 binding agent selected from the group consisting of:
   (i) a binding agent comprising
      a CDR-L1 of SEQ ID NOs: 2 or 3,
      a CDR-L2 of SEQ ID NOs: 16, 17 or 18,
      a CDR-L3 of SEQ ID NOs: 27 or 28,
      a CDR-H1 of SEQ ID NOs: 46 or 47,
      a CDR-H2 of SEQ ID NOs: 56 or 57, and
      a CDR-H3 of SEQ ID NOs: 68 or 69;
   (ii) a binding agent comprising
      a CDR-L1 of SEQ ID NOs: 4 or 5,
      a CDR-L2 of SEQ ID NOs: 19, 20 or 21,
      a CDR-L3 of SEQ ID NOs: 29 or 30,
      a CDR-H1 of SEQ ID NOs: 48 or 49,
      a CDR-H2 of SEQ ID NOs: 58, 59 or 60, and
      a CDR-H3 of SEQ ID NOs: 70 or 71;
   (iii) a binding agent comprising
      a CDR-L1 of SEQ ID NOs: 6 or 7,
      a CDR-L2 of SEQ ID NO: 22,
      a CDR-L3 of SEQ ID NO: 31,
      a CDR-H1 of SEQ ID NO: 50,
      a CDR-H2 of SEQ ID NOs: 58, 59, or 60, and
      a CDR-H3 of SEQ ID NO: 72;
   (iv) a binding agent comprising
      a CDR-L1 of SEQ ID NOs: 8 or 9,
      a CDR-L2 of SEQ ID NO: 23
      a CDR-L3 of SEQ ID NO: 32
      a CDR-H1 of SEQ ID NO: 51
      a CDR-H2 of SEQ ID NOs: 61 or 62, and
      a CDR-H3 of SEQ ID NO: 73;
   (v) a binding agent comprising
      a CDR-L1 of SEQ ID NOs: 10 or 11,
      a CDR-L2 of SEQ ID NO: 24,
      a CDR-L3 of SEQ ID NOs: 29 or 30,
      a CDR-H1 of SEQ ID NO: 52,
      a CDR-H2 of SEQ ID NOs: 58, 60 or 63, and
      a CDR-H3 of SEQ ID NO: 74;
   (vi) a binding agent comprising
      a CDR-L1 of SEQ ID NOs: 12 or 13,
      a CDR-L2 of SEQ ID NO: 25,
      a CDR-L3 of SEQ ID NO: 33,
      a CDR-H1 of SEQ ID NO: 53,
      a CDR-H2 of SEQ ID NOs: 64 or 65, and
      a CDR-H3 of SEQ ID NO: 75; and
   (vii) a binding agent comprising
      a CDR-L1 of SEQ ID NOs: 14 or 15,
      a CDR-L2 of SEQ ID NO: 26,
      a CDR-L3 of SEQ ID NO: 34,
      a CDR-H1 of SEQ ID NOs: 54 or 55,
      a CDR-H2 of SEQ ID NOs: 66 or 67, and
      a CDR-H3 of SEQ ID NO: 76;
   wherein the syndecan-1 binding agent specifically binds to syndecan-1, or a portion thereof.

2. The syndecan-1 binding agent of claim 1, which comprises
   a CDR-L1 of SEQ ID NOs: 2 or 3,
   a CDR-L2 of SEQ ID NOs: 16, 17 or 18,
   a CDR-L3 of SEQ ID NOs: 27 or 28,
   a CDR-H1 of SEQ ID NOs: 46 or 47,
   a CDR-H2 of SEQ ID NOs: 56 or 57, and
   a CDR-H3 of SEQ ID NOs: 68 or 69.

3. The syndecan-1 binding agent of claim 2, comprising the CDR-L1 of SEQ ID NO:2, the CDR-L2 of SEQ ID NO:16, the CDR-L3 of SEQ ID NO:27, the CDR-H1 of SEQ ID NO:46, the CDR-H2 of SEQ ID NO:56, and the CDR-H3 of SEQ ID NO:68.

4. The syndecan-1 binding agent of claim 1, which comprises
   a CDR-L1 of SEQ ID NOs: 4 or 5,
   a CDR-L2 of SEQ ID NOs: 19, 20 or 21,
   a CDR-L3 of SEQ ID NOs: 29 or 30,
   a CDR-H1 of SEQ ID NOs: 48 or 49,
   a CDR-H2 of SEQ ID NOs: 58, 59 or 60, and
   a CDR-H3 of SEQ ID NOs: 70 or 71.

5. The syndecan-1 binding agent of claim 1, which comprises
   a CDR-L1 of SEQ ID NOs: 6 or 7,
   a CDR-L2 of SEQ ID NO: 22,
   a CDR-L3 of SEQ ID NO: 31,
   a CDR-H1 of SEQ ID NO: 50,
   a CDR-H2 of SEQ ID NOs: 58, 59, or 60, and
   a CDR-H3 of SEQ ID NO: 72.

6. The syndecan-1 binding agent of claim 1, which comprises
   a CDR-L1 of SEQ ID NOs: 8 or 9,
   a CDR-L2 of SEQ ID NO: 23
   a CDR-L3 of SEQ ID NO: 32
   a CDR-H1 of SEQ ID NO: 51
   a CDR-H2 of SEQ ID NOs: 61 or 62, and a CDR-H3 of SEQ ID NO: 73.

7. The syndecan-1 binding agent of claim 1, which comprises
a CDR-L1 of SEQ ID NOs: 10 or 11,
a CDR-L2 of SEQ ID NO: 24,
a CDR-L3 of SEQ ID NOs: 29 or 30,
a CDR-H1 of SEQ ID NO: 52,
a CDR-H2 of SEQ ID NOs: 58, 60 or 63, and
a CDR-H3 of SEQ ID NO: 74.

8. The syndecan-1 binding agent of claim 1, which comprises
a CDR-L1 of SEQ ID NOs: 12 or 13,
a CDR-L2 of SEQ ID NO: 25,
a CDR-L3 of SEQ ID NO: 33,
a CDR-H1 of SEQ ID NO: 53,
a CDR-H2 of SEQ ID NOs: 64 or 65, and
a CDR-H3 of SEQ ID NO: 75.

9. The syndecan-1 binding agent of claim 1, which comprises
a CDR-L1 of SEQ ID NOs: 14 or 15,
a CDR-L2 of SEQ ID NO: 26,
a CDR-L3 of SEQ ID NO: 34,
a CDR-H1 of SEQ ID NOs: 54 or 55,
a CDR-H2 of SEQ ID NOs: 66 or 67, and
a CDR-H3 of SEQ ID NO: 76.

10. The syndecan-1 binding agent of claim 1, wherein the syndecan-1 binding agent comprises a light chain variable region having an amino acid sequence having at least 80%, or at least 90% identity to an amino acid sequence of a light chain variable region selected from SEQ ID NOs:42-44, and wherein the syndecan-1 binding agent comprises a heavy chain variable region having an amino acid sequence having at least 80%, or at least 90% identity to an amino acid sequence of a heavy chain variable region selected from or SEQ ID NOs:84-87.

11. The syndecan-1 binding agent of claim 10, wherein the binding agent comprises the light chain variable region selected from SEQ ID NOs:42-44, and the heavy chain variable region selected from SEQ ID NOs:84-87.

12. The syndecan-1 binding agent of claim 1, wherein the syndecan-1 binding agent comprises a light chain variable region having an amino acid sequence having at least 80%, or at least 90% identity to an amino acid sequence of SEQ ID NO:42, and wherein the syndecan-1 binding agent comprises a heavy chain variable region having an amino acid sequence having at least 80%, or at least 90% identity to an amino acid sequence of SEQ ID NO:85.

13. The syndecan-1 binding agent of claim 12, wherein the binding agent comprises a light chain variable region of SEQ ID NO:42, and a heavy chain variable region of SEQ ID NO:85.

14. The syndecan-1 binding agent of claim 1, wherein the syndecan-1 binding agent is an antibody, or a binding fragment thereof.

15. The syndecan-1 binding agent of claim 1, wherein the syndecan-1 binding agent is humanized.

16. The syndecan-1 binding agent of claim 1, wherein the syndecan-1 binding agent specifically binds to a human syndecan-1.

17. The syndecan-1 binding agent of claim 1, wherein the syndecan-1 binding agent specifically binds to an extracellular domain of syndecan-1.

18. The syndecan-1 binding agent of claim 1, wherein the syndecan-1 binding agent specifically binds to a polypeptide comprising the amino acid sequence of $GX_1KEX_2EAX_3VLP$ (SEQ ID NO:91), wherein $X_1$, $X_2$ and $X_3$ are selected from any amino acid.

19. The syndecan-1 binding agent of claim 18, wherein the syndecan-1 binding agent specifically binds to a polypeptide comprising, or consisting of the amino acid sequence of AGEGPKEGEAVVLP (SEQ ID NO:89) or GPKEGEAVVLP (SEQ ID NO:90).

20. A pharmaceutical composition comprising the syndecan-1 binding agent of claim 1 and a pharmaceutically acceptable additive and/or carrier.

21. A method of treating a subject having or suspected of having a neoplastic disorder or cancer comprising administering to a subject in need thereof a therapeutic amount of the binding agent of claim 1, wherein the neoplastic disorder or cancer comprises a cell that expresses syndecan-1.

22. The method of claim 21, wherein the neoplastic disorder or cancer is selected from a lung carcinoma, breast carcinoma, ovarian carcinoma, kidney carcinoma, colorectal carcinoma, gastric carcinoma, thyroid carcinoma, pancreas carcinoma, neuroblastoma, a squamous cell carcinoma of the head and neck, cervical cancer, hepatocellular cancer, sarcomas, mesothelioma, glioblastoma, multiple myeloma, melanoma, prostate carcinoma and esophageal carcinoma.

23. A syndecan-1 binding agent, wherein the syndecan-1 binding agent is an antibody, or a binding fragment thereof and wherein the binding agent comprises a light chain variable region of SEQ ID NO:45, and a heavy chain variable region of SEQ ID NO:88.

* * * * *

SEQUENCE LISTING

<160> NUMBER OF SEQ ID NOS: 103

<210> SEQ ID NO 1
<211> LENGTH: 310
<212> TYPE: PRT
<213> ORGANISM: Homo sapiens

<400> SEQUENCE: 1

Met Arg Arg Ala Ala Leu Trp Leu Trp Leu Cys Ala Leu Ala Leu Ser
1               5                   10                  15

Leu Gln Pro Ala Leu Pro Gln Ile Val Ala Thr Asn Leu Pro Pro Glu
            20                  25                  30

Asp Gln Asp Gly Ser Gly Asp Ser Asp Asn Phe Ser Gly Ser Gly
        35                  40                  45

Ala Gly Ala Leu Gln Asp Ile Thr Leu Ser Gln Gln Thr Pro Ser Thr
    50                  55                  60

Trp Lys Asp Thr Gln Leu Leu Thr Ala Ile Pro Thr Ser Pro Glu Pro
65                  70                  75                  80

Thr Gly Leu Glu Ala Thr Ala Ala Ser Thr Ser Thr Leu Pro Ala Gly
                85                  90                  95

Glu Gly Pro Lys Glu Gly Glu Ala Val Val Leu Pro Glu Val Glu Pro
            100                 105                 110

Gly Leu Thr Ala Arg Glu Gln Glu Ala Thr Pro Arg Pro Arg Glu Thr
        115                 120                 125

Thr Gln Leu Pro Thr Thr His Leu Ala Ser Thr Thr Thr Ala Thr Thr
    130                 135                 140

Ala Gln Glu Pro Ala Thr Ser His Pro His Arg Asp Met Gln Pro Gly
145                 150                 155                 160

His His Glu Thr Ser Thr Pro Ala Gly Pro Ser Gln Ala Asp Leu His
                165                 170                 175

Thr Pro His Thr Glu Asp Gly Gly Pro Ser Ala Thr Glu Arg Ala Ala
            180                 185                 190

Glu Asp Gly Ala Ser Ser Gln Leu Pro Ala Ala Glu Gly Ser Gly Glu
        195                 200                 205

Gln Asp Phe Thr Phe Glu Thr Ser Gly Glu Asn Thr Ala Val Val Ala
    210                 215                 220

Val Glu Pro Asp Arg Arg Asn Gln Ser Pro Val Asp Gln Gly Ala Thr
225                 230                 235                 240

Gly Ala Ser Gln Gly Leu Leu Asp Arg Lys Glu Val Leu Gly Gly Val
                245                 250                 255

Ile Ala Gly Gly Leu Val Gly Leu Ile Phe Ala Val Cys Leu Val Gly
            260                 265                 270

Phe Met Leu Tyr Arg Met Lys Lys Lys Asp Glu Gly Ser Tyr Ser Leu
        275                 280                 285

Glu Glu Pro Lys Gln Ala Asn Gly Gly Ala Tyr Gln Lys Pro Thr Lys
    290                 295                 300

Gln Glu Glu Phe Tyr Ala
305                 310

<210> SEQ ID NO 2
<211> LENGTH: 16
<212> TYPE: PRT
<213> ORGANISM: Mus musculus

<400> SEQUENCE: 2

Lys Ser Ser Gln Ser Leu Leu Ala Ser Asp Gly Lys Thr Tyr Leu Asn

```
                  1               5              10              15
```

<210> SEQ ID NO 3
<211> LENGTH: 11
<212> TYPE: PRT
<213> ORGANISM: Mus musculus

<400> SEQUENCE: 3

```
Gln Ser Leu Leu Ala Ser Asp Gly Lys Thr Tyr
1               5                  10
```

<210> SEQ ID NO 4
<211> LENGTH: 11
<212> TYPE: PRT
<213> ORGANISM: Mus musculus

<400> SEQUENCE: 4

```
Lys Ala Ser Glu Asn Val Gly Asn Tyr Val Ser
1               5                  10
```

<210> SEQ ID NO 5
<211> LENGTH: 6
<212> TYPE: PRT
<213> ORGANISM: Mus musculus

<400> SEQUENCE: 5

```
Glu Asn Val Gly Asn Tyr
1               5
```

<210> SEQ ID NO 6
<211> LENGTH: 11
<212> TYPE: PRT
<213> ORGANISM: Mus musculus

<400> SEQUENCE: 6

```
Lys Ala Ser Glu Asn Val Gly Thr Tyr Val Ser
1               5                  10
```

<210> SEQ ID NO 7
<211> LENGTH: 8
<212> TYPE: PRT
<213> ORGANISM: Mus musculus

<400> SEQUENCE: 7

```
Ala Ser Glu Asn Val Gly Thr Tyr
1               5
```

<210> SEQ ID NO 8
<211> LENGTH: 10
<212> TYPE: PRT
<213> ORGANISM: Mus musculus

<400> SEQUENCE: 8

```
Arg Ala Ser Ser Ser Val Asn Tyr Met His
1               5                  10
```

<210> SEQ ID NO 9
<211> LENGTH: 7
<212> TYPE: PRT
<213> ORGANISM: Mus musculus

<400> SEQUENCE: 9

```
Ala Ser Ser Ser Val Asn Tyr
1               5
```

```
<210> SEQ ID NO 10
<211> LENGTH: 11
<212> TYPE: PRT
<213> ORGANISM: Mus musculus

<400> SEQUENCE: 10

Lys Ala Ser Glu Asn Val Gly Ser Tyr Val Ser
1               5                   10

<210> SEQ ID NO 11
<211> LENGTH: 8
<212> TYPE: PRT
<213> ORGANISM: Mus musculus

<400> SEQUENCE: 11

Ala Ser Glu Asn Val Gly Ser Tyr
1               5

<210> SEQ ID NO 12
<211> LENGTH: 16
<212> TYPE: PRT
<213> ORGANISM: Mus musculus

<400> SEQUENCE: 12

Lys Ser Gly Gln Ser Leu Leu Tyr Ser Asn Gly Lys Thr Tyr Leu Thr
1               5                   10                  15

<210> SEQ ID NO 13
<211> LENGTH: 11
<212> TYPE: PRT
<213> ORGANISM: Mus musculus

<400> SEQUENCE: 13

Lys Ser Gly Gln Ser Leu Leu Tyr Ser Asn Gly
1               5                   10

<210> SEQ ID NO 14
<211> LENGTH: 16
<212> TYPE: PRT
<213> ORGANISM: Mus musculus

<400> SEQUENCE: 14

Lys Ser Ser Gln Ser Leu Leu Tyr Ser Asn Gly Lys Thr Tyr Leu Asn
1               5                   10                  15

<210> SEQ ID NO 15
<211> LENGTH: 11
<212> TYPE: PRT
<213> ORGANISM: Mus musculus

<400> SEQUENCE: 15

Lys Ser Ser Gln Ser Leu Leu Tyr Ser Asn Gly
1               5                   10

<210> SEQ ID NO 16
<211> LENGTH: 8
<212> TYPE: PRT
<213> ORGANISM: Mus musculus

<400> SEQUENCE: 16

Tyr Leu Val Ser Lys Leu Asp Ser
1               5

<210> SEQ ID NO 17
```

```
<211> LENGTH: 7
<212> TYPE: PRT
<213> ORGANISM: Mus musculus

<400> SEQUENCE: 17

Leu Val Ser Lys Leu Asp Ser
1               5

<210> SEQ ID NO 18
<211> LENGTH: 6
<212> TYPE: PRT
<213> ORGANISM: Mus musculus

<400> SEQUENCE: 18

Leu Val Ser Lys Leu Asp
1               5

<210> SEQ ID NO 19
<211> LENGTH: 8
<212> TYPE: PRT
<213> ORGANISM: Mus musculus

<400> SEQUENCE: 19

Tyr Gly Ala Ser Tyr Arg Tyr Thr
1               5

<210> SEQ ID NO 20
<211> LENGTH: 7
<212> TYPE: PRT
<213> ORGANISM: Mus musculus

<400> SEQUENCE: 20

Gly Ala Ser Tyr Arg Tyr Thr
1               5

<210> SEQ ID NO 21
<211> LENGTH: 6
<212> TYPE: PRT
<213> ORGANISM: Mus musculus

<400> SEQUENCE: 21

Gly Ala Ser Tyr Arg Tyr
1               5

<210> SEQ ID NO 22
<211> LENGTH: 7
<212> TYPE: PRT
<213> ORGANISM: Mus musculus

<400> SEQUENCE: 22

Gly Ala Ser Asn Arg Tyr Thr
1               5

<210> SEQ ID NO 23
<211> LENGTH: 7
<212> TYPE: PRT
<213> ORGANISM: Mus musculus

<400> SEQUENCE: 23

Ala Thr Ser Tyr Leu Ala Ser
1               5

<210> SEQ ID NO 24
<211> LENGTH: 7
<212> TYPE: PRT
```

```
<213> ORGANISM: Mus musculus

<400> SEQUENCE: 24

Gly Ala Ser Asn Arg Asn Thr
1               5

<210> SEQ ID NO 25
<211> LENGTH: 7
<212> TYPE: PRT
<213> ORGANISM: Mus musculus

<400> SEQUENCE: 25

Gln Val Ser Lys Leu Asp Pro
1               5

<210> SEQ ID NO 26
<211> LENGTH: 7
<212> TYPE: PRT
<213> ORGANISM: Mus musculus

<400> SEQUENCE: 26

Leu Val Ser Lys Val Asp Ser
1               5

<210> SEQ ID NO 27
<211> LENGTH: 9
<212> TYPE: PRT
<213> ORGANISM: Mus musculus

<400> SEQUENCE: 27

Trp Gln Gly Ala His Phe Pro Phe Thr
1               5

<210> SEQ ID NO 28
<211> LENGTH: 7
<212> TYPE: PRT
<213> ORGANISM: Mus musculus

<400> SEQUENCE: 28

Gln Gly Ala His Phe Pro Phe
1               5

<210> SEQ ID NO 29
<211> LENGTH: 9
<212> TYPE: PRT
<213> ORGANISM: Mus musculus

<400> SEQUENCE: 29

Gly Gln Ser Ser Arg Tyr Pro Leu Thr
1               5

<210> SEQ ID NO 30
<211> LENGTH: 7
<212> TYPE: PRT
<213> ORGANISM: Mus musculus

<400> SEQUENCE: 30

Gln Ser Ser Arg Tyr Pro Leu
1               5

<210> SEQ ID NO 31
<211> LENGTH: 9
<212> TYPE: PRT
<213> ORGANISM: Mus musculus
```

```
<400> SEQUENCE: 31

Gly Gln Ser Ser Arg Tyr Pro Leu Thr
1               5

<210> SEQ ID NO 32
<211> LENGTH: 9
<212> TYPE: PRT
<213> ORGANISM: Mus musculus

<400> SEQUENCE: 32

Gln Gln Trp Ser Ser Asp Pro Leu Thr
1               5

<210> SEQ ID NO 33
<211> LENGTH: 9
<212> TYPE: PRT
<213> ORGANISM: Mus musculus

<400> SEQUENCE: 33

Leu Gln Asn Thr Tyr Tyr Pro His Thr
1               5

<210> SEQ ID NO 34
<211> LENGTH: 9
<212> TYPE: PRT
<213> ORGANISM: Mus musculus

<400> SEQUENCE: 34

Val Gln Gly Thr His Phe Pro Leu Thr
1               5

<210> SEQ ID NO 35
<211> LENGTH: 113
<212> TYPE: PRT
<213> ORGANISM: Mus musculus

<400> SEQUENCE: 35

Asp Val Val Met Thr Gln Thr Pro Leu Thr Leu Ser Val Thr Ile Gly
1               5                  10                  15

Gln Pro Ala Ser Ile Ser Cys Lys Ser Gln Ser Leu Leu Ala Ser
            20                  25                  30

Asp Gly Lys Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Gly Phe Thr Leu Gln Ile
65                  70                  75                  80

Ser Arg Val Glu Ala Glu Asp Leu Gly Ile Tyr Tyr Cys Trp Gln Gly
                85                  90                  95

Ala His Phe Pro Phe Thr Phe Gly Ser Gly Thr Lys Leu Glu Ile Lys
            100                 105                 110

Arg

<210> SEQ ID NO 36
<211> LENGTH: 108
<212> TYPE: PRT
<213> ORGANISM: Mus musculus

<400> SEQUENCE: 36

Asn Ile Ile Met Thr Gln Ser Pro Lys Ser Met Ala Met Ser Val Gly
1               5                   10                  15
```

```
Glu Arg Val Thr Leu Ser Cys Lys Ala Ser Glu Asn Val Gly Asn Tyr
             20                  25                  30

Val Ser Trp Tyr Gln Gln Lys Pro Glu Gln Ser Pro Lys Leu Leu Ile
         35                  40                  45

Tyr Gly Ala Ser Tyr Arg Tyr Thr Gly Val Pro Asp Arg Phe Thr Gly
     50                  55                  60

Ser Gly Ser Gly Thr Asp Phe Thr Leu Thr Ile Ser Ser Val Gln Ala
65                  70                  75                  80

Glu Asp Leu Ala Asp Tyr His Cys Gly Gln Ser Ser Arg Tyr Pro Leu
                 85                  90                  95

Thr Phe Gly Ala Gly Thr Lys Leu Glu Leu Lys Arg
            100                 105
```

<210> SEQ ID NO 37
<211> LENGTH: 108
<212> TYPE: PRT
<213> ORGANISM: Mus musculus

<400> SEQUENCE: 37

```
Asn Ile Val Met Thr Gln Ser Pro Lys Ser Met Ser Met Ser Val Gly
1               5                   10                  15

Glu Arg Val Thr Leu Ser Cys Lys Ala Ser Glu Asn Val Gly Thr Tyr
             20                  25                  30

Val Ser Trp Tyr Gln Gln Lys Ser Asp Gln Ser Pro Lys Leu Leu Ile
         35                  40                  45

Tyr Gly Ala Ser Asn Arg Tyr Thr Gly Val Pro Asp Arg Phe Thr Gly
     50                  55                  60

Ser Gly Ser Ala Thr Asp Phe Thr Leu Thr Ile Thr Ser Val Gln Ser
65                  70                  75                  80

Glu Asp Leu Ala Asp Tyr His Cys Gly Gln Ser Ser Arg Tyr Pro Leu
                 85                  90                  95

Thr Phe Gly Ala Gly Thr Lys Leu Glu Leu Lys Arg
            100                 105
```

<210> SEQ ID NO 38
<211> LENGTH: 107
<212> TYPE: PRT
<213> ORGANISM: Mus musculus

<400> SEQUENCE: 38

```
Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Asn Tyr Met
             20                  25                  30

His Trp Tyr Gln Gln Lys Pro Gly Ser Ser Pro Lys His Trp Ile Tyr
         35                  40                  45

Ala Thr Ser Tyr Leu Ala Ser Gly Val Pro Ala Arg Phe Ser Gly Ser
     50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Ser Ser Asp Pro Leu Thr
                 85                  90                  95

Phe Gly Ala Gly Thr Lys Leu Glu Leu Lys Arg
            100                 105
```

<210> SEQ ID NO 39

```
<211> LENGTH: 108
<212> TYPE: PRT
<213> ORGANISM: Mus musculus

<400> SEQUENCE: 39

Asn Ile Val Met Thr Gln Ser Pro Lys Ser Met Ser Met Ser Val Gly
1               5                   10                  15

Gln Arg Val Thr Leu Ser Cys Lys Ala Ser Glu Asn Val Gly Ser Tyr
            20                  25                  30

Val Ser Trp Tyr Gln Gln Lys Pro Glu Gln Ser Pro Lys Leu Leu Ile
        35                  40                  45

Tyr Gly Ala Ser Asn Arg Asn Thr Gly Val Pro Asp Arg Phe Thr Gly
    50                  55                  60

Ser Gly Ser Ala Thr Asp Phe Thr Leu Thr Ile Ser Ser Val Gln Ala
65                  70                  75                  80

Glu Asp Leu Ala Asp Tyr His Cys Gly Gln Ser Ser Arg Tyr Pro Leu
                85                  90                  95

Thr Phe Gly Gly Gly Thr Lys Leu Glu Leu Lys Arg
            100                 105

<210> SEQ ID NO 40
<211> LENGTH: 113
<212> TYPE: PRT
<213> ORGANISM: Mus musculus

<400> SEQUENCE: 40

Asp Val Val Met Thr Gln Thr Pro Leu Ser Leu Ser Val Thr Ile Gly
1               5                   10                  15

Gln Pro Ala Ser Ile Ser Cys Lys Ser Gly Gln Ser Leu Leu Tyr Ser
            20                  25                  30

Asn Gly Lys Thr Tyr Leu Thr Trp Leu Gln Gln Arg Pro Gly Gln Ala
        35                  40                  45

Pro Lys Leu Leu Met Tyr Gln Val Ser Lys Leu Asp Pro Gly Ile Pro
    50                  55                  60

Asp Arg Phe Ser Gly Ser Gly Ser Glu Thr Asp Phe Thr Leu Lys Ile
65                  70                  75                  80

Ser Arg Val Glu Ala Glu Asp Leu Gly Val Tyr Tyr Cys Leu Gln Asn
                85                  90                  95

Thr Tyr Tyr Pro His Thr Phe Gly Ala Gly Thr Lys Leu Glu Leu Lys
            100                 105                 110

Arg

<210> SEQ ID NO 41
<211> LENGTH: 113
<212> TYPE: PRT
<213> ORGANISM: Mus musculus

<400> SEQUENCE: 41

Asp Val Val Met Thr Gln Thr Pro Leu Thr Leu Ser Val Thr Ile Gly
1               5                   10                  15

Gln Ser Ala Ser Ile Ser Cys Lys Ser Ser Gln Ser Leu Leu Tyr Ser
            20                  25                  30

Asn Gly Lys Thr Tyr Leu Asn Trp Leu Leu Gln Arg Pro Gly Gln Ser
        35                  40                  45

Pro Lys Arg Leu Ile Tyr Leu Val Ser Lys Val Asp Ser Gly Val Pro
    50                  55                  60

Asp Arg Phe Thr Gly Ser Gly Ser Gly Thr Asp Phe Thr Leu Ser Ile
```

```
                65                  70                  75                  80
Ser Arg Val Glu Ala Glu Asp Leu Gly Val Tyr Tyr Cys Val Gln Gly
                    85                  90                  95

Thr His Phe Pro Leu Thr Phe Gly Val Gly Thr Lys Leu Glu Leu Lys
                100                 105                 110

Arg

<210> SEQ ID NO 42
<211> LENGTH: 113
<212> TYPE: PRT
<213> ORGANISM: Artificial Sequence
<220> FEATURE:
<223> OTHER INFORMATION: Light Chains Variable Region

<400> SEQUENCE: 42

Asp Val Val Met Thr Gln Thr Pro Leu Ser Leu Ser Val Thr Pro Gly
1               5                   10                  15

Gln Pro Ala Ser Ile Ser Cys Lys Ser Gln Ser Leu Leu Ala Ser
            20                  25                  30

Asp Gly Lys Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asn Arg Phe Ser Gly Ser Gly Ser Gly Thr Asp Phe Thr Leu Gln Ile
65                  70                  75                  80

Ser Arg Val Glu Ala Glu Asp Val Gly Leu Tyr Tyr Cys Trp Gln Gly
                    85                  90                  95

Ala His Phe Pro Phe Thr Phe Gly Ser Gly Thr Lys Leu Glu Ile Lys
                100                 105                 110

Arg

<210> SEQ ID NO 43
<211> LENGTH: 113
<212> TYPE: PRT
<213> ORGANISM: Artificial Sequence
<220> FEATURE:
<223> OTHER INFORMATION: Light Chains Variable Region

<400> SEQUENCE: 43

Asp Val Val Met Thr Gln Thr Pro Leu Ser Leu Ser Val Thr Pro Gly
1               5                   10                  15

Gln Pro Ala Ser Ile Ser Cys Lys Ser Gln Ser Leu Leu Ala Ser
            20                  25                  30

Asp Gly Lys Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asn Arg Phe Ser Gly Ser Gly Ser Gly Thr Asp Phe Thr Leu Gln Ile
65                  70                  75                  80

Ser Arg Val Glu Ala Glu Asp Val Gly Leu Tyr Tyr Cys Met Gln Gly
                    85                  90                  95

Ala His Phe Pro Phe Thr Phe Gly Gly Gly Thr Lys Val Glu Ile Lys
                100                 105                 110

Arg

<210> SEQ ID NO 44
<211> LENGTH: 113
```

<212> TYPE: PRT
<213> ORGANISM: Artificial Sequence
<220> FEATURE:
<223> OTHER INFORMATION: Light Chains Variable Region

<400> SEQUENCE: 44

```
Asp Val Val Met Thr Gln Ser Pro Leu Ser Leu Ser Val Thr Leu Gly
1               5                   10                  15

Gln Pro Ala Ser Ile Ser Cys Lys Ser Ser Gln Ser Leu Leu Ala Ser
            20                  25                  30

Asp Gly Lys Thr Tyr Leu Asn Trp Leu Gln Gln Arg Pro Gly Gln Ser
        35                  40                  45

Pro Arg Arg Leu Ile Tyr Leu Val Ser Lys Leu Asp Ser Gly Val Pro
    50                  55                  60

Asn Arg Phe Ser Gly Ser Gly Ser Gly Thr Asp Phe Thr Leu Gln Ile
65                  70                  75                  80

Ser Arg Val Glu Ala Glu Asp Val Gly Leu Tyr Tyr Cys Trp Gln Gly
                85                  90                  95

Ala His Phe Pro Phe Thr Phe Gly Ser Gly Thr Lys Leu Glu Ile Lys
            100                 105                 110

Arg
```

<210> SEQ ID NO 45
<211> LENGTH: 219
<212> TYPE: PRT
<213> ORGANISM: Artificial Sequence
<220> FEATURE:
<223> OTHER INFORMATION: Light Chains Variable Region

<400> SEQUENCE: 45

```
Asp Val Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu Ala Ser
            20                  25                  30

Asp Gly Lys Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asn Arg Phe Ser Gly Ser Gly Ser Gly Thr Asp Phe Thr Leu Gln Ile
65                  70                  75                  80

Ser Arg Val Glu Ala Glu Asp Val Gly Leu Tyr Tyr Cys Trp Gln Gly
                85                  90                  95

Ala His Phe Pro Phe Thr Phe Gly Ser Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205
```

```
Pro Val Thr Lys Ser Phe Asn Arg Gly Glu Cys
    210                 215
```

<210> SEQ ID NO 46
<211> LENGTH: 13
<212> TYPE: PRT
<213> ORGANISM: Mus musculus

<400> SEQUENCE: 46

```
Lys Ala Ser Gly Tyr Thr Phe Thr Ser Tyr Tyr Leu Tyr
1               5                   10
```

<210> SEQ ID NO 47
<211> LENGTH: 10
<212> TYPE: PRT
<213> ORGANISM: Mus musculus

<400> SEQUENCE: 47

```
Gly Tyr Thr Phe Thr Ser Tyr Tyr Leu Tyr
1               5                   10
```

<210> SEQ ID NO 48
<211> LENGTH: 13
<212> TYPE: PRT
<213> ORGANISM: Mus musculus

<400> SEQUENCE: 48

```
Ala Ala Ser Gly Phe Thr Phe Asn Thr Tyr Ala Met Asn
1               5                   10
```

<210> SEQ ID NO 49
<211> LENGTH: 11
<212> TYPE: PRT
<213> ORGANISM: Mus musculus

<400> SEQUENCE: 49

```
Ala Ser Gly Phe Thr Phe Asn Thr Tyr Ala Met
1               5                   10
```

<210> SEQ ID NO 50
<211> LENGTH: 10
<212> TYPE: PRT
<213> ORGANISM: Mus musculus

<400> SEQUENCE: 50

```
Gly Phe Ala Phe Asn Thr Tyr Ala Met Asn
1               5                   10
```

<210> SEQ ID NO 51
<211> LENGTH: 10
<212> TYPE: PRT
<213> ORGANISM: Mus musculus

<400> SEQUENCE: 51

```
Gly Tyr Thr Phe Ser Ser His Trp Met Gln
1               5                   10
```

<210> SEQ ID NO 52
<211> LENGTH: 10
<212> TYPE: PRT
<213> ORGANISM: Mus musculus

<400> SEQUENCE: 52

```
Gly Phe Thr Phe Asn Thr Tyr Ala Met Asn
1               5                   10
```

<210> SEQ ID NO 53
<211> LENGTH: 13
<212> TYPE: PRT
<213> ORGANISM: Mus musculus

<400> SEQUENCE: 53

Lys Ala Ser Gly Tyr Thr Phe Thr Asn Tyr Tyr Met Tyr
1               5                   10

<210> SEQ ID NO 54
<211> LENGTH: 5
<212> TYPE: PRT
<213> ORGANISM: Mus musculus

<400> SEQUENCE: 54

Tyr Thr Phe Ala Asp
1               5

<210> SEQ ID NO 55
<211> LENGTH: 9
<212> TYPE: PRT
<213> ORGANISM: Mus musculus

<400> SEQUENCE: 55

Tyr Thr Phe Ala Asp Tyr Tyr Met Lys
1               5

<210> SEQ ID NO 56
<211> LENGTH: 10
<212> TYPE: PRT
<213> ORGANISM: Mus musculus

<400> SEQUENCE: 56

Glu Ile Tyr Pro Arg Ser Gly Gly Thr Asn
1               5                   10

<210> SEQ ID NO 57
<211> LENGTH: 17
<212> TYPE: PRT
<213> ORGANISM: Mus musculus

<400> SEQUENCE: 57

Glu Ile Tyr Pro Arg Ser Gly Gly Thr Asn Ile Asn Glu Lys Phe Leu
1               5                   10                  15

Ser

<210> SEQ ID NO 58
<211> LENGTH: 12
<212> TYPE: PRT
<213> ORGANISM: Mus musculus

<400> SEQUENCE: 58

Arg Ile Arg Ser Lys Ser Asn Asn Tyr Ala Thr Tyr
1               5                   10

<210> SEQ ID NO 59
<211> LENGTH: 19
<212> TYPE: PRT
<213> ORGANISM: Mus musculus

<400> SEQUENCE: 59

Arg Ile Arg Ser Lys Ser Asn Asn Tyr Ala Thr Tyr Tyr Ala Asp Ser
1               5                   10                  15

Val Lys Asp

<210> SEQ ID NO 60
<211> LENGTH: 11
<212> TYPE: PRT
<213> ORGANISM: Mus musculus

<400> SEQUENCE: 60

Ile Arg Ser Lys Ser Asn Asn Tyr Ala Thr Tyr
1               5                   10

<210> SEQ ID NO 61
<211> LENGTH: 17
<212> TYPE: PRT
<213> ORGANISM: Mus musculus

<400> SEQUENCE: 61

Ala Ile Tyr Pro Gly Asp Gly Asp Thr Arg Phe Thr Gln Lys Phe Lys
1               5                   10                  15
Gly

<210> SEQ ID NO 62
<211> LENGTH: 12
<212> TYPE: PRT
<213> ORGANISM: Mus musculus

<400> SEQUENCE: 62

Tyr Pro Gly Asp Gly Asp Thr Arg Phe Thr Gln Lys
1               5                   10

<210> SEQ ID NO 63
<211> LENGTH: 19
<212> TYPE: PRT
<213> ORGANISM: Mus musculus

<400> SEQUENCE: 63

Arg Ile Arg Ser Lys Ser Asn Asn Tyr Ala Thr Tyr Tyr Val Asp Ser
1               5                   10                  15
Val Lys Asp

<210> SEQ ID NO 64
<211> LENGTH: 17
<212> TYPE: PRT
<213> ORGANISM: Mus musculus

<400> SEQUENCE: 64

Glu Ile Asn Pro Gly Asn Gly Gly Thr Asn Phe Asn Glu Lys Phe Lys
1               5                   10                  15
Asn

<210> SEQ ID NO 65
<211> LENGTH: 13
<212> TYPE: PRT
<213> ORGANISM: Mus musculus

<400> SEQUENCE: 65

Asn Pro Gly Asn Gly Gly Thr Asn Phe Asn Glu Lys Phe
1               5                   10

<210> SEQ ID NO 66
<211> LENGTH: 10
<212> TYPE: PRT

```
<213> ORGANISM: Mus musculus

<400> SEQUENCE: 66

Asp Ile Asn Pro Asn Ser Gly Asp Thr Phe
1               5                   10

<210> SEQ ID NO 67
<211> LENGTH: 17
<212> TYPE: PRT
<213> ORGANISM: Mus musculus

<400> SEQUENCE: 67

Asp Ile Asn Pro Asn Ser Gly Asp Thr Phe Tyr Asn His Lys Phe Lys
1               5                   10                  15

Gly

<210> SEQ ID NO 68
<211> LENGTH: 6
<212> TYPE: PRT
<213> ORGANISM: Mus musculus

<400> SEQUENCE: 68

Thr Arg Ser Leu Leu Tyr
1               5

<210> SEQ ID NO 69
<211> LENGTH: 4
<212> TYPE: PRT
<213> ORGANISM: Mus musculus

<400> SEQUENCE: 69

Ser Leu Leu Tyr
1

<210> SEQ ID NO 70
<211> LENGTH: 11
<212> TYPE: PRT
<213> ORGANISM: Mus musculus

<400> SEQUENCE: 70

Val Thr Asp Tyr Gly Tyr Val Tyr Phe Asp Ala
1               5                   10

<210> SEQ ID NO 71
<211> LENGTH: 9
<212> TYPE: PRT
<213> ORGANISM: Mus musculus

<400> SEQUENCE: 71

Asp Tyr Gly Tyr Val Tyr Phe Asp Ala
1               5

<210> SEQ ID NO 72
<211> LENGTH: 9
<212> TYPE: PRT
<213> ORGANISM: Mus musculus

<400> SEQUENCE: 72

Asp Tyr Tyr Tyr Val Tyr Phe Asp Val
1               5

<210> SEQ ID NO 73
<211> LENGTH: 12
<212> TYPE: PRT
```

<213> ORGANISM: Mus musculus

<400> SEQUENCE: 73

Gly Ile Tyr Tyr Asp Arg Ser Arg Ala Met Asp Tyr
1               5                   10

<210> SEQ ID NO 74
<211> LENGTH: 11
<212> TYPE: PRT
<213> ORGANISM: Mus musculus

<400> SEQUENCE: 74

Val Thr Asp Tyr Gly His Val Tyr Phe Asp Val
1               5                   10

<210> SEQ ID NO 75
<211> LENGTH: 4
<212> TYPE: PRT
<213> ORGANISM: Mus musculus

<400> SEQUENCE: 75

Arg Phe Ala Tyr
1

<210> SEQ ID NO 76
<211> LENGTH: 5
<212> TYPE: PRT
<213> ORGANISM: Mus musculus

<400> SEQUENCE: 76

Thr Tyr Tyr Asp Tyr
1               5

<210> SEQ ID NO 77
<211> LENGTH: 113
<212> TYPE: PRT
<213> ORGANISM: Mus musculus

<400> SEQUENCE: 77

Gln Val Gln Leu Gln Gln Ser Gly Ala Glu Val Val Lys Pro Gly Ala
1               5                   10                  15

Ser Val Lys Leu Ser Cys Lys Ala Ser Gly Tyr Thr Phe Thr Ser Tyr
                20                  25                  30

Tyr Leu Tyr Trp Val Lys Lys Gly Pro Gly Gln Gly Leu Asp Trp Ile
            35                  40                  45

Gly Glu Ile Tyr Pro Arg Ser Gly Gly Thr Asn Ile Asn Glu Lys Phe
        50                  55                  60

Leu Ser Lys Ala Thr Leu Thr Ala Asp Glu Ser Ser Ser Thr Ala Tyr
65                  70                  75                  80

Leu Gln Leu Ser Ser Leu Thr Ser Glu Asp Ser Ala Val Tyr Tyr Cys
                85                  90                  95

Thr Arg Ser Leu Leu Tyr Trp Gly Gln Gly Thr Thr Leu Ile Val Ser
                100                 105                 110

Ser

<210> SEQ ID NO 78
<211> LENGTH: 120
<212> TYPE: PRT
<213> ORGANISM: Mus musculus

<400> SEQUENCE: 78

Glu Val Gln Leu Val Glu Ser Gly Gly Gly Leu Val Gln Pro Lys Gly
1               5                   10                  15

Ser Leu Lys Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Ile
        35                  40                  45

Ala Arg Ile Arg Ser Lys Ser Asn Asn Tyr Ala Thr Tyr Tyr Ala Asp
    50                  55                  60

Ser Val Lys Asp Arg Phe Thr Ile Ser Arg Asp Asp Ser Gln Ser Leu
65                  70                  75                  80

Leu Tyr Leu Gln Met Asn Asn Leu Lys Thr Glu Asp Thr Ala Ile Phe
                85                  90                  95

Tyr Cys Val Thr Asp Tyr Gly Tyr Val Tyr Phe Asp Ala Trp Gly Ala
            100                 105                 110

Gly Thr Thr Val Thr Val Ser Ser
            115                 120

<210> SEQ ID NO 79
<211> LENGTH: 120
<212> TYPE: PRT
<213> ORGANISM: Mus musculus

<400> SEQUENCE: 79

Glu Val Gln Leu Leu Glu Ser Gly Gly Gly Leu Val Gln Pro Glu Gly
1               5                   10                  15

Ser Leu Lys Leu Ser Cys Ala Ala Ser Gly Phe Ala Phe Asn Thr Tyr
            20                  25                  30

Ala Met Asn Trp Val Arg Gln Ala Pro Gly Lys Gly Leu Glu Trp Leu
        35                  40                  45

Ala Arg Ile Arg Ser Lys Ser Asn Asn Tyr Ala Thr Tyr Tyr Ala Asp
    50                  55                  60

Ser Val Lys Asp Arg Phe Thr Ile Ser Arg Asp Asp Ser Gln Gly Met
65                  70                  75                  80

Leu Tyr Leu Gln Met Asn Asn Leu Lys Thr Glu Asp Thr Ala Met Tyr
                85                  90                  95

Tyr Cys Val Thr Asp Tyr Tyr Tyr Val Tyr Phe Asp Val Trp Gly Ala
            100                 105                 110

Gly Thr Thr Val Thr Val Ser Ser
            115                 120

<210> SEQ ID NO 80
<211> LENGTH: 121
<212> TYPE: PRT
<213> ORGANISM: Mus musculus

<400> SEQUENCE: 80

Gln Val Gln Leu Gln Gln Ser Gly Ala Glu Leu Ala Arg Pro Gly Ala
1               5                   10                  15

Ser Val Lys Leu Ser Cys Lys Ala Ser Gly Tyr Thr Phe Ser Ser His
            20                  25                  30

Trp Met Gln Trp Val Lys Gln Arg Pro Gly Gln Gly Leu Glu Trp Ile
        35                  40                  45

Gly Ala Ile Tyr Pro Gly Asp Gly Asp Thr Arg Phe Thr Gln Lys Phe
    50                  55                  60

Lys Gly Lys Ala Thr Leu Thr Ala Asp Lys Ser Ser Asn Thr Ala Tyr
65                  70                  75                  80

```
Met Gln Leu Ser Ser Leu Ala Ser Glu Asp Ser Ala Val Tyr Tyr Cys
                85                  90                  95

Ala Arg Gly Ile Tyr Tyr Asp Arg Ser Arg Ala Met Asp Tyr Trp Gly
            100                 105                 110

Gln Gly Thr Ser Val Thr Val Ser Ser
            115                 120

<210> SEQ ID NO 81
<211> LENGTH: 120
<212> TYPE: PRT
<213> ORGANISM: Mus musculus

<400> SEQUENCE: 81

Glu Val Gln Leu Val Glu Ser Gly Gly Gly Leu Val Gln Pro Lys Gly
1               5                   10                  15

Ser Leu Lys Leu Ser Cys Ala Thr Ser Gly Phe Thr Phe Asn Thr Tyr
                20                  25                  30

Ala Met Asn Trp Val Arg Gln Ala Pro Gly Lys Gly Leu Glu Trp Val
            35                  40                  45

Ala Arg Ile Arg Ser Lys Ser Asn Asn Tyr Ala Thr Tyr Tyr Val Asp
50                  55                  60

Ser Val Lys Asp Arg Phe Thr Ile Ser Arg Asp Asp Ser Gln Ser Thr
65                  70                  75                  80

Val His Leu Gln Met Asn Asn Leu Lys Thr Glu Asp Thr Ala Ile Tyr
                85                  90                  95

Tyr Cys Val Thr Asp Tyr Gly His Val Tyr Phe Asp Val Trp Gly Ala
            100                 105                 110

Gly Thr Thr Val Thr Val Ser Ser
            115                 120

<210> SEQ ID NO 82
<211> LENGTH: 113
<212> TYPE: PRT
<213> ORGANISM: Mus musculus

<400> SEQUENCE: 82

Gln Val Gln Leu Gln Gln Ser Gly Ala Glu Leu Val Lys Pro Gly Ala
1               5                   10                  15

Ser Val Lys Leu Ser Cys Lys Ala Ser Gly Tyr Thr Phe Thr Asn Tyr
                20                  25                  30

Tyr Met Tyr Trp Val Lys Gln Arg Pro Gly Gln Gly Leu Glu Trp Ile
            35                  40                  45

Gly Glu Ile Asn Pro Gly Asn Gly Gly Thr Asn Phe Asn Glu Lys Phe
50                  55                  60

Lys Asn Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Thr Thr Arg Phe Ala Tyr Trp Gly Gln Gly Thr Leu Val Ile Val Ser
            100                 105                 110

Ala

<210> SEQ ID NO 83
<211> LENGTH: 114
<212> TYPE: PRT
<213> ORGANISM: Mus musculus

<400> SEQUENCE: 83
```

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Ala Asp Tyr
            20                  25                  30

Tyr Met Lys Trp Val Lys Gln Ser His Gly Lys Ser Leu Glu Trp Ile
        35                  40                  45

Gly Asp Ile Asn Pro Asn Ser Gly Asp Thr Phe Tyr Asn His Lys Phe
    50                  55                  60

Lys Gly Lys Ala Thr Leu Thr Val Asp Lys Ser Ser Thr Ala Tyr
65                  70                  75                  80

Met Gln Leu Asn Ser Leu Thr Ser Glu Asp Ser Ala Val Tyr Tyr Cys
            85                  90                  95

Ala Arg Thr Tyr Tyr Asp Tyr Trp Gly Gln Gly Thr Thr Leu Thr Val
            100                 105                 110

Ser Ser

<210> SEQ ID NO 84
<211> LENGTH: 113
<212> TYPE: PRT
<213> ORGANISM: Artificial Sequence
<220> FEATURE:
<223> OTHER INFORMATION: Heavy Chain Variable Region

<400> SEQUENCE: 84

Gln Val Gln Leu Val Gln Ser Gly Ala Glu Val Val Lys Pro Gly Ala
1               5                   10                  15

Ser Val Lys Leu Ser Cys Lys Ala Ser Gly Tyr Thr Phe Thr Ser Tyr
            20                  25                  30

Tyr Leu Tyr Trp Val Lys Lys Ala Pro Gly Gln Gly Leu Asp Trp Ile
        35                  40                  45

Gly Glu Ile Tyr Pro Arg Ser Gly Gly Thr Asn Tyr Ala Glu Lys Phe
    50                  55                  60

Gln Gly Arg Val Thr Leu Thr Ala Asp Thr Ser Thr Ser Thr Ala Tyr
65                  70                  75                  80

Leu Glu Leu Ser Ser Leu Thr Ser Glu Asp Thr Ala Val Tyr Tyr Cys
            85                  90                  95

Thr Arg Ser Leu Leu Tyr Trp Gly Gln Gly Thr Thr Leu Thr Val Ser
            100                 105                 110

Ser

<210> SEQ ID NO 85
<211> LENGTH: 113
<212> TYPE: PRT
<213> ORGANISM: Artificial Sequence
<220> FEATURE:
<223> OTHER INFORMATION: Heavy Chain Variable Region

<400> SEQUENCE: 85

Gln Val Gln Leu Val Gln Ser Gly Ala Glu Val Val Lys Pro Gly Ala
1               5                   10                  15

Ser Val Lys Leu Ser Cys Lys Ala Ser Gly Tyr Thr Phe Thr Ser Tyr
            20                  25                  30

Tyr Leu Tyr Trp Val Lys Lys Ala Pro Gly Gln Gly Leu Asp Trp Ile
        35                  40                  45

Gly Glu Ile Tyr Pro Arg Ser Gly Gly Thr Asn Ile Asn Glu Lys Phe
    50                  55                  60

Leu Ser Arg Val Thr Leu Thr Ala Asp Thr Ser Ser Thr Ala Tyr
65                  70                  75                  80

Leu Glu Leu Ser Ser Leu Thr Ser Glu Asp Thr Ala Val Tyr Tyr Cys
                85                  90                  95

Thr Arg Ser Leu Leu Tyr Trp Gly Gln Gly Thr Leu Thr Val Ser
            100                 105                 110

Ser

<210> SEQ ID NO 86
<211> LENGTH: 113
<212> TYPE: PRT
<213> ORGANISM: Artificial Sequence
<220> FEATURE:
<223> OTHER INFORMATION: Heavy Chain Variable Region

<400> SEQUENCE: 86

Gln Val Gln Leu Gln Gln Ser Gly Ala Glu Val Val Lys Pro Gly Ala
1               5                   10                  15

Ser Val Lys Leu Ser Cys Lys Ala Ser Gly Tyr Thr Phe Thr Ser Tyr
            20                  25                  30

Tyr Leu Tyr Trp Val Lys Lys Ala Pro Gly Gln Gly Leu Asp Trp Ile
        35                  40                  45

Gly Glu Ile Tyr Pro Arg Ser Gly Gly Thr Asn Ile Asn Glu Lys Phe
    50                  55                  60

Leu Ser Arg Val Thr Leu Thr Ala Asp Thr Ser Ser Thr Ala Tyr
65                  70                  75                  80

Met Asp Leu Ser Ser Leu Thr Ser Glu Asp Thr Ala Val Tyr Tyr Cys
                85                  90                  95

Thr Arg Ser Leu Leu Tyr Trp Gly Gln Gly Thr Leu Thr Val Ser
            100                 105                 110

Ser

<210> SEQ ID NO 87
<211> LENGTH: 113
<212> TYPE: PRT
<213> ORGANISM: Artificial Sequence
<220> FEATURE:
<223> OTHER INFORMATION: Heavy Chain Variable Region

<400> SEQUENCE: 87

Gln Val Gln Leu Gln Gln Ser Gly Ala Glu Val Val Lys Pro Gly Ala
1               5                   10                  15

Ser Val Lys Leu Ser Cys Lys Ala Ser Gly Tyr Thr Phe Thr Ser Tyr
            20                  25                  30

Tyr Leu Tyr Trp Val Lys Lys Ala Pro Gly Gln Gly Leu Asp Trp Ile
        35                  40                  45

Gly Glu Ile Tyr Pro Arg Ser Gly Gly Thr Asn Ile Asn Glu Lys Phe
    50                  55                  60

Leu Ser Arg Val Thr Ile Thr Ala Asp Glu Ser Thr Ser Thr Val Tyr
65                  70                  75                  80

Met Gln Leu Ser Ser Leu Thr Ser Glu Asp Ser Ala Val Tyr Tyr Cys
                85                  90                  95

Thr Arg Ser Leu Leu Tyr Trp Gly Gln Gly Thr Leu Thr Val Ser
            100                 105                 110

Ser

<210> SEQ ID NO 88

<211> LENGTH: 443
<212> TYPE: PRT
<213> ORGANISM: Artificial Sequence
<220> FEATURE:
<223> OTHER INFORMATION: Heavy Chain Variable Region

<400> SEQUENCE: 88

```
Gln Val Gln Leu Val Gln Ser Gly Ala Glu Val Lys Pro Gly Ala
1               5                   10                  15

Ser Val Lys Leu Ser Cys Lys Ala Ser Gly Tyr Thr Phe Thr Ser Tyr
            20                  25                  30

Tyr Leu Tyr Trp Val Lys Lys Ala Pro Gly Gln Gly Leu Asp Trp Ile
        35                  40                  45

Gly Glu Ile Tyr Pro Arg Ser Gly Gly Thr Asn Ile Asn Glu Lys Phe
50                  55                  60

Leu Ser Arg Val Thr Leu Thr Ala Asp Thr Ser Thr Ser Thr Ala Tyr
65                  70                  75                  80

Leu Glu Leu Ser Ser Leu Thr Ser Glu Asp Thr Ala Val Tyr Tyr Cys
                85                  90                  95

Thr Arg Ser Leu Leu Tyr Trp Gly Gln Gly Thr Thr Leu Thr Val Ser
            100                 105                 110

Ser Ala Ser Thr Lys Gly Pro Ser Val Phe Pro Leu Ala Pro Ser Ser
        115                 120                 125

Lys Ser Thr Ser Gly Gly Thr Ala Ala Leu Gly Cys Leu Val Lys Asp
130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Gln
            180                 185                 190

Thr Tyr Ile Cys Asn Val Asn His Lys Pro Ser Asn Thr Lys Val Asp
        195                 200                 205

Lys Lys Val Glu Pro Lys Ser Cys Asp Lys Thr His Thr Cys Pro Pro
210                 215                 220

Cys Pro Ala Pro Glu Leu Leu Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser His Glu Asp Pro Glu Val Lys Phe Asn
            260                 265                 270

Trp Tyr Val Asp Gly Val Glu Val His Asn Ala Lys Thr Lys Pro Arg
        275                 280                 285

Glu Glu Gln Tyr Asn Ser Thr Tyr Arg Val Val Ser Val Leu Thr Val
290                 295                 300

Leu His Gln Asp Trp Leu Asn Gly Lys Glu Tyr Lys Cys Lys Val Ser
305                 310                 315                 320

Asn Lys Ala Leu Pro Ala Pro Ile Glu Lys Thr Ile Ser Lys Ala Lys
                325                 330                 335

Gly Gln Pro Arg Glu Pro Gln Val Tyr Thr Leu Pro Pro Ser Arg Glu
            340                 345                 350

Glu Met Thr Lys Asn Gln Val Ser Leu Thr Cys Leu Val Lys Gly Phe
        355                 360                 365

Tyr Pro Ser Asp Ile Ala Val Glu Trp Glu Ser Asn Gly Gln Pro Glu
370                 375                 380
```

```
Asn Asn Tyr Lys Thr Thr Pro Pro Val Leu Asp Ser Asp Gly Ser Phe
385                 390                 395                 400

Phe Leu Tyr Ser Lys Leu Thr Val Asp Lys Ser Arg Trp Gln Gln Gly
                405                 410                 415

Asn Val Phe Ser Cys Ser Val Met His Glu Ala Leu His Asn His Tyr
            420                 425                 430

Thr Gln Lys Ser Leu Ser Leu Ser Pro Gly Lys
        435                 440

<210> SEQ ID NO 89
<211> LENGTH: 14
<212> TYPE: PRT
<213> ORGANISM: Homo sapiens

<400> SEQUENCE: 89

Ala Gly Glu Gly Pro Lys Glu Gly Glu Ala Val Val Leu Pro
1               5                   10

<210> SEQ ID NO 90
<211> LENGTH: 11
<212> TYPE: PRT
<213> ORGANISM: Homo sapiens

<400> SEQUENCE: 90

Gly Pro Lys Glu Gly Glu Ala Val Val Leu Pro
1               5                   10

<210> SEQ ID NO 91
<211> LENGTH: 11
<212> TYPE: PRT
<213> ORGANISM: Artificial Sequence
<220> FEATURE:
<223> OTHER INFORMATION: Syndecan-1 Peptide
<220> FEATURE:
<221> NAME/KEY: SITE
<222> LOCATION: (2)..(2)
<223> OTHER INFORMATION: Xaa is any amino acid
<220> FEATURE:
<221> NAME/KEY: SITE
<222> LOCATION: (5)..(5)
<223> OTHER INFORMATION: Xaa is any amino acid
<220> FEATURE:
<221> NAME/KEY: SITE
<222> LOCATION: (8)..(8)
<223> OTHER INFORMATION: Xaa is any amino acid

<400> SEQUENCE: 91

Gly Xaa Lys Glu Xaa Glu Ala Xaa Val Leu Pro
1               5                   10

<210> SEQ ID NO 92
<211> LENGTH: 19
<212> TYPE: PRT
<213> ORGANISM: Homo sapiens

<400> SEQUENCE: 92

Ala Gly Glu Gly Pro Lys Glu Gly Glu Ala Val Val Leu Pro Glu Val
1               5                   10                  15

Glu Pro Gly

<210> SEQ ID NO 93
<211> LENGTH: 19
<212> TYPE: PRT
<213> ORGANISM: Homo sapiens
```

```
<400> SEQUENCE: 93

Lys Glu Gly Glu Ala Val Val Leu Pro Glu Val Glu Pro Gly Leu Thr
1               5                   10                  15

Ala Arg Glu

<210> SEQ ID NO 94
<211> LENGTH: 19
<212> TYPE: PRT
<213> ORGANISM: Homo sapiens

<400> SEQUENCE: 94

Val Val Leu Pro Glu Val Glu Pro Gly Leu Thr Ala Arg Glu Gln Glu
1               5                   10                  15

Ala Thr Pro

<210> SEQ ID NO 95
<211> LENGTH: 17
<212> TYPE: PRT
<213> ORGANISM: Homo sapiens

<400> SEQUENCE: 95

Pro Glu Pro Thr Gly Leu Glu Ala Thr Thr Ala Ser Thr Ser Thr Leu
1               5                   10                  15

Pro

<210> SEQ ID NO 96
<211> LENGTH: 11
<212> TYPE: PRT
<213> ORGANISM: Homo sapiens

<400> SEQUENCE: 96

Glu Thr Thr Gln Leu Pro Thr Thr His Gln Ala
1               5                   10

<210> SEQ ID NO 97
<211> LENGTH: 24
<212> TYPE: PRT
<213> ORGANISM: Homo sapiens

<400> SEQUENCE: 97

Ala Thr Thr Ala Gln Glu Pro Ala Thr Ser His Pro His Arg Asp Met
1               5                   10                  15

Gln Pro Gly His His Glu Thr Ser
            20

<210> SEQ ID NO 98
<211> LENGTH: 21
<212> TYPE: PRT
<213> ORGANISM: Homo sapiens

<400> SEQUENCE: 98

Gln Ala Ala Val Thr Ser His Pro His Gly Gly Met Gln Pro Gly Leu
1               5                   10                  15

His Glu Thr Ser Ala
            20

<210> SEQ ID NO 99
<211> LENGTH: 311
<212> TYPE: PRT
<213> ORGANISM: Mus musculus

<400> SEQUENCE: 99
```

```
Met Arg Arg Ala Ala Leu Trp Leu Trp Leu Cys Ala Leu Ala Leu Arg
1               5                   10                  15

Leu Gln Pro Ala Leu Pro Gln Ile Val Ala Val Asn Val Pro Pro Glu
            20                  25                  30

Asp Gln Asp Gly Ser Gly Asp Ser Asp Asn Phe Ser Gly Ser Gly
            35                  40                  45

Thr Gly Ala Leu Pro Asp Thr Leu Ser Arg Gln Thr Pro Ser Thr Trp
50                      55                  60

Lys Asp Val Trp Leu Leu Thr Ala Thr Pro Thr Ala Pro Glu Pro Thr
65                      70                  75                  80

Ser Ser Asn Thr Glu Thr Ala Phe Thr Ser Val Leu Pro Ala Gly Glu
                85                  90                  95

Lys Pro Glu Glu Gly Glu Pro Val Leu His Val Glu Ala Glu Pro Gly
            100                 105                 110

Phe Thr Ala Arg Asp Lys Glu Lys Glu Val Thr Thr Arg Pro Arg Glu
            115                 120                 125

Thr Val Gln Leu Pro Ile Thr Gln Arg Ala Ser Thr Val Arg Val Thr
130                 135                 140

Thr Ala Gln Ala Ala Val Thr Ser His Pro His Gly Gly Met Gln Pro
145                 150                 155                 160

Gly Leu His Glu Thr Ser Ala Pro Thr Ala Pro Gly Gln Pro Asp His
                165                 170                 175

Gln Pro Pro Arg Val Glu Gly Gly Thr Ser Val Ile Lys Glu Val
            180                 185                 190

Val Glu Asp Gly Thr Ala Asn Gln Leu Pro Ala Gly Glu Gly Ser Gly
            195                 200                 205

Glu Gln Asp Phe Thr Phe Glu Thr Ser Gly Glu Asn Thr Ala Val Ala
210                 215                 220

Ala Val Glu Pro Gly Leu Arg Asn Gln Pro Val Asp Glu Gly Ala
225                 230                 235                 240

Thr Gly Ala Ser Gln Ser Leu Leu Asp Arg Lys Glu Val Leu Gly Gly
                245                 250                 255

Val Ile Ala Gly Gly Leu Val Gly Leu Ile Phe Ala Val Cys Leu Val
            260                 265                 270

Ala Phe Met Leu Tyr Arg Met Lys Lys Lys Asp Glu Gly Ser Tyr Ser
            275                 280                 285

Leu Glu Glu Pro Lys Gln Ala Asn Gly Gly Ala Tyr Gln Lys Pro Thr
    290                 295                 300

Lys Gln Glu Glu Phe Tyr Ala
305                 310

<210> SEQ ID NO 100
<211> LENGTH: 313
<212> TYPE: PRT
<213> ORGANISM: Rattus norvegicus

<400> SEQUENCE: 100

Met Arg Arg Ala Ala Leu Trp Leu Trp Leu Cys Ala Leu Ala Leu Arg
1               5                   10                  15

Leu Gln Pro Ala Leu Pro Gln Ile Val Thr Ala Asn Val Pro Pro Glu
            20                  25                  30

Asp Gln Asp Gly Ser Gly Asp Ser Asp Asn Phe Ser Gly Ser Gly
            35                  40                  45

Thr Gly Ala Leu Pro Asp Met Thr Leu Ser Arg Gln Thr Pro Ser Thr
```

```
              50                  55                  60
Trp Lys Asp Val Trp Leu Leu Thr Ala Thr Pro Thr Ala Pro Glu Pro
 65                  70                  75                  80

Thr Ser Arg Asp Thr Glu Ala Thr Leu Thr Ser Ile Leu Pro Ala Gly
                 85                  90                  95

Glu Lys Pro Glu Glu Gly Glu Pro Val Ala His Val Glu Ala Glu Pro
            100                 105                 110

Asp Phe Thr Ala Arg Asp Lys Glu Lys Glu Ala Thr Thr Arg Pro Arg
        115                 120                 125

Glu Thr Thr Gln Leu Pro Val Thr Gln Gln Ala Ser Thr Ala Ala Arg
    130                 135                 140

Ala Thr Thr Ala Gln Ala Ser Val Thr Ser His Pro His Gly Asp Val
145                 150                 155                 160

Gln Pro Gly Leu His Glu Thr Leu Ala Pro Thr Ala Pro Gly Gln Pro
                165                 170                 175

Asp His Gln Pro Pro Ser Val Glu Asp Gly Gly Thr Ser Val Ile Lys
            180                 185                 190

Glu Val Val Glu Asp Glu Thr Thr Asn Gln Leu Pro Ala Gly Glu Gly
        195                 200                 205

Ser Gly Glu Gln Asp Phe Thr Phe Glu Thr Ser Gly Glu Asn Thr Ala
    210                 215                 220

Val Ala Gly Val Glu Pro Asp Leu Arg Asn Gln Ser Pro Val Asp Glu
225                 230                 235                 240

Gly Ala Thr Gly Ala Ser Gln Gly Leu Leu Asp Arg Lys Glu Val Leu
                245                 250                 255

Gly Gly Val Ile Ala Gly Gly Leu Val Gly Leu Ile Phe Ala Val Cys
            260                 265                 270

Leu Val Ala Phe Met Leu Tyr Arg Met Lys Lys Lys Asp Glu Gly Ser
        275                 280                 285

Tyr Ser Leu Glu Glu Pro Lys Gln Ala Asn Gly Gly Ala Tyr Gln Lys
    290                 295                 300

Pro Thr Lys Gln Glu Glu Phe Tyr Ala
305                 310

<210> SEQ ID NO 101
<211> LENGTH: 338
<212> TYPE: PRT
<213> ORGANISM: Macaca mulatta

<400> SEQUENCE: 101

Met Gly Ala Thr Ala Tyr Ile Pro Asn Ser Asn Ser Leu Ser Ala Leu
 1               5                  10                  15

Leu Arg Gly Leu Glu Leu Pro His Gln Thr Glu Leu Leu Arg Val Arg
                20                  25                  30

Ala Leu Pro Thr Leu Leu Cys Pro Cys Ala Leu Cys Arg Ala Pro Gly
            35                  40                  45

Cys Val Gln Ile Val Ala Thr Asn Leu Pro Pro Glu Asp Gln Asp Gly
        50                  55                  60

Ser Gly Asp Asp Ser Asp Asn Phe Ser Gly Ser Gly Ala Gly Ala Leu
 65                 70                  75                  80

Gln Asp Ile Thr Leu Ser Gln Gln Thr Pro Ser Thr Trp Lys Asp Thr
                85                  90                  95

Trp Leu Leu Thr Ala Thr Pro Met Ser Pro Glu Pro Thr Gly Leu Glu
            100                 105                 110
```

```
Ala Thr Ala Ala Ser Thr Ser Thr Leu Pro Ala Gly Glu Gly Pro Lys
            115                 120                 125

Glu Gly Glu Ala Val Val Leu Leu Glu Val Glu Pro Asp Leu Thr Ala
130                 135                 140

Arg Glu Gln Glu Ala Thr Pro Gln Pro Thr Glu Thr Thr Gln Leu Pro
145                 150                 155                 160

Thr Thr His Gln Ala Pro Thr Ala Arg Ala Thr Thr Ala Gln Glu Pro
                165                 170                 175

Ala Thr Ser His Pro His Arg Asp Met Gln Pro Gly His His Glu Thr
            180                 185                 190

Ser Ala Pro Ala Gly Pro Gly Gln Ala Asp Leu His Thr Pro Arg Thr
        195                 200                 205

Glu Asp Gly Gly Pro Ser Ala Thr Glu Arg Ala Ala Glu Asp Gly Ala
    210                 215                 220

Ser Ser Gln Leu Pro Ala Ala Glu Gly Ser Gly Glu Gln Asp Phe Thr
225                 230                 235                 240

Phe Glu Thr Ser Gly Glu Asn Thr Ala Ile Val Ala Val Glu Pro Asp
                245                 250                 255

His Arg Asn Gln Ser Pro Val Asp Pro Gly Ala Thr Gly Ala Ser Gln
            260                 265                 270

Gly Leu Leu Asp Arg Lys Glu Val Leu Gly Gly Ile Ile Ala Gly Gly
        275                 280                 285

Leu Val Gly Leu Ile Phe Ala Val Cys Leu Val Gly Phe Met Leu Tyr
    290                 295                 300

Arg Met Lys Lys Lys Asp Glu Gly Ser Tyr Ser Leu Glu Glu Pro Lys
305                 310                 315                 320

Gln Ala Asn Gly Gly Ala Tyr Gln Lys Pro Thr Lys Gln Glu Glu Phe
                325                 330                 335

Tyr Ala

<210> SEQ ID NO 102
<211> LENGTH: 310
<212> TYPE: PRT
<213> ORGANISM: Canis lupus familiaris

<400> SEQUENCE: 102

Met Arg Arg Ala Ala Leu Trp Leu Trp Leu Cys Ala Leu Ala Leu Arg
1               5                   10                  15

Leu Gln Pro Ala Leu Pro Gln Ile Val Ala Thr Asn Val Pro Pro Glu
                20                  25                  30

Asp Gln Asp Gly Ser Gly Asp Asp Ser Asp Asn Phe Ser Gly Ser Gly
            35                  40                  45

Ala Gly Ala Leu Gln Asp Ile Thr Leu Ser Gln Gln Thr Pro Ser Thr
        50                  55                  60

Trp Lys Asp Met Ala Leu Leu Thr Ala Met Pro Thr Ala Gln Glu Pro
65                  70                  75                  80

Thr Gly Ala Asp Asp Ile Asp Ser Ser Thr Ser Ile Leu Leu Thr Arg
                85                  90                  95

Glu Gly Pro Glu Gly Gly Glu Ala Val Leu Val Ala Glu Ala Glu Pro
            100                 105                 110

Gly Phe Thr Asp Arg Glu Lys Glu Thr Ala His Pro Pro Ser Glu Thr
        115                 120                 125

Thr Pro His Pro Thr Thr His Arg Ala Ser Thr Ala Arg Ala Thr Thr
    130                 135                 140
```

```
Ala Gln Gly Pro Ala Thr Leu His Pro His Arg Asp Ala Gln Pro Asp
145                 150                 155                 160

His His Gln Ile Ser Val Leu Ala Glu Pro Ser Gln Leu Asp Pro His
                165                 170                 175

Thr Pro Arg Val Glu Asp Gly Gly Pro Ser Ala Thr Glu Arg Ala Ala
            180                 185                 190

Glu Asp Gly Val Ser Thr Gln Leu Pro Ala Gly Glu Gly Ser Gly Glu
        195                 200                 205

Gln Asp Phe Thr Phe Asp Val Ser Gly Glu Asn Thr Ala Gly Thr Ala
    210                 215                 220

Val Glu Pro Asp Gln Arg Asn Gln Pro Val Asp Arg Gly Ala Thr
225                 230                 235                 240

Gly Ala Ser Gln Gly Leu Leu Asp Arg Lys Glu Val Leu Gly Val
                245                 250                 255

Ile Ala Gly Gly Leu Val Gly Leu Ile Phe Ala Val Cys Leu Val Gly
                260                 265                 270

Phe Met Leu Tyr Arg Met Lys Lys Lys Asp Gly Ser Tyr Ser Leu
                275                 280                 285

Glu Glu Pro Lys Gln Ala Asn Gly Gly Ala Tyr Gln Lys Pro Ser Lys
290                 295                 300

Gln Glu Glu Phe Tyr Ala
305             310

<210> SEQ ID NO 103
<211> LENGTH: 310
<212> TYPE: PRT
<213> ORGANISM: Macaca fascicularis

<400> SEQUENCE: 103

Met Arg Arg Ala Ala Leu Trp Leu Trp Leu Cys Ala Leu Ala Leu Ser
1               5                   10                  15

Leu Gln Pro Ala Met Pro Gln Ile Val Ala Thr Asn Leu Pro Pro Glu
                20                  25                  30

Asp Gln Asp Gly Ser Gly Asp Asp Ser Asp Asn Phe Ser Gly Ser Gly
            35                  40                  45

Ala Gly Ala Leu Gln Asp Ile Thr Leu Ser Gln Gln Thr Pro Ser Thr
50                  55                  60

Trp Lys Asp Thr Trp Leu Val Arg Ala Thr Pro Met Ser Pro Glu Pro
65                  70                  75                  80

Thr Gly Leu Glu Ala Thr Ala Ala Ser Thr Ser Thr Ile Gln Ala Gly
                85                  90                  95

Glu Gly Pro Lys Glu Gly Glu Ala Val Val Leu Leu Glu Val Glu Pro
            100                 105                 110

Asp Leu Thr Ala Arg Glu Gln Glu Ala Thr Pro Gln Pro Thr Glu Thr
        115                 120                 125

Thr Gln Leu Pro Thr Thr His Gln Ala Pro Thr Ala Arg Ala Thr Thr
    130                 135                 140

Ala Gln Glu Pro Ala Thr Ser His Pro His Arg Asp Met Gln Pro Gly
145                 150                 155                 160

His His Glu Thr Ser Ala Pro Ala Gly Pro Gly Gln Ala Asp Leu His
                165                 170                 175

Thr Pro Arg Thr Glu Asp Gly Gly Pro Ser Ala Thr Glu Arg Ala Ala
            180                 185                 190

Glu Asp Gly Ala Ser Ser Gln Leu Pro Ala Ala Glu Gly Ser Gly Glu
        195                 200                 205
```

```
Gln Asp Phe Thr Phe Glu Thr Ser Gly Glu Asn Thr Ala Ile Val Ala
    210                 215                 220

Val Glu Pro Asp His Arg Asn Gln Ser Pro Val Asp Pro Gly Ala Thr
225                 230                 235                 240

Gly Ala Ser Gln Gly Leu Leu Asp Arg Lys Glu Val Leu Gly Gly Ile
            245                 250                 255

Ile Ala Gly Gly Leu Val Gly Leu Ile Phe Ala Val Cys Leu Val Gly
            260                 265                 270

Phe Met Leu Tyr Arg Met Lys Lys Lys Asp Glu Gly Ser Tyr Ser Leu
        275                 280                 285

Glu Glu Pro Lys Gln Ala Asn Gly Gly Ala Tyr Gln Lys Pro Thr Lys
    290                 295                 300

Gln Glu Glu Phe Tyr Ala
305                 310
```